United States Patent
Bagri et al.

(10) Patent No.: US 9,102,720 B2
(45) Date of Patent: Aug. 11, 2015

(54) ANTI-VEGF-C ANTIBODIES AND METHODS USING SAME

(71) Applicant: Genentech, Inc., South San Francisco, CA (US)

(72) Inventors: Anil D. Bagri, San Carlos, CA (US); Germaine Fuh, Pacifica, CA (US); Chingwei V. Lee, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/919,137

(22) Filed: Jun. 17, 2013

(65) Prior Publication Data

US 2013/0344072 A1 Dec. 26, 2013

Related U.S. Application Data

(62) Division of application No. 12/882,330, filed on Sep. 15, 2010, now Pat. No. 8,486,397.

(60) Provisional application No. 61/284,753, filed on Dec. 23, 2009, provisional application No. 61/285,910, filed on Dec. 11, 2009.

(51) Int. Cl.
    *C07K 16/22* (2006.01)
    *A61K 39/395* (2006.01)
    *A61K 39/00* (2006.01)

(52) U.S. Cl.
    CPC ............ *C07K 16/22* (2013.01); *A61K 39/3955* (2013.01); *A61K 2039/505* (2013.01); *A61K 2039/507* (2013.01); *C07K 2316/96* (2013.01); *C07K 2317/24* (2013.01); *C07K 2317/55* (2013.01); *C07K 2317/56* (2013.01); *C07K 2317/565* (2013.01); *C07K 2317/73* (2013.01); *C07K 2317/92* (2013.01); *C07K 2319/30* (2013.01); *C07K 2319/32* (2013.01)

(58) Field of Classification Search
    None
    See application file for complete search history.

(56) References Cited

U.S. PATENT DOCUMENTS

| 8,940,695 B2 * | 1/2015 | Alitalo et al. ............... 514/13.3 |
| 2004/0147448 A1 | 7/2004 | Alitalo et al. |

FOREIGN PATENT DOCUMENTS

| WO | 97/09427 | 3/1997 |
| WO | 2010/006232 A1 | 1/2010 |
| WO | 2011/032013 A1 | 3/2011 |

OTHER PUBLICATIONS

Ferrara et al., "Clinical applications of angiogenic growth factors and their inhibitors" NAT Med 5(12):1359-1364 (Dec. 1999).
Horak, E.R. et al., "Angiogenesis, assessed by platelet/endothelial cell adhesion molecule antibodies, as indicator of node metastases and survival in breast cancer" Lancet 340:1120-1124 (Nov. 7, 1992).
Houck et al., "The Vascular Endothelial Growth Factor Family: Identification of a Fourth Molecular Species and Characterization of Alternative Splicing of RNA" Mol Endocrinol 5(12):1806-14 ( 1991).
Ran, S et al., "Generation of new rabbit monoclonal antibody RAM-1 against human VEGF-C" Proceedings of the Annual Meeting of the American Association of Cancer Research 46:911 (Apr. 20, 2005).
Achen, M. G. et al., "Targeting lymphangiogenesis to prevent tumour metastasis" Brit J Cancer 94(10):1355-60 (May 2006).
Krishnan, J. et al., "Differential in vivo and in vitro expression of vascular endothelial growth factor (VEGF)-C and VEGF-D in tumors and its relationship to lymphatic metastasis in immunocompetent rats" Cancer Res 63:713-722 (Feb. 1, 2003).
Tonini et al., "Molecular basis of angiogenesis and cancer" Oncogene 22(42):6549-6556 (Sep. 29, 2003).
Kim, K. Jin et al., "Inhibition of vascular endothelial growth factor-induced angiogenesis suppresses tumour growth in vivo" Nature 362:841-844 (Apr. 29, 1993).
Borgstrom, P. et al., "Complete inhibition of angiogenesis and growth of microtumors by anti-vascular endothelial growth factor neutralizing antibody: novel concepts of angiostatic therapy from intravital videomicroscopy" Cancer Res 56(17):4032-4039 (Sep. 1, 1996).
Dvorak et al., "Vascular permeability factor/vascular endothelial growth factor, microvascular hyperpermeability, and angiogenesis" Am J Pathol 146(5):1029-1039 (May 1995).
Folkman, J. et al., "Induction of angiogenesis during the transition from hyperplasia to neoplasia" Nature 339(6219):58-61 ( 1989).
Hanahan, D., "Signaling vascular morphogenesis and maintenance" Science 277:48-50 (1997).
Sato, "Molecular diagnosis of tumor angiogenesis and anti-angiogenic cancer therapy" Int J Clin Oncol 8(4):200-206 (Aug. 2003).
Streit et al., "Angiogenesis, lymphangiogenesis, and melanoma metastasis" Oncogene 22(20):3172-3179 (May 19, 2003).
Ueda, M. et al., "Vascular endothelial growth factor-C expression and invasive phenotype in ovarian carcinomas" Clinical Cancer Research 11(9):3225-3232 (May 1, 2005).
Folkman and Shing, "Angiogenesis" J Biol Chem 267(16):10931-10934 (Jun. 5, 1992).
Lubarsky et al., "Tube morphogenesis: making and shaping biological tubes" Cell 112(1):19-28 (Jan. 10, 2003).
Melnyk, O. et al., "Vascular endothelial growth factor promotes tumor dissemination by a mechanism distinct from its effect on primary tumor growth" Cancer Res 56:921-924 (Feb. 15, 1996).
Rinderknecht, M et al., "Phage-derived fully human monoclonal antibody fragments to human vascular endothelial growth factor-C block its interaction with VEGF receptor-2 and 3" PLOS One 5(8):E11941 (2010).
Stacker, S. A. et al., "The role of tumor lymphangiogenesis in metastatic spread" FASEB J 16:922-934 ( 2002).
Hogan, B. L. M. et al., "Organogenesis: molecular mechanisms of tubulogenesis" Nat Rev Genet 3(7):513-523 (Jul. 2002).

(Continued)

*Primary Examiner* — Laura B Goddard
*Assistant Examiner* — Meera Natarajan
(74) *Attorney, Agent, or Firm* — Janet M. Martineau

(57) ABSTRACT

The invention provides VEGF-C antagonists, such as anti-VEGF-C antibodies, and their use in the prevention and treatment of tumor progression.

40 Claims, 37 Drawing Sheets

(56) References Cited

OTHER PUBLICATIONS

Gupta and Massague, "Cancer metastasis: building a framework" Cell 127(4):679-95 (Nov. 2006).
Lin, J. et al., "Inhibition of lymphogenous metastasis using adeno-associated virus-mediated gene transfer of a soluble VEGFR-3 decoy receptor" Cancer Res 65(15):6901-6909 (Aug. 1, 2005)
Lopez, P. F. et al., "Transdifferentiated retinal pigment epithelial cells are immunoreactive for vascular endothelial growth factor in surgically excised age-related macular degeneration-related choroidal neovascular membranes" Invest OPHTH VIS SCI 37(5):855-868 (Apr. 1996).
Brown, L. F. et al., "Expression of vascular permeability factor (vascular endothelial growth factor) and its receptors in breast cancer" Hum Pathol 26(1):86-91 (1995).
Karpanen, T. et al., "Functional interaction of VEGF-C and VEGF-D with neuropilin receptors" FASEB J 20:1462-1472 (Jul. 2006).
Warren et al., "Regulation by vascular endothelial growth factor of human colon cancer tumorigenesis in a mouse model of experimental liver metastasis" J Clin Invest 95:1789-1797 (Apr. 1995).
Garner, A. Pathobiology of Ocular Disease. A Dynamic Approach "Vascular Diseases" Garner, A., Klintworth GK Eds., 2nd edition, NY:Marcel Dekker,:1625-1710 (1994).
Cao et al., "Vascular endothelial growth factor C induces angiogenesis in vivo" Proc. Natl. Acad. Sci. USA 95:14389-14394 (Nov. 1998).
Shinkai, A. et al., "Mapping of the sites involved in ligand association and dissociation at the extracelular domain of the kinase insert domain-containing receptor for vascular endothelial growth factor" J Biol Chem 273(47):31283-31288 (Nov. 20, 1998).
Leung et al., "Vascular Endothelial Growth Factor Is a Secreted Angiogenic Mitogen" Science 246:1306-1309 (Dec. 1989).
Brown, L. F. et al., "Expression of vascular permeability factor (vascular endothelial growth factor) and its receptors in adenocarcinomas of the gastrointestinal tract" Cancer Res 53;4727-4735 (Oct. 1, 1993).
Aiello, L. P. et al., "Vascular endothelial growth factor in ocular fluid of patients with diabetic retinopathy and other retinal disorders" New Engl J Med 331(22);1480-1487 (Dec. 1, 1994).
Waltenberger, J. et al., "Different signal transduction properties of KDR and Flt1, two receptors for vascular endothelial growth factor" J Biol Chem 269(43);26988-26995 (Oct. 28, 1994).
Presta et al., "Humanization of an Anti-Vascular Endothelial Growth Factor Monoclonal Antibody for the Therapy of Solid Tumors and Other Disorders" Cancer Res 57(20):4593-4599 (Oct. 15, 1997).
Shin, H et al., "VEGF-C mediates cyclic pressure-induced endothelial cell proliferations" Physiological Genomics 11 (Jan. 2003).
Nathanson, S. D., "Insights into the mechanisms of lymph node metastasis" Cancer 98(2):413-23 (Jul. 2003).
Ferrara and Davis-Smyth, "The Biology of Vascular Endothelial Growth Factor" Endocr Rev 18(1):4-25 (1997).
Skobe, M. et al., "Induction of tumor lymphangiogenesis by VEGF-C promotes breast cancer metastasis" Nat Med 7(2):192-198 (Feb. 2001).
Timoshenko, A et al., "Migration-promoting role of VEGF-C and VEGF-C binding receptors in human breast cancel cells" British Journal of Cancer 97(8):1090-1098 (Oct. 1, 2007).
Albuquerque, R et al., "Alternatively spliced vascular endothelial growth factor receptor-2 is an essential endogenous inhibitor of lymphatic vessel growth" Nature Medicine 15(9):1023-1030 (Sep. 2009).
Alitalo et al., "Molecular mechanisms of lymphangiogenesis in health and disease" Cancer Cell 1:219-227 (Apr. 2002).
Mandriota, S. J. et al., "Vascular endothelial growth factor-C mediated lymphangiogenesis promotes tumour metastasis" EMBO J 20(4):672-682 (2001).
Liang et al., "Cross-species vascular endothelial growth factor (VEGF)-blocking antibodies completely inhibit the growth of human tumor xenografts and measure the contribution of stromal VEGF" J Biol Chem 281(2):951-961 (Jan. 13, 2006).
He, Y. et al., "Suppression of tumor lymphangiogenesis and lymph node metastasis by blocking vascular endothelial growth factor receptor 3 signaling" J Natl Cancer Institute 94(11):819-825 (2002).
Stacker, S. A. et al., "Lymphangiogenesis and cancer metastasis" Nat Rev Cancer 2:573-583 (Aug. 2002).
Klagsbrun and D'Amore, "Regulators of angiogenesis" Ann Rev Physiol 53:217-239 (1991).
Weidner, N. et al., "Tumor angiogenesis and metastasis—correlation in invasive breast carcinoma" New Engl J Med 324(1):1-8 (1991).
Berkman, R. A. et al., "Expression of the vascular permeability factor/vascular endothelial growth factor gene in central nervous system neoplasms" J Clin Invest 91:153-159 (Jan. 1993).
Su et al., "The VEGF-C/Flt-4 axis promotes invasion and metastasis of cancer cells" Cancer Cell 9:209-223 (Mar. 2006).
Macchiarini, P. et al., "Relation of neovascularisation to metastasis to non-small-cell lung cancer" Lancet 340:145-146 (Jul. 18, 1992).
Chen, Z. et al., "Down-regulation of vascular endothelial cell growth factor-C expression using small interfering RNA vectors in mammary tumors inhibits tumor lymphangiogenesis and spontaneous metastasis and enhances survival" Cancer Res 65(19):9004-911 (2005).
Heldin, C., "Dimerization of cell surface receptors in signal transduction" Cell 80:213-223 (Jan. 27, 1995).
Mattern, J. et al., "Association of vascular endothelial growth factor expression with intratumoral microvessel density and tumour cell proliferation in human epidermoid lung carcinoma" Brit J Cancer 73:931-934 (1996).
Shibata, M et al., "Combination therapy with short interfering RNA vectors against VEGF-C and VEGF-A suppresses lymph node and lung metastasis in a mouse immunocompetent mammary cancer model" Cancer Gene Therapy 15(12):776-786 (Jul. 1, 2008).
Adamis, A. P. et al., "Inhibition of Vascular Endothelial Growth Factor Prevents Retinal Ischemia-Associated Iris Neovascularization in a Nonhuman Primate" Arch Ophthalmoi-Chic 114(1):66-71 (1996).

* cited by examiner

| Clone # | H1 | | | | | | | | | | |
|---|---|---|---|---|---|---|---|---|---|---|---|
| | 26 | 27 | 28 | 29 | 30 | 31 | 32 | 33 | 34 | 35 |
| VC1 | G | F | T | F | S | D | S | D | I | H |
| VC1.1 | G | F | T | F | S | D | S | D | I | H |
| VC1.2 | G | F | T | F | S | D | S | D | I | H |
| VC1.3 | G | F | T | F | S | D | S | D | I | H |
| VC1.4 | G | F | T | F | S | D | S | D | I | H |
| VC1.5 | G | F | T | F | S | D | S | D | I | H |
| VC1.6 | G | F | T | F | S | D | S | D | I | H |
| VC1.7 | G | F | T | F | S | D | S | D | I | H |
| VC1.8 | G | F | T | F | S | D | S | D | I | H |
| VC1.9 | G | F | T | F | S | D | S | D | I | H |
| VC1.10 | G | F | T | F | S | D | S | D | I | H |
| VC1.11 | G | F | T | F | S | D | S | D | I | H |
| VC1.12 | G | F | T | F | S | D | S | D | I | H |
| VC1.12.1 | G | F | T | F | S | D | S | D | I | H |
| VC1.12.2 | G | F | T | F | S | D | S | D | I | H |
| VC1.12.3 | G | F | T | F | S | D | S | D | I | H |
| VC1.12.4 | G | F | T | F | S | D | S | D | I | H |
| VC1.12.5 | G | F | T | F | S | D | S | D | I | H |
| VC1.12.6 | G | F | T | F | S | D | S | D | I | H |
| VC1.12.8 | G | F | T | F | S | D | S | D | I | H |
| VC1.12.9 | G | F | T | F | S | D | S | D | I | H |
| VC1.12.10 | G | F | T | F | S | D | S | D | I | H |
| VC3 | G | F | T | F | T | N | T | D | I | H |
| VC4 | G | F | T | F | T | D | N | W | I | H |
| VC4.2 | G | F | T | F | T | D | N | W | I | H |
| VC4.3 | G | F | T | F | T | Y | S | W | I | H |
| VC4.4 | G | F | T | F | T | D | N | W | I | H |
| VC4.5 | G | F | T | F | T | D | N | W | I | H |

*FIG. 1A*

| Clone # | H2 | | | | | | | | | | | | | | | | | |
|---|---|---|---|---|---|---|---|---|---|---|---|---|---|---|---|---|---|---|
| | 49 | 50 | 51 | 52 | 52a | 53 | 54 | 55 | 56 | 57 | 58 | 59 | 60 | 61 | 62 | 63 | 64 | 65 |
| VC1 | A | W | I | S | P | Y | S | G | Y | T | D | Y | A | D | S | V | K | G |
| VC1.1 | A | W | I | S | P | Y | S | G | Y | T | D | Y | A | D | S | V | K | G |
| VC1.2 | A | W | I | S | P | Y | S | G | Y | T | D | Y | A | D | S | V | K | G |
| VC1.3 | A | W | I | S | P | Y | S | G | Y | T | D | Y | A | D | S | V | K | G |
| VC1.4 | A | W | I | S | P | Y | S | G | Y | T | D | Y | A | D | S | V | K | G |
| VC1.5 | A | W | I | S | P | Y | S | G | Y | T | D | Y | A | D | S | V | K | G |
| VC1.6 | A | W | I | S | P | Y | S | G | Y | T | D | Y | A | D | S | V | K | G |
| VC1.7 | A | W | I | S | P | Y | S | G | Y | T | D | Y | A | D | S | V | K | G |
| VC1.8 | A | W | I | S | P | Y | S | G | Y | T | D | Y | A | D | S | V | K | G |
| VC1.9 | A | W | I | S | P | Y | S | G | Y | T | D | Y | A | D | S | V | K | G |
| VC1.10 | A | W | I | S | P | Y | S | G | Y | T | D | Y | A | D | S | V | K | G |
| VC1.11 | A | W | I | S | P | Y | S | G | Y | T | D | Y | A | D | S | V | K | G |
| VC1.12 | A | W | I | S | P | Y | V | G | F | T | D | Y | A | D | S | V | K | G |
| VC1.12.1 | A | W | I | S | P | Y | V | G | F | T | D | Y | A | D | S | V | K | G |
| VC1.12.2 | A | W | I | S | P | Y | V | G | F | T | D | Y | A | D | S | V | K | G |
| VC1.12.3 | A | W | I | S | P | Y | V | G | F | T | D | Y | A | D | S | V | K | G |
| VC1.12.4 | A | W | I | S | P | Y | V | G | F | T | D | Y | A | D | S | V | K | G |
| VC1.12.5 | A | W | I | S | P | Y | V | G | F | T | D | Y | A | D | S | V | K | G |
| VC1.12.6 | A | W | I | S | P | Y | V | G | F | T | D | Y | A | D | S | V | K | G |
| VC1.12.8 | A | W | I | S | P | Y | V | G | Y | T | D | Y | A | D | S | V | K | G |
| VC1.12.9 | A | W | I | S | P | S | S | G | A | T | Y | Y | A | D | S | V | K | G |
| VC1.12.10 | A | W | I | S | P | Y | S | G | A | S | Y | Y | A | D | S | V | K | G |
| VC3 | A | W | I | S | P | Y | S | G | Y | T | D | Y | A | D | S | V | K | G |
| VC4 | G | V | I | S | P | Y | S | G | A | T | Y | Y | A | D | S | V | K | G |
| VC4.2 | G | V | I | S | P | G | V | G | Y | T | Y | Y | A | D | S | V | K | G |
| VC4.3 | G | F | I | S | P | Y | S | G | A | T | Y | Y | A | D | S | V | K | G |
| VC4.4 | G | V | I | S | P | Y | S | G | A | T | Y | Y | A | D | S | V | K | G |
| VC4.5 | G | V | I | S | P | Y | S | G | A | T | Y | Y | A | D | S | V | K | G |

| Clone # | H3 | | | | | | | | | | | | | | |
|---|---|---|---|---|---|---|---|---|---|---|---|---|---|---|---|
| | 93 | 94 | 95 | 96 | 97 | 98 | 99 | 100 | a | b | c | d | e | 101 | 102 |
| VC1 | A | R | L | F | E | V | I | F | - | - | - | - | - | D | Y |
| VC1.1 | A | R | L | F | K | V | I | F | - | - | - | - | - | D | Y |
| VC1.2 | A | R | L | F | E | V | I | F | - | - | - | - | - | D | Y |
| VC1.3 | V | R | L | F | G | - | I | F | - | - | - | - | - | D | Y |
| VC1.4 | V | R | L | W | E | V | I | F | - | - | - | - | - | D | Y |
| VC1.5 | A | R | L | F | E | V | I | F | - | - | - | - | - | D | Y |
| VC1.6 | V | R | L | F | D | V | I | F | - | - | - | - | - | D | Y |
| VC1.7 | A | R | L | F | T | - | I | F | - | - | - | - | - | D | Y |
| VC1.8 | T | R | L | F | D | V | I | F | - | - | - | - | - | D | Y |
| VC1.9 | S | R | L | F | G | - | I | F | - | - | - | - | - | D | Y |
| VC1.10 | V | R | L | F | D | V | I | F | - | - | - | - | - | D | Y |
| VC1.11 | V | R | L | F | D | V | I | F | - | - | - | - | - | D | Y |
| VC1.12 | A | R | L | F | D | V | I | F | - | - | - | - | - | D | Y |
| VC1.12.1 | A | R | L | F | D | V | I | F | - | - | - | - | - | D | Y |
| VC1.12.2 | A | R | L | F | D | V | I | F | - | - | - | - | - | D | Y |
| VC1.12.3 | A | R | L | F | D | V | I | F | - | - | - | - | - | D | Y |
| VC1.12.4 | A | R | L | F | D | V | I | F | - | - | - | - | - | D | Y |
| VC1.12.5 | A | R | L | F | D | V | I | F | - | - | - | - | - | D | Y |
| VC1.12.6 | A | R | L | F | D | V | I | F | - | - | - | - | - | D | Y |
| VC1.12.8 | A | R | L | F | D | V | I | F | - | - | - | - | - | D | Y |
| VC1.12.9 | A | R | L | F | D | V | I | F | - | - | - | - | - | D | Y |
| VC1.12.10 | A | R | L | F | D | V | I | F | - | - | - | - | - | D | Y |
| VC3 | A | R | W | R | D | Y | R | F | G | G | V | I | M | D | Y |
| VC4 | A | R | D | A | D | Y | D | Y | A | W | W | A | F | D | Y |
| VC4.2 | A | R | D | A | D | Y | A | Y | A | G | W | A | F | D | Y |
| VC4.3 | A | R | D | V | D | Y | D | Y | A | W | W | A | L | D | Y |
| VC4.4 | A | R | D | A | D | Y | Y | Y | A | F | W | A | F | D | Y |
| VC4.5 | A | R | D | A | D | Y | K | Y | A | W | W | A | F | D | Y |

FIG. 1D

| Clone # | L1 | | | | | | | | | | |
|---|---|---|---|---|---|---|---|---|---|---|---|
| | 24 | 25 | 26 | 27 | 28 | 29 | 30 | 31 | 32 | 33 | 34 |
| VC1 | R | A | S | Q | D | V | S | T | A | V | A |
| VC1.1 | R | A | S | Q | D | V | S | T | A | V | A |
| VC1.2 | R | A | S | Q | D | V | S | T | A | V | A |
| VC1.3 | R | A | S | Q | D | V | S | T | A | V | A |
| VC1.4 | R | A | S | Q | D | V | S | T | A | V | A |
| VC1.5 | R | A | S | Q | D | V | S | T | A | V | A |
| VC1.6 | R | A | S | Q | D | V | S | T | A | V | A |
| VC1.7 | R | A | S | Q | D | V | S | T | A | V | A |
| VC1.8 | R | A | S | Q | D | V | S | T | A | V | A |
| VC1.9 | R | A | S | Q | D | V | S | T | A | V | A |
| VC1.10 | R | A | S | Q | D | V | S | T | A | V | A |
| VC1.11 | R | A | S | Q | D | V | S | T | A | V | A |
| VC1.12 | R | A | S | Q | D | V | S | T | A | V | A |
| VC1.12.1 | R | A | S | Q | D | V | S | T | A | V | A |
| VC1.12.2 | R | A | S | Q | D | V | S | T | A | V | A |
| VC1.12.3 | R | A | S | Q | D | V | S | T | A | V | A |
| VC1.12.4 | R | A | S | Q | D | V | S | T | A | V | A |
| VC1.12.5 | R | A | S | Q | D | V | S | T | A | V | A |
| VC1.12.6 | R | A | S | Q | D | V | S | T | A | V | A |
| VC1.12.8 | R | A | S | Q | D | V | S | T | A | V | A |
| VC1.12.9 | R | A | S | Q | D | V | S | T | A | V | A |
| VC1.12.10 | R | A | S | Q | D | V | S | T | A | V | A |
| VC3 | R | A | S | Q | D | V | S | T | A | V | A |
| VC4 | R | A | S | Q | D | V | S | T | A | V | A |
| VC4.2 | R | A | S | Q | D | V | S | T | A | V | A |
| VC4.3 | R | A | S | Q | D | V | S | T | A | V | A |
| VC4.4 | R | A | S | Q | D | V | S | T | A | V | A |
| VC4.5 | R | A | S | Q | D | V | S | T | A | V | A |

| Clone # | L3 | | | | | | | | | |
|---|---|---|---|---|---|---|---|---|---|---|
| | 89 | 90 | 91 | 92 | 93 | 94 | 95 | 96 | 97 | |
| VC1 | Q | Q | S | Y | T | T | P | P | T | |
| VC1.1 | Q | Q | S | Y | T | T | P | P | T | |
| VC1.2 | Q | Q | S | Y | T | T | P | P | T | |
| VC1.3 | Q | Q | S | Y | T | T | P | P | T | |
| VC1.4 | Q | Q | S | Y | T | T | P | P | T | |
| VC1.5 | Q | Q | S | Y | T | T | P | P | T | |
| VC1.6 | Q | Q | S | Y | T | T | P | P | T | |
| VC1.7 | Q | Q | S | Y | T | T | P | P | T | |
| VC1.8 | Q | Q | S | Y | T | T | P | P | T | |
| VC1.9 | Q | Q | S | Y | T | T | P | P | T | |
| VC1.10 | Q | Q | S | Y | T | T | P | P | T | |
| VC1.11 | Q | Q | S | Y | T | T | P | P | T | |
| VC1.12 | Q | Q | S | Y | T | T | P | P | T | |
| VC1.12.1 | Q | Q | S | Y | N | I | P | L | T | |
| VC1.12.2 | Q | Q | S | Y | W | T | P | P | T | |
| VC1.12.3 | Q | Q | T | Y | A | I | P | P | T | |
| VC1.12.4 | Q | Q | S | Y | T | S | P | T | T | |
| VC1.12.5 | Q | Q | S | Y | T | T | P | P | T | |
| VC1.12.6 | Q | Q | S | Y | N | I | P | P | T | |
| VC1.12.8 | Q | Q | S | Y | I | S | P | P | T | |
| VC1.12.9 | Q | Q | S | Y | Y | T | P | P | T | |
| VC1.12.10 | Q | Q | S | Y | T | T | P | P | T | |
| VC3 | Q | Q | S | Y | T | I | P | P | T | |
| VC4 | Q | Q | T | Y | T | T | P | Y | T | |
| VC4.2 | Q | Q | S | Y | R | T | P | P | T | |
| VC4.3 | Q | Q | S | Y | T | T | P | P | T | |
| VC4.4 | Q | Q | S | Y | T | T | P | P | T | |
| VC4.5 | Q | Q | S | Y | T | T | P | P | T | |

FIG. 1F

| Clone # | L2 | | | | | | | |
|---|---|---|---|---|---|---|---|---|
| | 50 | 51 | 52 | 53 | 54 | 55 | 56 | |
| VC1 | S | A | S | F | L | Y | S | |
| VC1.1 | S | A | S | F | L | Y | S | |
| VC1.2 | S | A | S | F | L | Y | S | |
| VC1.3 | S | A | S | F | L | Y | S | |
| VC1.4 | S | A | S | F | L | Y | S | |
| VC1.5 | S | A | S | F | L | Y | S | |
| VC1.6 | S | A | S | F | L | Y | S | |
| VC1.7 | S | A | S | F | L | Y | S | |
| VC1.8 | S | A | S | F | L | Y | S | |
| VC1.9 | S | A | S | F | L | Y | S | |
| VC1.10 | S | A | S | F | L | Y | S | |
| VC1.11 | S | A | S | F | L | Y | S | |
| VC1.12 | S | A | S | F | L | Y | S | |
| VC1.12.1 | S | A | S | F | L | Y | S | |
| VC1.12.2 | S | A | S | F | L | Y | S | |
| VC1.12.3 | S | A | S | F | L | Y | S | |
| VC1.12.4 | S | A | S | F | L | Y | S | |
| VC1.12.5 | S | A | S | F | L | Y | S | |
| VC1.12.6 | S | A | S | F | L | Y | S | |
| VC1.12.8 | S | A | S | F | L | Y | S | |
| VC1.12.9 | S | A | S | F | L | Y | S | |
| VC1.12.10 | S | A | S | F | L | Y | S | |
| VC3 | S | A | S | F | L | Y | S | |
| VC4 | S | A | S | F | L | Y | S | |
| VC4.2 | S | A | S | F | L | Y | S | |
| VC4.3 | S | A | S | F | L | Y | S | |
| VC4.4 | S | A | S | F | L | Y | S | |
| VC4.5 | S | A | S | F | L | Y | S | |

FIG. 1E

| | | | |
|---|---|---|---|
| I | | | |
| A | QVQLVQSGAEVKKPGASVKVSCKASGYTFT | -H1- | WVRQAPGQGLEWMG | -H2- |
| B | QVQLVQSGAEVKKPGASVKVSCKAS | -H1- | WVRQAPGQGLEWM | -H2- |
| C | QVQLVQSGAEVKKPGASVKVSCKAS | -H1- | WVRQAPGQGLEWM | -H2- |
| D | QVQLVQSGAEVKKPGASVKVSCKAS | -H1- | WVRQAPGQGLEWM | -H2- |
| II | | | |
| A | QVQLQESGPGLVKPSQTLSLTCTVSGGSVS | -H1- | WIRQPPGKGLEWIG | -H2- |
| B | QVQLQESGPGLVKPSQTLSLTCTVS | -H1- | WIRQPPGKGLEWI | -H2- |
| C | QVQLQESGPGLVKPSQTLSLTCTVS | -H1- | WIRQPPGKGLEWI | -H2- |
| D | QVQLQESGPGLVKPSQTLSLTCTVS | -H1- | WIRQPPGKGLEWI | -H2- |
| III | | | |
| A | EVQLVESGGGLVQPGGSLRLSCAASGFTFS | -H1- | WVRQAPGKGLEWVS | -H2- |
| B | EVQLVESGGGLVQPGGSLRLSCAAS | -H1- | WVRQAPGKGLEWV | -H2- |
| C | EVQLVESGGGLVQPGGSLRLSCAAS | -H1- | WVRQAPGKGLEWV | -H2- |
| D | EVQLVESGGGLVQPGGSLRLSCAAS | -H1- | WVRQAPGKGLEWV | -H2- |
| Acceptor | | | |
| A | EVQLVESGGGLVQPGGSLRLSCAASGFNIK | -H1- | WVRQAPGKGLEWVS | -H2- |
| B | EVQLVESGGGLVQPGGSLRLSCAAS | -H1- | WVRQAPGKGLEWV | -H2- |
| C | EVQLVESGGGLVQPGGSLRLSCAAS | -H1- | WVRQAPGKGLEWV | -H2- |
| Second Acceptor | | | |
| A | EVQLVESGGGLVQPGGSLRLSCAASGFNIK | -H1- | WVRQAPGKGLEWVS | -H2- |
| B | EVQLVESGGGLVQPGGSLRLSCAAS | -H1- | WVRQAPGKGLEWV | -H2- |
| C | EVQLVESGGGLVQPGGSLRLSCAAS | -H1- | WVRQAPGKGLEWV | -H2- |
| D | EVQLVESGGGLVQPGGSLRLSCAAS | -H1- | WVRQAPGKGLEWV | -H2- |

FIG. 2A

|   |   |   |
|---|---|---|
| I | A RVTITADTSTSTAYMELSSLRSEDTAVYYCAR -H3- WGQGTLVTVSS | SEQ ID NO.: 40 |
|   | B RVTITADTSTSTAYMELSSLRSEDTAVYYCAR -H3- WGQGTLVTVSS | SEQ ID NO.: 41 |
|   | C RVTITADTSTSTAYMELSSLRSEDTAVYYCA -H3- WGQGTLVTVSS | SEQ ID NO.: 42 |
|   | D RVTITADTSTSTAYMELSSLRSEDTAVYYC -H3- WGQGTLVTVSS | SEQ ID NO.: 43 |
| II | A RVTISVDTSKNQFSLKLSSVTAADTAVYYCAR -H3- WGQGTLVTVSS | SEQ ID NO.: 44 |
|   | B RVTISVDTSKNQFSLKLSSVTAADTAVYYCAR -H3- WGQGTLVTVSS | SEQ ID NO.: 45 |
|   | C RVTISVDTSKNQFSLKLSSVTAADTAVYYCA -H3- WGQGTLVTVSS | SEQ ID NO.: 46 |
|   | D RVTISVDTSKNQFSLKLSSVTAADTAVYYC -H3- WGQGTLVTVSS | SEQ ID NO.: 47 |
| III | A RFTISRDNSKNTLYLQMNSLRAEDTAVYYCAR -H3- WGQGTLVTVSS | SEQ ID NO.: 48 |
|   | B RFTISRDNSKNTLYLQMNSLRAEDTAVYYCAR -H3- WGQGTLVTVSS | SEQ ID NO.: 49 |
|   | C RFTISRDNSKNTLYLQMNSLRAEDTAVYYCA -H3- WGQGTLVTVSS | SEQ ID NO.: 50 |
|   | D RFTISRDNSKNTLYLQMNSLRAEDTAVYYC -H3- WGQGTLVTVSS | SEQ ID NO.: 51 |
| Acceptor | A RFTISADTSKNTAYLQMNSLRAEDTAVYYCSR -H3- WGQGTLVTVSS | SEQ ID NO.: 52 |
|   | B RFTISADTSKNTAYLQMNSLRAEDTAVYYCSR -H3- WGQGTLVTVSS | SEQ ID NO.: 53 |
|   | C RFTISADTSKNTAYLQMNSLRAEDTAVYYCS -H3- WGQGTLVTVSS | SEQ ID NO.: 54 |
| Second Acceptor | A RFTISADTSKNTAYLQMNSLRAEDTAVYYCAR -H3- WGQGTLVTVSS | SEQ ID NO.: 55 |
|   | B RFTISADTSKNTAYLQMNSLRAEDTAVYYCAR -H3- WGQGTLVTVSS | SEQ ID NO.: 56 |
|   | C RFTISADTSKNTAYLQMNSLRAEDTAVYYCA -H3- WGQGTLVTVSS | SEQ ID NO.: 57 |
|   | D RFTISADTSKNTAYLQMNSLRAEDTAVYYC -H3- WGQGTLVTVSS | SEQ ID NO.: 58 |

FIG. 2B

Framework Sequences of huMAb4D5-8 Light Chain

LC-FR1  $^{1}$Asp Ile Gln Met Thr Gln Ser Pro Ser Ser Leu Ser Ala Ser Val Gly Asp Arg Val Thr Ile Thr Cys$^{23}$  (SEQ ID NO: 67)

LC-FR2  $^{35}$Trp Tyr Gln Gln Lys Pro Gly Lys Ala Pro Lys Leu Leu Ile Tyr$^{49}$ (SEQ ID NO: 68)

LC-FR3  $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 69)

LC-FR4  $^{98}$Phe Gly Gln Gly Thr Lys Val Glu Ile Lys$^{107}$ (SEQ ID NO: 70)

Framework Sequences of huMAb4D5-8 Heavy Chain

HC-FR1  $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 63)

HC-FR2  $^{36}$Trp Val Arg Gln Ala Pro Gly Lys Gly Leu Glu Trp Val$^{48}$ (SEQ ID NO: 64)

HC-FR3  $^{66}$Arg Phe Thr Ile Ser Ala Asp Thr Ser Lys Asn Thr Ala Tyr Leu Gln Met Asn$^{82a}$ Ser$^{82b}$ Leu$^{82c}$ Arg$^{83}$ Ala Glu Asp Thr Ala Val Tyr Tyr Cys$^{92}$ (SEQ ID NO: 65)

HC-FR4  $^{103}$Trp Gly Gln Gly Thr Leu Val Thr Val Ser Ser$^{113}$ (SEQ ID NO: 66)

*FIG. 4*

Framework Sequences of huMAb4D5-8 Light Chain Modified at Position 66 (Underlined)

LC-FR1  $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 67)

LC-FR2  $^{35}$Trp Tyr Gln Gln Lys Pro Gly Lys Ala Pro Lys Leu Leu Ile Tyr$^{49}$ (SEQ ID NO: 68)

LC-FR3  $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 89)

LC-FR4  $^{98}$Phe Gly Gln Gly Thr Lys Val Glu Ile Lys$^{107}$ (SEQ ID NO: 70)

Framework Sequences of huMAb4D5-8 Heavy Chain Modified at Postions 71, 73 and 78 (Underlined)

HC-FR1  $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 63)

HC-FR2  $^{36}$Trp Val Arg Gln Ala Pro Gly Lys Gly Leu Glu Trp Val$^{48}$ (SEQ ID NO: 64)

HC-FR3  $^{66}$Arg Phe Thr Ile Ser <u>Arg</u> Asp <u>Asn</u> Ser Lys Asn Thr <u>Leu</u> Tyr Leu Gln Met Asn$^{82a}$ Ser$^{82b}$ Leu$^{82c}$ Arg$^{83}$ Ala Glu Asp Thr Ala Val Tyr Tyr Cys$^{92}$ (SEQ ID NO: 90)

HC-FR4  $^{103}$Trp Gly Gln Gly Thr Leu Val Thr Val Ser Ser$^{113}$ (SEQ ID NO: 66)

*FIG. 5*

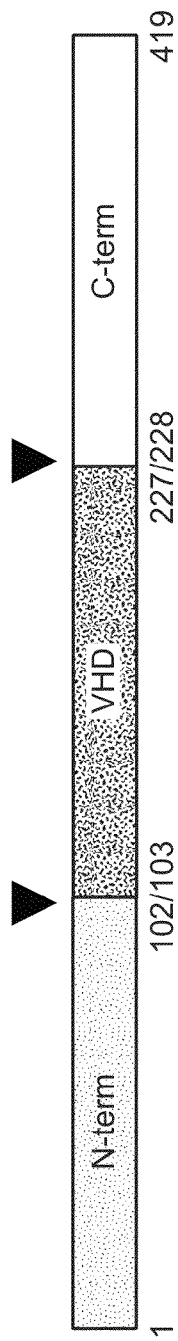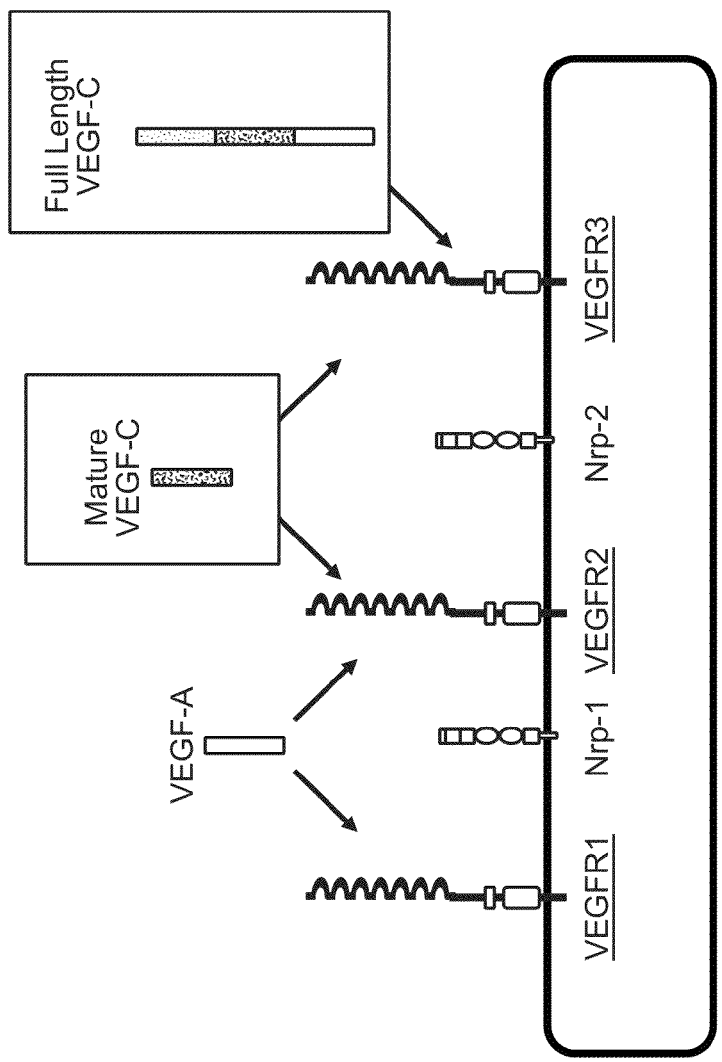
FIG. 6A
FIG. 6B

*P<0.05

*P<0.05

Control    Anti-VEGF-C

FIG. 23

| Kabat No. | CDR-L1 | | | | | | | | | | | CDR-L2 | | | | | | | CDR-L3 | | | | | | | | |
|---|---|---|---|---|---|---|---|---|---|---|---|---|---|---|---|---|---|---|---|---|---|---|---|---|---|---|---|
| | 24 | 25 | 26 | 27 | 28 | 29 | 30 | 31 | 32 | 33 | 34 | 50 | 51 | 52 | 53 | 54 | 55 | 56 | 89 | 90 | 91 | 92 | 93 | 94 | 95 | 96 | 97 |
| VC1 | R | A | S | Q | D | V | S | T | A | V | A | S | A | S | F | L | Y | S | Q | Q | S | Y | T | T | P | P | T |
| VC3 | R | A | S | Q | D | V | S | T | A | V | A | S | A | S | F | L | Y | S | Q | Q | S | Y | T | T | P | P | T |
| VC4 | R | A | S | Q | D | V | S | T | A | V | A | S | A | S | F | L | Y | S | Q | Q | S | Y | T | T | P | P | T |

FIG. 24

| Kabat No. | CDR-H1 | | | | | | | | | | CDR-H2 | | | | | | | | | | | | | | | | | |
|---|---|---|---|---|---|---|---|---|---|---|---|---|---|---|---|---|---|---|---|---|---|---|---|---|---|---|---|---|
| | 26 | 27 | 28 | 29 | 30 | 31 | 32 | 33 | 34 | 35 | 49 | 50 | 51 | 52 | 52a | 53 | 54 | 55 | 56 | 57 | 58 | 59 | 60 | 61 | 62 | 63 | 64 | 65 |
| VC1 | G | F | T | F | S | D | S | D | — | H | A | W | I | S | P | Y | S | G | Y | T | D | Y | A | D | S | V | K | G |
| VC3 | G | F | T | F | S | N | T | D | — | H | A | V | I | S | P | Y | S | G | Y | T | D | Y | A | D | S | V | K | G |
| VC4 | G | F | T | F | T | D | N | W | I | H | G | V | I | S | P | Y | S | G | A | T | Y | Y | A | D | S | V | K | G |

| Kabat No. | CDR-H3 | | | | | | | | | | | | | |
|---|---|---|---|---|---|---|---|---|---|---|---|---|---|---|
| | 93 | 94 | 95 | 96 | 97 | 98 | 99 | 100 | a | b | c | d | e | 101 | 102 |
| VC1 | A | R | L | F | E | V | I | F | — | — | — | — | — | D | Y |
| VC3 | A | R | W | R | D | Y | R | G | G | — | V | — | M | D | Y |
| VC4 | A | R | D | A | Y | Y | D | Y | A | G | W | A | F | D | Y |

FIG. 25

| Kabat No. | CDR-L1 | | | | | | | | | | | CDR-L2 | | | | | | | CDR-L3 | | | | | |
|---|---|---|---|---|---|---|---|---|---|---|---|---|---|---|---|---|---|---|---|---|---|---|---|---|
| | 24 | 25 | 26 | 27 | 28 | 29 | 30 | 31 | 32 | 33 | 34 | 50 | 51 | 52 | 53 | 54 | 55 | 56 | 89 | 90 | 91 | 92 | 93 | 94 | 95 | 96 | 97 |
| VC4 | R | A | S | Q | D | V | S | T | A | V | A | S | A | S | F | L | Y | S | Q | Q | S | Y | T | T | P | P | T |
| VC4.2 | R | A | S | Q | D | V | S | T | A | V | A | S | A | S | F | L | Y | S | Q | Q | S | Y | T | T | P | P | T |
| VC4.3 | R | A | S | Q | D | V | S | T | A | V | A | S | A | S | F | L | Y | S | Q | T | S | Y | R | – | P | Y | T |
| VC4.4 | R | A | S | Q | D | V | S | T | A | V | A | S | A | S | F | L | Y | S | Q | Q | S | Y | T | T | P | P | T |
| VC4.5 | R | A | S | Q | D | V | S | T | A | V | A | S | A | S | F | L | Y | S | Q | Q | S | Y | T | T | P | P | T |

*Note: Kabat No. row shows columns 24-34, 50-56, 89-97. The table header shows some columns 89, 90, 91, 92, 93, 94, 95, 96, 97.*

FIG. 26

| Kabat No. | CDR-H1 | | | | | | | | | | | CDR-H2 | | | | | | | | | | | | | | | |
|---|---|---|---|---|---|---|---|---|---|---|---|---|---|---|---|---|---|---|---|---|---|---|---|---|---|---|---|
| | 26 | 27 | 28 | 29 | 30 | 31 | 32 | 33 | 34 | 35 | | 49 | 50 | 51 | 52 | 52a | 53 | 54 | 55 | 56 | 57 | 58 | 59 | 60 | 61 | 62 | 63 | 64 | 65 |
| VC4 | G | F | T | F | D | D | N | W | – | H | | G | V | I | S | P | Y | S | G | A | T | Y | Y | A | D | S | V | K | G |
| VC4.2 | G | F | T | F | D | D | N | W | – | H | | G | V | I | S | P | Y | V | G | A | T | Y | Y | A | D | S | V | K | G |
| VC4.3 | G | F | T | F | D | Y | S | W | – | H | | G | F | I | S | P | G | S | G | Y | S | Y | Y | A | D | S | V | K | G |
| VC4.4 | G | F | T | F | D | D | N | W | – | H | | G | V | I | S | P | Y | S | G | A | T | Y | Y | A | D | S | V | K | G |
| VC4.5 | G | F | T | F | D | D | N | W | – | H | | G | V | I | S | P | Y | S | G | A | T | Y | Y | A | D | S | V | K | G |

| Kabat No. | CDR-H3 | | | | | | | | | | | | | |
|---|---|---|---|---|---|---|---|---|---|---|---|---|---|---|
| | 93 | 94 | 95 | 96 | 97 | 98 | 99 | 100 | a | b | c | d | e | 101 | 102 |
| VC4 | A | R | D | A | D | Y | D | Y | A | G | W | A | F | D | Y |
| VC4.2 | A | R | D | A | D | Y | A | Y | A | W | W | A | F | D | Y |
| VC4.3 | A | R | D | A | V | Y | D | Y | A | G | W | A | F | D | Y |
| VC4.4 | A | R | D | A | D | Y | Y | Y | A | W | W | A | L | D | Y |
| VC4.5 | A | R | D | A | D | Y | K | Y | A | F | W | A | F | D | Y |

FIG. 27

| Kabat No. | CDR-L1 | | | | | | | | | | | CDR-L2 | | | | | | | CDR-L3 | | | | | | | | |
|---|---|---|---|---|---|---|---|---|---|---|---|---|---|---|---|---|---|---|---|---|---|---|---|---|---|---|---|
| | 24 | 25 | 26 | 27 | 28 | 29 | 30 | 31 | 32 | 33 | 34 | 50 | 51 | 52 | 53 | 54 | 55 | 56 | 89 | 90 | 91 | 92 | 93 | 94 | 95 | 96 | 97 |
| VC1 | R | A | S | Q | D | V | S | T | A | V | A | S | A | S | F | L | Y | S | Q | Q | S | Y | T | T | P | P | T |
| VC1.1 | R | A | S | Q | D | V | S | T | A | V | A | S | A | S | F | L | Y | S | Q | Q | S | Y | T | T | P | P | T |
| VC1.2 | R | A | S | Q | D | V | S | T | A | V | A | S | A | S | F | L | Y | S | Q | Q | S | Y | T | T | P | P | T |
| VC1.3 | R | A | S | Q | D | V | S | T | A | V | A | S | A | S | F | L | Y | S | Q | Q | S | Y | T | T | P | P | T |
| VC1.4 | R | A | S | Q | D | V | S | T | A | V | A | S | A | S | F | L | Y | S | Q | Q | S | Y | T | T | P | P | T |
| VC1.5 | R | A | S | Q | D | V | S | T | A | V | A | S | A | S | F | L | Y | S | Q | Q | S | Y | T | T | P | P | T |
| VC1.6 | R | A | S | Q | D | V | S | T | A | V | A | S | A | S | F | L | Y | S | Q | Q | S | Y | T | T | P | P | T |
| VC1.7 | R | A | S | Q | D | V | S | T | A | V | A | S | A | S | F | L | Y | S | Q | Q | S | Y | T | T | P | P | T |
| VC1.8 | R | A | S | Q | D | V | S | T | A | V | A | S | A | S | F | L | Y | S | Q | Q | S | Y | T | T | P | P | T |
| VC1.9 | R | A | S | Q | D | V | S | T | A | V | A | S | A | S | F | L | Y | S | Q | Q | S | Y | T | T | P | P | T |
| VC1.10 | R | A | S | Q | D | V | S | T | A | V | A | S | A | S | F | L | Y | S | Q | Q | S | Y | T | T | P | P | T |
| VC1.11 | R | A | S | Q | D | V | S | T | A | V | A | S | A | S | F | L | Y | S | Q | Q | S | Y | T | T | P | P | T |
| VC1.12 | R | A | S | Q | D | V | S | T | A | V | A | S | A | S | F | L | Y | S | Q | Q | S | Y | T | T | P | P | T |

FIG. 29

| Kabat No. | CDR-L1 | | | | | | | | | | | CDR-L2 | | | | | | | CDR-L3 | | | | | | | | |
|---|---|---|---|---|---|---|---|---|---|---|---|---|---|---|---|---|---|---|---|---|---|---|---|---|---|---|---|
| | 24 | 25 | 26 | 27 | 28 | 29 | 30 | 31 | 32 | 33 | 34 | 50 | 51 | 52 | 53 | 54 | 55 | 56 | 89 | 90 | 91 | 92 | 93 | 94 | 95 | 96 | 97 |
| VC1.12 | R | A | S | Q | D | V | S | T | A | V | A | S | A | S | F | L | Y | S | Q | Q | S | Y | N | T | P | P | T |
| VC1.12.1 | R | A | S | Q | D | V | S | T | A | V | A | S | A | S | F | L | Y | S | Q | Q | S | Y | W | T | P | P | T |
| VC1.12.2 | R | A | S | Q | D | V | S | T | A | V | A | S | A | S | F | L | Y | S | Q | Q | S | Y | A | T | P | L | T |
| VC1.12.3 | R | A | S | Q | D | V | S | T | A | V | A | S | A | S | F | L | Y | S | Q | Q | T | Y | T | S | P | P | T |
| VC1.12.4 | R | A | S | Q | D | V | S | T | A | V | A | S | A | S | F | L | Y | S | Q | Q | S | Y | T | T | P | T | T |
| VC1.12.5 | R | A | S | Q | D | V | S | T | A | V | A | S | A | S | F | L | Y | S | Q | Q | S | Y | T | T | P | T | T |
| VC1.12.6 | R | A | S | Q | D | V | S | T | A | V | A | S | A | S | F | L | Y | S | Q | Q | S | Y | N | T | P | P | T |
| VC1.12.8 | R | A | S | Q | D | V | S | T | A | V | A | S | A | S | F | L | Y | S | Q | Q | S | Y | I | – | P | P | T |
| VC1.12.9 | R | A | S | Q | D | V | S | T | A | V | A | S | A | S | F | L | Y | S | Q | Q | S | Y | T | T | P | P | T |
| VC1.12.10 | R | A | S | Q | D | V | S | T | A | V | A | S | A | S | F | L | Y | S | Q | Q | S | Y | Y | S | P | L | T |

| Kabat No. | CDR-H1 |  |  |  |  |  |  |  |  |  | CDR-H2 |  |  |  |  |  |  |  |  |  |  |  |  |  |  |  |  |
|---|---|---|---|---|---|---|---|---|---|---|---|---|---|---|---|---|---|---|---|---|---|---|---|---|---|---|---|
|  | 26 | 27 | 28 | 29 | 30 | 31 | 32 | 33 | 34 | 35 | 49 | 50 | 51 | 52 | 52a | 53 | 54 | 55 | 56 | 57 | 58 | 59 | 60 | 61 | 62 | 63 | 64 | 65 |
| VC1.12  | G | F | T | F | S | D | S | D | I | H | A | W | I | S | P | Y | V | G | F | T | D | Y | A | D | S | V | K | G |
| VC1.12.1 | G | F | T | F | S | D | S | D | I | H | A | W | I | S | P | Y | V | G | F | T | D | Y | A | D | S | V | K | G |
| VC1.12.2 | G | F | T | F | S | D | S | D | I | H | A | W | I | S | P | Y | V | G | F | T | D | Y | A | D | S | V | K | G |
| VC1.12.3 | G | F | T | F | S | D | S | D | I | H | A | W | I | S | P | Y | V | G | F | T | D | Y | A | D | S | V | K | G |
| VC1.12.4 | G | F | T | F | S | D | S | D | I | H | A | W | I | S | P | Y | V | G | F | T | D | Y | A | D | S | V | K | G |
| VC1.12.5 | G | F | T | F | S | D | S | D | I | H | A | W | I | S | P | Y | V | G | F | T | D | Y | A | D | S | V | K | G |
| VC1.12.6 | G | F | T | F | S | D | S | D | I | H | A | W | I | S | P | Y | V | G | F | T | D | Y | A | D | S | V | K | G |
| VC1.12.8 | G | F | T | F | S | D | S | D | I | H | A | W | I | S | P | Y | V | G | F | T | D | Y | A | D | S | V | K | G |
| VC1.12.9 | G | F | T | F | S | D | S | D | I | H | A | W | I | S | P | Y | V | G | F | T | D | Y | A | D | S | V | K | G |
| VC1.12.10 | G | F | T | F | S | D | S | D | I | H | A | W | I | S | P | Y | V | G | F | T | D | Y | A | D | S | V | K | G |

| Kabat No. | CDR-H3 |  |  |  |  |  |  |  |  |  |  |  |  |  |  |
|---|---|---|---|---|---|---|---|---|---|---|---|---|---|---|---|
|  | 93 | 94 | 95 | 96 | 97 | 98 | 99 | 100 | a | b | c | d | e | 101 | 102 |
| VC1.12  | A | R | L | F | D | V | - | F | - | - | - | - | - | D | Y |
| VC1.12.1 | A | R | L | F | D | V | - | F | - | - | - | - | - | D | Y |
| VC1.12.2 | A | R | L | F | D | V | - | F | - | - | - | - | - | D | Y |
| VC1.12.3 | A | R | L | F | D | V | - | F | - | - | - | - | - | D | Y |
| VC1.12.4 | A | R | L | F | D | V | - | F | - | - | - | - | - | D | Y |
| VC1.12.5 | A | R | L | F | D | V | - | F | - | - | - | - | - | D | Y |
| VC1.12.6 | A | R | L | F | D | V | - | F | - | - | - | - | - | D | Y |
| VC1.12.8 | A | R | L | F | D | V | - | F | - | - | - | - | - | D | Y |
| VC1.12.9 | A | R | L | F | D | V | - | F | - | - | - | - | - | D | Y |
| VC1.12.10 | A | R | L | F | D | V | - | F | - | - | - | - | - | D | Y |

FIG. 31

| Clone | Phage IC$_{50}$ (nM) | hVEGF-C | | |
|---|---|---|---|---|
|  |  | Kon ($10^5$/Ms) | Koff ($10^{-4}$/s) | K$_D$ (nM) |
| VC1 | 38 | 10.7 | 1.89 | 0.17 |
| VC3 | 300 | 5.88 | 5.41 | 0.92 |
| VC4 | 32 | 2.71 | 2.63 | 0.97 |

|  | Phage IC$_{50}$ (nM) |
|---|---|
| VC4 | 32±4.9 |
| VC4.2 | 2.64±1.8 |
| VC4.3 | 2.72±1.5 |
| VC4.4 | 2.17±1.5 |
| VC4.5 | 1.7±0.8 |

| VC4.5Fab | Biacore(Fab) | | |
|---|---|---|---|
|  | Kon | Koff | Kd(nM) |
| R&D VEGF-C | 6.05E+04 | 1.67E-03 | 27.5 |
| VEGF-C C137S | 1.30E+05 | 1.04E-03 | 7.96 |

| VC4.5hIgG1 | Biacore (IgG1) | | |
|---|---|---|---|
|  | Kon | Koff | Kd(nM) |
| R&D VEGF-C | 4.64E+04 | 6.60E-03 | 140 |
| VEGF-C C137S | 1.09E+05 | 1.20E-04 | 1.1 |

|        | Phage IC$_{50}$ (nM) |
|--------|------------------|
| VC1    | 21.5±14          |
| VC1.1  | 41.5±5.5         |
| VC1.2  | 27.1±11.6        |
| VC1.3  | 22.1±12.2        |
| VC1.4  | 40.7±2.8         |
| VC1.5  | 28±20            |
| VC1.6  | 15.4±9.7         |
| VC1.7  | 20±11.6          |
| VC1.8  | 22.5±14          |
| VC1.9  | n/a              |
| VC1.10 | 17±10.2          |
| VC1.11 | 25.3±11.7        |
| VC1.12 | 5.1±2            |

|          | Phage IC$_{50}$ (nM) |
|----------|------------------|
| VC1.12   | 32.4±0.6         |
| VC1.12.1 | 7.29±0.9         |
| VC1.12.2 | 25.9±18.4        |
| VC1.12.3 | 23±8.7           |
| VC1.12.4 | 7.7±1.3          |
| VC1.12.5 | 28.1±16          |
| VC1.12.6 | 32.8±14          |
| VC1.12.8 | 13.7±4.3         |
| VC1.12.9 | 4.8±0.4          |
| VC1.12.10| 16.8±3.6         |
| VC4.5    | 5.4±0.5          |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| | | | | | | | | | | | | | | | | | | | | | | | | | | | | | | | | | | | Kabat - CDR L1 | | | | | | | |
| | | | | | | | | | | | | | | | | | | | | | | | | | | | | | | | | | | | Chothia - CDR L1 | | | | | | | |
| | | | | | | | | | | | | | | | | | | | | | | | | | | | | | | | | | | | | | Contact - CDR L1 | | | | | |
| VC4.5 | D | I | Q | M | T | Q | S | P | S | S | L | S | A | S | V | G | D | R | V | T | I | T | C | R | A | S | Q | | | | D | V | S | T | A | V | A | W | Y | Q |
| VC1.12 | D | I | Q | M | T | Q | S | P | S | S | L | S | A | S | V | G | D | R | V | T | I | T | C | R | A | S | Q | | | | D | V | S | T | A | V | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | Kabat - CDR L2 | | | | | | | | | | | | | | | | | | | | | | | | | | | | | | |
| | | | | | | | | | | | | Chothia - CDR L2 | | | | | | | | | | | | | | | | | | | | | | | | | | | | | | |
| | | | | | | | | | Contact - CDR L2 | | | | | | | | | | | | | | | | | | | | | | | | | | | | | | | | | |
| VC4.5 | Q | K | P | G | K | A | P | K | L | L | I | Y | S | A | S | F | L | Y | S | G | V | P | S | R | F | S | G | S | G | S | G | T | D | F | F | T | L | T | I | S | S | L | Q | P |
| VC1.12 | Q | K | P | G | K | A | P | K | L | L | I | Y | S | A | S | F | L | Y | S | G | V | P | S | R | F | S | G | S | G | S | G | T | D | F | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|
| | | | | | | | | | | Kabat - CDR L3 | | | | | | | | | | | | | | | | | | |
| | | | | | | | | | | Chothia - CDR L3 | | | | | | | | | | | | | | | | | | |
| | | | | | | | | | | Contact - CDR L3 | | | | | | | | | | | | | | | | | | |
| VC4.5 | E | D | F | A | T | Y | Y | C | Q | Q | S | Y | T | T | P | P | T | F | G | Q | G | T | K | V | E | I | K | R |
| VC1.12 | E | D | F | A | T | Y | Y | C | Q | Q | S | Y | T | T | P | P | T | F | G | Q | G | T | K | V | E | I | K | R |

*FIG. 38*

| Kabat# | 1 2 3 4 5 6 7 8 9 10 11 12 13 14 15 16 17 18 19 20 21 22 23 24 25 26 27 28 29 30 31 32 33 34 35 A 36 37 38 39 40 41 |
|---|---|
| | Kabat - CDR H1 |
| | Chothia - CDR H1 |
| | Contact - CDR H1 |
| VC4.5 | E V Q L V E S G G G L V Q P G G S L R L S C A A S G F T F S D N W I H W V R Q A P |
| VC1.12 | E V Q L V E S G G G L V Q P G G S L R L S C A A S G F T F S D D I H W V R Q A P |

| Kabat# | 42 43 44 45 46 47 48 49 50 51 52 52 52 52 53 54 55 56 57 58 59 60 61 62 63 64 65 66 67 68 69 70 71 72 73 74 75 76 77 78 79 |
|---|---|
| | Kabat - CDR H2 |
| | Chothia - CDR H2 |
| | Contact - CDR H2 |
| VC4.5 | G K G L E W V G V I S P   Y S G A T Y Y A D S V K G R F T I S A D T S K N T A Y |
| VC1.12 | G K G L E W V A W I S P   Y V G F T D Y A D S V K G R F T I S A D T S K N T A Y |

| Kabat# | 80 81 82 A B C 83 84 85 86 87 88 89 90 91 92 93 94 95 96 97 98 99 100 A B C D E 101 102 103 104 105 106 107 108 109 110 111 112 113 |
|---|---|
| | Kabat - CDR H3 |
| | Chothia - CDR H3 |
| | Contact - CDR H3 |
| VC4.5 | L Q M N S L R A E D T A V Y Y Y C A R D A D Y K Y A F W A F D Y W G Q G T L V T V S S |
| VC1.12 | L Q M N S L R A E D T A V Y Y Y C A R L F D V I         F D Y W G Q G T L V T V S S |

FIG. 39

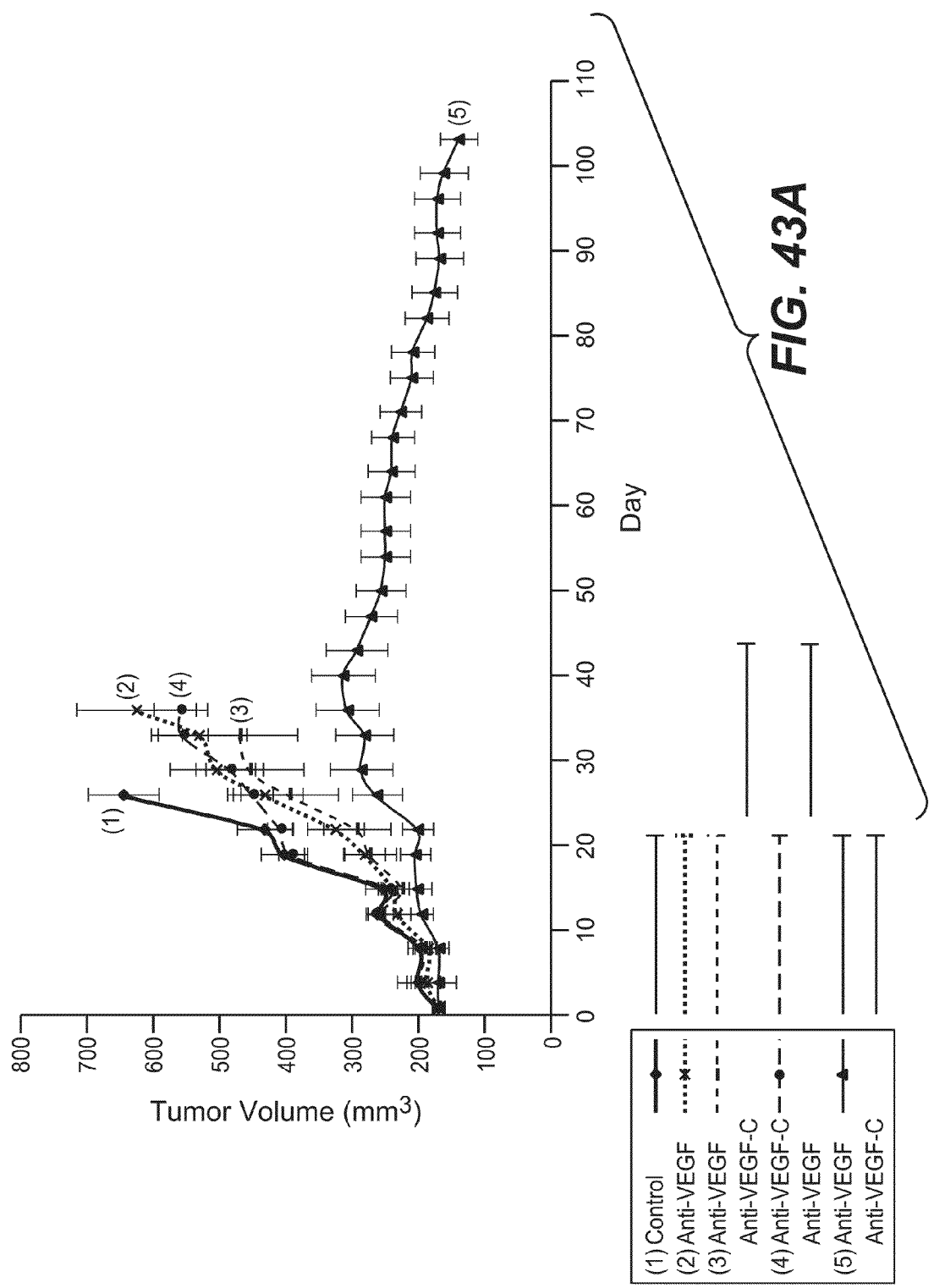

ANTI-VEGF-C ANTIBODIES AND METHODS USING SAME

RELATED APPLICATIONS

This application is a divisional application of U.S. application Ser. No. 12/882,330, filed Sep. 15, 2010, which claims benefit of priority under 35 USC 119(e) to provisional application No. 61/285,910 filed Dec. 11, 2009, and provisional application No. 61/284,753 filed Dec. 23, 2009, the entire contents of each of which are incorporated herein by reference

SEQUENCE LISTING

The instant application contains a Sequence Listing submitted via EFS-web and hereby incorporated by reference in its entirety. Said ASCII copy, created on Jun. 14, 2013, is named P4391R1D1_sequence_listing.txt, and is 55,396 bytes in size.

FIELD OF THE INVENTION

The present invention concerns VEGF-C antagonists, especially anti-VEGF-C antibodies, and their use in the prevention and treatment of tumor progression.

BACKGROUND

Development of a vascular system is a fundamental requirement for many physiological and pathological processes. Actively growing tissues such as embryos and tumors require adequate blood supply. They satisfy this need by producing pro-angiogenic factors, which promote new blood vessel formation via a process called angiogenesis. Vascular tube formation is a complex but orderly biological event involving all or many of the following steps: a) Endothelial cells (ECs) proliferate from existing ECs or differentiate from progenitor cells; b) ECs migrate and coalesce to form cord-like structures; c) vascular cords then undergo tubulogenesis to form vessels with a central lumen d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart. Hanahan, D. Science 277:48-50 (1997); Hogan, B. L. & Kolodziej, P. A. Nature Reviews Genetics. 3:513-23 (2002); Lubarsky, B. & Krasnow, M. A. Cell. 112:19-28 (2003).

It is well established that angiogenesis is implicated in the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.*, 267:10931-10934 (1992); Klagsbrun et al., *Annu. Rev. Physiol.* 53:217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710.

In the case of tumor growth, angiogenesis appears to be crucial for the transition from hyperplasia to neoplasia, and for providing nourishment for the growth and metastasis of the tumor. Folkman et al., *Nature* 339:58 (1989). The neovascularization allows the tumor cells to acquire a growth advantage and proliferative autonomy compared to the normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., *N. Engl. J. Med* 324:1-6 (1991); Horak et al., *Lancet* 340:1120-1124 (1992); Macchiarini et al., *Lancet* 340:145-146 (1992). The precise mechanisms that control the angiogenic switch is not well understood, but it is believed that neovascularization of tumor mass results from the net balance of a multitude of angiogenesis stimulators and inhibitors (Folkman *Nat Med* 1(1):27-31 (1995)).

It is currently accepted that metastases are responsible for the vast majority, estimated at 90%, of deaths from solid tumors (Gupta and Massague, *Cell* 127, 679-695 (2006)). The complex process of metastasis involves a series of distinct steps including detachment of tumor cells from the primary tumor, intravasation of tumor cells into lymphatic or blood vessels, and extravasation and growth of tumor cells in secondary sites. Analysis of regional lymph nodes in many tumor types suggests that the lymphatic vasculature is an important route for the dissemination of human cancers. Furthermore, in almost all carcinomas, the presence of tumor cells in lymph nodes is an important adverse prognostic factor. While it was previously thought that such metastases exclusively involved passage of malignant cells along pre-existing lymphatic vessels near tumors, recent experimental studies and clinico-pathological reports (reviewed in Achen et al., *Br J Cancer* 94 (2006), 1355-1360 and Nathanson, *Cancer* 98, 413-423 (2003)) suggest that lymphangiogenesis can be induced by solid tumors and can promote tumor spread. These and other recent studies suggest targeting lymphatics and lymphangiogenesis may be a useful therapeutic strategy to restrict the development of cancer metastasis, which would have a significant benefit for many patients.

Also, the concentration levels of VEGF in eye fluids are highly correlated to the presence of active proliferation of blood vessels in patients with diabetic and other ischemia-related retinopathies. Aiello et al., *N. Engl. J. Med.* 331:1480-1487 (1994). Furthermore, studies have demonstrated the localization of VEGF in choroidal neovascular membranes in patients affected by AMD. Lopez et al., *Invest. Ophthalmol. Vis. Sci.* 37:855-868 (1996).

In view of the role of angiogenesis and lymphangiogenesis in many diseases and disorders, it is desirable to have a means of modulating one or more of the biological effects causing these processes. It is clear that despite the significant advancement in the treatment of cancer achieved by angiogenesis inhibitors such as bevacizumab, improved therapies are still being sought, especially those that further enhance the overall efficacy. The invention described herein meets this need and provides other benefits.

SUMMARY OF THE INVENTION

The invention provides novel anti-VEGF-C antibodies and uses thereof. The present invention is based, at least in part, on experimental results obtained with anti-VEGF-C antibodies. Results obtained indicate that VEGF-C plays a role in angiogenesis as well as in modulating VEGF-C mediated lymphatic endothelial cell (LEC) migration and proliferation. In addition, the results demonstrate that blocking VEGF-C leads to an inhibition of lymphangiogenesis and a reduction in lymph node and distal organ metastasis. Accordingly, VEGF-C antagonist, such as VEGF-C antibodies of the invention, as described herein, provide important therapeutic and diagnostic agents for use in targeting pathological conditions associated with activation of VEGF-C receptors.

In one embodiment, an antibody that binds to VEGF-C or a fragment thereof is provided, wherein the antibody comprises at least one, two, three, four, five, or six HVRs selected from:
  (i) an HVR-L1 comprising the amino acid sequence of RASQDVSTAVA (SEQ ID NO:27);
  (ii) an HVR-L2 comprising the amino acid sequence of SASFLYS (SEQ ID NO:28);
  (iii) an HVR-L3 comprising the amino acid sequence of $QQX_1YX_2X_3PX_4T$ wherein the HVR-L3 comprises 1-4 (1, 2, 3, or 4) substitutions in any combination of the following positions: $X_1$ is S or T; $X_2$ is T, N, W, A, I, Y or R; $X_3$ is T, I or S; and/or $X_4$ is P, L, T or Y;
  (iv) an HVR-H1 comprising the amino acid sequence of $GFTFX_1X_2X_3X_4IH$ wherein the HVR-H1 comprises 1-4 (1, 2, 3, or 4) substitutions in any combination of the following positions: $X_1$ is S or T; $X_2$ is D, N or Y; $X_3$ is N, S, or T; and/or $X_4$ is D or W;
  (v) an HVR-H2 comprising the amino acid sequence of $X_1X_2ISPX_3X_4GX_5\ X_6X_7YADSVKG$ wherein the HVR-H2 comprises 1-7 (1, 2, 3, 4, 5, 6, or 7) substitutions in any combination of the following positions: $X_1$ is A or G; $X_2$ is F, V or W; $X_3$ is G, S or Y; $X_4$ is S or V; $X_5$ is A, F or Y; $X_6$ is S or T; and/or $X_7$ is D or Y; and
  (vi) an HVR-H3 comprising the amino acid sequence of $X_1RX_2X_3X_4X_5X_6X_7X_8X_9X_{10}X_{11}\ X_{12}DY$ wherein the HVR-H3 comprises 1-12 (1, 2, 3, 4, 5, 6, 7, 8, 9, 10, 11, or 12) substitutions in any combination of the following positions: $X_1$ is A, 5, T or V; $X_2$ is D, L or W; $X_3$ is A, F, R, V, W or Y; $X_4$ is D, E, G, K or T; $X_5$ is I, V or Y; $X_6$ is A, I, D, K, R or Y; $X_7$ is F or Y; $X_8$ is A, G or no amino acid at this position; $X_9$ is F, G, W or no amino acid at this position; $X_{10}$ is V, W or no amino acid at this position; $X_{11}$ is A or no amino acid at this position; and/or $X_{12}$ is F, L, M or no amino acid at this position. See FIGS. 1 and 23-30.

In another embodiment, an antibody that binds to VEGF-C or a fragment thereof is provided, wherein the antibody comprises at least one, two, three, four, five or six HVRs selected from:
  (1) an HVR-H1 comprising the amino acid sequence of SEQ ID NO:1;
  (2) an HVR-H2 comprising the amino acid sequence of SEQ ID NO:6;
  (3) an HVR-H3 comprising the amino acid sequence of SEQ ID NO:21;
  (4) an HVR-L1 comprising the amino acid sequence of SEQ ID NO:27;
  (5) an HVR-L2 comprising the amino acid sequence of SEQ ID NO:28; and
  (6) an HVR-L3 comprising the amino acid sequence of SEQ ID NO:29, 30, 31, 32, 33, 34, 35, 36, 37 or 38.

In another embodiment, an antibody that binds to VEGF-C or a fragment thereof is provided, wherein the antibody comprises a light chain comprising at least one, at least two, or all three variable light ("VL") HVR sequences selected from SEQ ID NOs:27, 28, and 29.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 30.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 31.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 32.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 33.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 34.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 35.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 36.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 37.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 38.

In another embodiment, an antibody that binds to VEGF-C or a fragment thereof is provided, wherein the antibody comprises a heavy chain comprising at least one, at least two, or all three variable heavy ("VH") HVR sequences selected from SEQ ID NOs:1, 6, and 21.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 29.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 30.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 31.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 32.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 33.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 34.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 35.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 36.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 37.

In another embodiment, an antibody that binds to VEGF-C or a fragment thereof is provided, wherein the antibody comprises a heavy chain comprising at least one, at least two, or all three VH HVR sequences selected from SEQ ID NOs:1, 6, and 21, and a light chain comprising at least one, at least two, or three VL HVR sequences selected from SEQ ID NOs:27, 28, and 38.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:29.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:30.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:31.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:32.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:33.

In another embodiment, an antibody that binds to VEGF-C or a fragment thereof is provided, wherein the antibody comprises:

(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:34.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:35.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:36.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:37.

In another embodiment, an antibody that binds to VEGF-C or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:6;
(3) an HVR-H3 comprising the amino acid sequence of SEQ ID NO:21;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:38.

In another embodiment, an antibody that binds to VEGF-C or a fragment thereof is provided, wherein the antibody comprises at least one, two, three, four, five or six HVRs selected from:
(1) an HVR-H1 comprising the amino acid sequence of SEQ ID NO:3 or 4;
(2) an HVR-H2 comprising the amino acid sequence of SEQ ID NO:8 or 91;
(3) an HVR-H3 comprising the amino acid sequence of SEQ ID NO:23, 24, 25 or 26:
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:29 or 39.

In another embodiment, an antibody that binds to VEGF-C or a fragment thereof is provided, wherein the antibody comprises a light chain comprising at least one, at least two, or all three VL HVR sequences selected from SEQ ID NOs:27, 28, and 29.

In another embodiment, an antibody that binds to VEGF-C or a fragment thereof is provided, wherein the antibody comprises a heavy chain comprising at least one, at least two, or all three VH HVR sequences selected from SEQ ID NOs:3, 8, and 26.

In another embodiment, an antibody that binds to VEGF-C or a fragment thereof is provided, wherein the antibody comprises a heavy chain comprising at least one, at least two, or all three VH HVR sequences selected from SEQ ID NOs:3, 8, and 26, and a light chain comprising at least one, at least two, or three VL HVR sequences selected from SEQ ID NOs:27, 28, and 29.

In another embodiment, an antibody that binds to VEGF-C or a fragment thereof is provided, wherein the antibody comprises:
(1) an HVR-H1 comprising the amino acid sequence of SEQ ID NO:3;
(2) an HVR-H2 comprising the amino acid sequence of SEQ ID NO:8;
(3) an HVR-H3 comprising the amino acid sequence of SEQ ID NO:26;
(4) an HVR-L1 comprising the amino acid sequence of SEQ ID NO:27;
(5) an HVR-L2 comprising the amino acid sequence of SEQ ID NO:28; and
(6) an HVR-L3 comprising the amino acid sequence of SEQ ID NO:29.

In another embodiment, an antibody that binds to VEGF-C or a fragment thereof is provided, wherein the anti-VEGF-C antibody comprises a heavy chain variable domain having at least 90% sequence identity to the amino acid sequence of SEQ ID NO:73.

In another embodiment, an antibody that binds to VEGF-C or a fragment thereof is provided, wherein the heavy chain variable domain comprises the amino acid sequence of SEQ ID NO:73.

In another embodiment, an antibody that binds to VEGF-C or a fragment thereof is provided, wherein the anti-VEGF-C antibody comprises a light chain variable domain having at least 90% sequence identity to the amino acid sequence of SEQ ID NO:74, 75, 76, 77, 78, 79, 80, 81, 82 or 83. In another embodiment, the anti-VEGF-C antibody comprises a light chain variable domain having at least 90% sequence identity to the amino acid sequence of SEQ ID NO:75, 78 or 82. In another embodiment, the anti-VEGF-C antibody comprises a light chain variable domain having at least 90% sequence identity to the amino acid sequence of SEQ ID NO:75. In another embodiment, the anti-VEGF-C antibody comprises a light chain variable domain having at least 90% sequence identity to the amino acid sequence of SEQ ID NO:78. In another embodiment, the anti-VEGF-C antibody comprises a light chain variable domain having at least 90% sequence identity to the amino acid sequence of SEQ ID NO:82.

In another embodiment, an antibody that binds to VEGF-C or a fragment thereof is provided, wherein the light chain variable domain comprises the amino acid sequence of SEQ ID NO:74, 75, 76, 77, 78, 79, 80, 81, 82 or 83. In another embodiment, the light chain variable domain comprises the amino acid sequence of SEQ ID NO:75, 78 or 82. In another embodiment, the light chain variable domain comprises the amino acid sequence of SEQ ID NO:75. In another embodiment, the light chain variable domain comprises the amino acid sequence of SEQ ID NO:78. In another embodiment, the light chain variable domain comprises the amino acid sequence of SEQ ID NO:82.

In another embodiment, an antibody that binds to VEGF-C or a fragment thereof is provided, wherein the anti-VEGF-C antibody comprises a heavy chain variable domain having at least 90% sequence identity to the amino acid sequence of SEQ ID NO:73, and a light chain variable domain having at least 90% sequence identity to the amino acid sequence of SEQ ID NO:74, 75, 76, 77, 78, 79, 80, 81, 82 or 83. In yet another embodiment, the anti-VEGF-C antibody comprises a heavy chain variable domain having at least 90% sequence identity to the amino acid sequence of SEQ ID NO:73, and a light chain variable domain having at least 90% sequence identity to the amino acid sequence of SEQ ID NO: 75, 78 or 82. In yet another embodiment, the anti-VEGF-C antibody comprises a heavy chain variable domain having at least 90% sequence identity to the amino acid sequence of SEQ ID NO:73, and a light chain variable domain having at least 90% sequence identity to the amino acid sequence of SEQ ID NO:75. In yet another embodiment, the anti-VEGF-C antibody comprises a heavy chain variable domain having at least 90% sequence identity to the amino acid sequence of SEQ ID NO:73, and a light chain variable domain having at least 90% sequence identity to the amino acid sequence of SEQ ID NO:78. In yet another embodiment, the anti-VEGF-C antibody comprises a heavy chain variable domain having at least 90% sequence identity to the amino acid sequence of SEQ ID NO:73, and a light chain variable domain having at least 90% sequence identity to the amino acid sequence of SEQ ID NO:82.

In another embodiment, an antibody that binds to VEGF-C or a fragment thereof is provided, wherein the anti-VEGF-C antibody comprises the heavy chain variable domain comprises the amino acid sequence of SEQ ID NO:73, and the light chain variable domain comprises the amino acid sequence of SEQ ID NO:74, 75, 76, 77, 78, 79, 80, 81, 82 or 83. In yet another embodiment, the anti-VEGF-C antibody comprises the heavy chain variable domain comprises the amino acid sequence of SEQ ID NO:73, and the light chain variable domain comprises the amino acid sequence of SEQ ID NO:75, 78 or 82. In yet another embodiment, the anti-VEGF-C antibody comprises the heavy chain variable domain comprises the amino acid sequence of SEQ ID NO:73, and the light chain variable domain comprises the amino acid sequence of SEQ ID NO:75. In yet another embodiment, the anti-VEGF-C antibody comprises the heavy chain variable domain comprises the amino acid sequence of SEQ ID NO:73, and the light chain variable domain comprises the amino acid sequence of SEQ ID NO:78. In yet another embodiment, the anti-VEGF-C antibody comprises the heavy chain variable domain comprises the amino acid sequence of SEQ ID NO:73, and the light chain variable domain comprises the amino acid sequence of SEQ ID NO:82.

In another embodiment, an antibody that binds to VEGF-C or a fragment thereof is provided, wherein the anti-VEGF-C antibody comprises a heavy chain variable domain having at least 90% sequence identity to the amino acid sequence of SEQ ID NO:84.

In another embodiment, an antibody that binds to VEGF-C or a fragment thereof is provided, wherein the anti-VEGF-C antibody comprises the heavy chain variable domain comprises the amino acid sequence of SEQ ID NO:84.

In another embodiment, an antibody that binds to VEGF-C or a fragment thereof is provided, wherein the anti-VEGF-C antibody comprises a light chain variable domain having at least 90% sequence identity to the amino acid sequence of SEQ ID NO:85.

In another embodiment, an antibody that binds to VEGF-C or a fragment thereof is provided, wherein the anti-VEGF-C antibody comprises the light chain variable domain comprises the amino acid sequence of SEQ ID NO:85.

In another embodiment, an antibody that binds to VEGF-C or a fragment thereof is provided, wherein the anti-VEGF-C antibody comprises a heavy chain variable domain having at least 90% sequence identity to the amino acid sequence of SEQ ID NO:84, and a light chain variable domain having at least 90% sequence identity to the amino acid sequence of SEQ ID NO:85.

In another embodiment, an antibody that binds to VEGF-C or a fragment thereof is provided, wherein the anti-VEGF-C antibody comprises the heavy chain variable domain comprises the amino acid sequence of SEQ ID NO:84, and the light chain variable domain comprises the amino acid sequence of SEQ ID NO:85.

In another embodiment, an antibody that binds to VEGF-C or a fragment thereof is provided, wherein the anti-VEGF-C antibody comprises the heavy chain variable domain comprises the amino acid sequence of SEQ ID NO:73, and the light chain variable domain comprises the amino acid sequence of SEQ ID NO:74.

In another embodiment, an antibody that binds to VEGF-C or a fragment thereof is provided, wherein the anti-VEGF-C antibody comprises the heavy chain variable domain comprises the amino acid sequence of SEQ ID NO:73, and the light chain variable domain comprises the amino acid sequence of SEQ ID NO:78.

In another embodiment, an antibody that binds to VEGF-C or a fragment thereof is provided, wherein the anti-VEGF-C antibody comprises the heavy chain variable domain comprises the amino acid sequence of SEQ ID NO:73, and the light chain variable domain comprises the amino acid sequence of SEQ ID NO:82.

In certain embodiments, an antibody that binds to VEGF-C or a fragment thereof is provided, wherein the antibody comprises an amino acid substitution at position 297 to alanine. In certain embodiments, the anti-VEGF-C antibodies described herein further comprise an amino acid substitution at position 265 to alanine. In certain embodiments, the anti-VEGF-C antibodies described herein further comprise amino acid substitutions at positions 265 to alanine and at position 297 to alanine.

In certain embodiments, the anti-VEGF-C antibody is a monoclonal antibody. In one embodiment, the antibody is an antibody fragment selected from a Fab, Fab'-SH, Fv, scFv, or (Fab')$_2$ fragment. In certain embodiments, the antibody is humanized. In certain embodiments, the antibody is human. In certain embodiments, at least a portion of the framework sequence is a human consensus framework sequence.

In certain embodiments, the anti-VEGF-C antibody is a bispecific antibody. In certain embodiments, the bispecific antibody binds VEGF-C and to another antigen. In certain embodiments, the bispecific antibody binds VEGF-C and VEGF. In certain embodiments, the bispecific antibody may bind to two different epitopes of VEGF-C. In certain embodiments, the bispecific antibody comprises a heavy chain variable domain comprising at one, two, or three variable heavy HVR sequences of the invention. In certain embodiments, the bispecific antibody comprises a heavy chain variable domain that binds to the same epitope on VEGF-C as the anti-VEGF-C antibodies of the invention.

In certain embodiments, the anti-VEGF-C antibody is selected from the group consisting of antibodies VC1, VC1.1, VC1.2, VC1.3, VC1.4, VC1.5, VC1.6, VC1.7, VC1.8, VC1.9, VC1.10, VC1.11, VC1.12, VC1.12.1, VC1.12.2, VC1.12.3, VC1.12.4, VC1.12.5, VC1.12.6, VC1.12.8, VC1.12.9, VC1.12.10, VC3, VC4, VC4.2, VC4.3, VC4.4, VC4.5, and fragments and variants, such as affinity matured variants thereof.

In certain embodiments, the invention concerns an anti-VEGF-C antibody comprising the heavy and/or light chain variable region sequence of an antibody selected from the group consisting of VC1, VC1.1, VC1.2, VC1.3, VC1.4, VC1.5, VC1.6, VC1.7, VC1.8, VC1.9, VC1.10, VC1.11, VC1.12, VC1.12.1, VC1.12.2, VC1.12.3, VC1.12.4, VC1.12.5, VC1.12.6, VC1.12.8, VC1.12.9, VC1.12.10, VC3, VC4, VC4.2, VC4.3, VC4.4, VC4.5, and fragments and variants thereof.

In certain embodiments, the invention concerns an anti-VEGF-C antibody comprising the heavy and/or light chain variable region sequences of VC1.12, VC1.12.1, VC1.12.2, VC1.12.3, VC1.12.4, VC1.12.5, VC1.12.6, VC1.12.8, VC1.12.9, VC1.12.10, VC4.5, or a fragment or variant thereof. In certain embodiments, the invention concerns an anti-VEGF-C antibody comprising the heavy and/or light chain variable region sequences of VC4.5, or a fragment or variant thereof. In certain embodiments, the invention concerns an anti-VEGF-C antibody comprising the heavy and/or light chain variable region sequences of VC1.12, or a fragment or variant thereof. In certain embodiments, the invention concerns an anti-VEGF-C antibody comprising the heavy and/or light chain variable region sequences of VC1.12.4, or a fragment or variant thereof. In certain embodiments, the invention concerns an anti-VEGF-C antibody comprising the heavy and/or light chain variable region sequences of VC1.12.9, or a fragment or variant thereof.

In one aspect, a polynucleotide encoding any of the above antibodies is provided. In one embodiment, a vector comprising the polynucleotide is provided. In one embodiment, a host cell comprising the vector is provided. In one embodiment, the host cell is eukaryotic. In one embodiment, the host cell is a CHO cell. In one embodiment, a method of making an anti-VEGF-C antibody is provided, wherein the method comprises culturing the host cell under conditions suitable for expression of the polynucleotide encoding the antibody, and isolating the antibody.

In one aspect, a method of detecting the presence of VEGF-C in a biological sample is provided, the method comprising contacting the biological sample with an antibody of the invention under conditions permissive for binding of the antibody to VEGF-C, and detecting whether a complex is formed between the antibody and VEGF-C. In one embodiment, the method comprises detecting VEGF-C-anti-VEGF-C antibody complex in a biological sample wherein the amino acid sequence of the anti-VEGF-C antibody comprises a heavy chain variable domain comprising the amino acid sequence of SEQ ID NO:73 or 84, and a light chain variable domain comprising the amino acid sequence of SEQ ID NO:74, 75, 76, 77, 78, 79, 80, 81, 82, 83 or 85. In yet another embodiment, the method comprises detecting VEGF-C-anti-VEGF-C antibody complex in a biological sample wherein the amino acid sequence of the anti-VEGF-C antibody comprises a heavy chain variable domain comprising the amino acid sequence of SEQ ID NO:73, and a light chain variable domain comprising the amino acid sequence of SEQ ID NO:75. In yet another embodiment, the method comprises detecting VEGF-C-anti-VEGF-C antibody complex in a biological sample wherein the amino acid sequence of the anti-VEGF-C antibody comprises a heavy chain variable domain comprising the amino acid sequence of SEQ ID NO:73, and a light chain variable domain comprising the amino acid sequence of SEQ ID NO:78. In yet another embodiment, the method comprises detecting VEGF-C-anti-VEGF-C antibody complex in a biological sample wherein the amino acid sequence of the anti-VEGF-C antibody comprises a heavy chain variable domain comprising the amino acid sequence of SEQ ID NO:73, and a light chain variable domain comprising the amino acid sequence of SEQ ID NO:82. In yet another embodiment, the method comprises detecting VEGF-C-anti-VEGF-C antibody complex in a biological sample wherein the amino acid sequence of the anti-VEGF-C antibody comprises a heavy chain variable domain comprising the amino acid sequence of SEQ ID NO:84, and a light chain variable domain comprising the amino acid sequence of SEQ ID NO:85.

In one aspect, a method for identifying a patient with a disorder associated with VEGF-C expression is provided, the method comprising contacting a biological sample from the patient having or suspected of having the disorder with an antibody of the invention and detecting VEGF-C-anti-VEGF-C antibody complex in the biological sample, wherein the detection of the VEGF-C-anti-VEGF-C antibody complex indicates that the patient has a disorder associated with VEGF-C expression. In certain embodiments, the amino acid sequence of the anti-VEGF-C antibody comprises a heavy chain variable domain comprising the amino acid sequence of SEQ ID NO:73 or 84, and a light chain variable domain comprising the amino acid sequence of SEQ ID NO: 74, 75, 76, 77, 78, 79, 80, 81, 82, 83 or 85. In one embodiment, the amino acid sequence of the anti-VEGF-C antibody comprises a heavy chain variable domain comprising the amino acid sequence of SEQ ID NO:73, and a light chain variable domain comprising the amino acid sequence of SEQ ID NO:75. In one embodiment, the amino acid sequence of the anti-VEGF-C antibody comprises a heavy chain variable domain comprising the amino acid sequence of SEQ ID NO:73, and a light chain variable domain comprising the amino acid sequence of SEQ ID NO:78. In one embodiment, the amino acid sequence of the anti-VEGF-C antibody comprises a heavy chain variable domain comprising the amino acid sequence of SEQ ID NO:73, and a light chain variable domain comprising the amino acid sequence of SEQ ID NO:82. In one embodiment, the amino acid sequence of the anti- VEGF-C antibody comprises a heavy chain variable domain comprising the amino acid sequence of SEQ ID NO:84, and a light chain variable domain comprising the amino acid sequence of SEQ ID NO:85. In yet another embodiment, the anti-VEGF-C antibody is detectably labeled.

The invention further provides immunoconjugates comprising an antibody conjugated to an agent, such as a drug or cytotoxic agent.

In certain embodiments, methods for inhibiting angiogenesis comprising administering to a subject an effective amount of any of the anti-VEGF-C antibodies described herein are provided. In certain embodiments, methods for inhibiting lymphatic endothelial cell migration comprising administering to a subject an effective amount of any of the anti-VEGF-C antibodies described herein are provided. In certain embodiments, methods for inhibiting lymphatic endothelial cell proliferation comprising administering to a subject an effective amount of any of the anti-VEGF-C antibodies described herein are provided. In certain embodiments, methods for inhibiting vascular permeability comprising administering to a subject an effective amount of any of the anti-VEGF-C antibodies described herein are provided. In certain embodiments, methods for inhibiting tumoral lymphangiogenesis comprising administering to a subject an effective amount of any of the anti-VEGF-C antibodies described herein are provided. In certain embodiments, methods for inhibiting tumor metastasis comprising administering to a subject an effective amount of any of the anti-VEGF-C antibodies described herein are provided. In certain embodiments, methods for treating a tumor, cancer, or cell proliferative disorder comprising administering to a subject an effective amount of any of the anti-VEGF-C antibodies described herein are provided. In certain embodiments, the methods further comprise administering to the subject an effective amount of an anti-angiogenic agent. In one embodiment, the anti-angiogenic agent is a VEGF antagonist. In one embodiment, the VEGF antagonist is an anti-VEGF antibody. In one embodiment, the anti-VEGF antibody is bevacizumab.

In one embodiment, methods for inhibiting angiogenesis comprising administering to a subject an effective amount of any of the anti-VEGF-C antibodies described herein and an effective amount of an anti-angiogenic agent are provided. In another embodiment, methods for inhibiting lymphatic endothelial cell migration comprising administering to a subject an effective amount of any of the anti-VEGF-C antibodies described herein and an effective amount of an anti-angiogenic agent are provided. In another embodiment, methods for inhibiting lymphatic endothelial cell proliferation comprising administering to a subject an effective amount of any of the anti-VEGF-C antibodies described herein and an effective amount of an anti-angiogenic agent are provided. In another embodiment, methods for inhibiting vascular permeability comprising administering to a subject an effective amount of any of the anti-VEGF-C antibodies described herein and an effective amount of an anti-angiogenic agent are provided. In yet another embodiment, methods for inhibiting tumoral lymphangiogenesis comprising administering to a subject an effective amount of any of the anti-VEGF-C antibodies described herein and an effective amount of an anti-angiogenic agent are provided. In another embodiment, methods for inhibiting tumor metastasis comprising administering to a subject an effective amount of any of the anti-VEGF-C antibodies described herein and an effective amount of an anti-angiogenic agent are provided. In another embodiment, methods for treating a tumor, cancer, or cell proliferative disorder comprising administering to a subject an effective amount of any of the anti-VEGF-C antibodies described herein and an effective amount of an anti-angiogenic agent are provided.

In certain embodiments, the subject is a human patient, such as a human cancer patient, who may have been diagnosed or may be at risk of developing metastasis. In certain embodiments, the subject is relapsed from or refractory to a VEGF antagonist.

In certain embodiments, the cancer is selected from the group consisting of carcinoma, lymphoma, blastoma, sarcoma, and leukemia.

In certain embodiments, the cancer is selected from the group consisting of squamous cell cancer, small-cell lung cancer, non-small cell lung cancer, adenocarcinoma of the lung, squamous carcinoma of the lung, cancer of the peritoneum, hepatocellular cancer, gastric cancer, gastrointestinal cancer, gastrointestinal stromal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, melanoma, superficial spreading melanoma, lentigo maligna melanoma, acral lentiginous melanomas, nodular melanomas, B-cell lymphoma, chronic lymphocytic leukemia (CLL); acute lymphoblastic leukemia (ALL); Hairy cell leukemia; chronic myeloblastic leukemia; post-transplant lymphoproliferative disorder (PTLD), abnormal vascular proliferation associated with phakomatoses, edema associated with brain tumors, and Meigs' syndrome.

In certain embodiments, the cancer is non-small cell lung cancer, renal cancer, glioblastoma, breast cancer, ovarian cancer, colon cancer or colorectal cancer.

In certain embodiments, B-cell lymphoma is selected from the group consisting of low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia.

In one embodiment, a method of enhancing efficacy of an anti-angiogenic agent in a subject having a pathological condition associated with angiogenesis, comprising administering to the subject an effective amount of any of the antibodies above in addition to the anti-antigenic agent, thereby enhancing said anti-angiogenic agent's efficacy is provided. In one embodiment, the subject is human. In one embodiment, the pathological condition associated with angiogenesis is a tumor, a cancer, and/or a cell proliferative disorder. In one embodiment, the pathological condition associated with angiogenesis is an intraocular neovascular disease. In one embodiment, the anti-angiogenic agent is a VEGF antagonist. In one embodiment, the VEGF antagonist is an anti-VEGF antibody. In one embodiment, the anti-VEGF antibody is bevacizumab.

In another aspect, the invention further concerns a composition comprising any of the anti-VEGF-C antibodies above in admixture with a pharmaceutically acceptable carrier.

In certain embodiments, the invention concerns a pharmaceutical composition for the prevention or treatment of tumor metastasis comprising an effective amount of any of the anti-VEGF-C antibodies described herein in admixture with a pharmaceutically acceptable carrier.

In certain embodiments, methods of treating cancer are provided, wherein the method comprises administering to the subject the pharmaceutical composition comprising any of the anti-VEGF-C antibodies described herein. In certain embodiments, the methods further comprise administering to the subject an effective amount of anti-VEGF antibody. An exemplary and non-limiting list of cancers contemplated is provided herein under "Definitions."

In certain embodiments, methods for treating a tumor, cancer or cell proliferative disorder in a subject refractory to or relapsed from a VEGF antagonist therapy comprising the step of administering to the subject any of the anti-VEGF-C antibodies described herein alone or in combination with VEGF antagonist are provided. In certain embodiments, subjects are previously treated with anti-VEGF antibody. In certain embodiments, the tumors are non-responsive or refractory to anti-VEGF antibody therapy.

In certain embodiments, the invention concerns anti-VEGF-C antibodies described herein for use in the prevention or treatment of tumor metastasis.

In certain embodiments, methods of preventing recurrence of cancer in a subject comprising administering to the subject any of the anti-VEGF-C antibodies described herein, wherein the administering prevents cancer recurrence in the subject are provided. In certain embodiments, methods of reducing the likelihood of cancer recurrence in a subject comprising administering to the subject any of the anti-VEGF-C antibodies described herein, wherein the administering reduces the likelihood of cancer recurrence in the subject are provided. In certain embodiments, the administering of any of the anti-VEGF-C antibodies described herein prevents or reduces the likelihood of reoccurrence of a clinically detectable tumor, or metastasis thereof. In certain embodiments, methods of preventing the regrowth of a tumor in a subject comprising the steps of removing the tumor and thereafter administering to the subject any of the anti-VEGF-C antibodies described herein are provided. In certain embodiments, methods of preventing the recurrence of cancer in a subject having a tumor comprising the steps of removing the tumor and thereafter administering to the subject any of the anti-VEGF-C antibodies described herein are provided.

In certain embodiments, the amino acid sequence of the anti-VEGF-C antibody comprises a heavy chain variable domain comprising the amino acid sequence of SEQ ID NO:73 or 84, and a light chain variable domain comprising the amino acid sequence of SEQ ID NO: 74, 75, 76, 77, 78, 79, 80, 81, 82, 83 or 85. In yet another embodiment, the amino acid sequence of the anti-VEGF-C antibody comprises a heavy chain variable domain comprising the amino acid sequence of SEQ ID NO:73, and a light chain variable domain comprising the amino acid sequence of SEQ ID NO:75. In yet another embodiment, the amino acid sequence of the anti-VEGF-C antibody comprises a heavy chain variable domain comprising the amino acid sequence of SEQ ID NO:73, and a light chain variable domain comprising the amino acid sequence of SEQ ID NO:78. In yet another embodiment, the amino acid sequence of the anti-VEGF-C antibody comprises a heavy chain variable domain comprising the amino acid sequence of SEQ ID NO:73, and a light chain variable domain comprising the amino acid sequence of SEQ ID NO:82. In yet another embodiment, the amino acid sequence of the anti-VEGF-C antibody comprises a heavy chain variable domain comprising the amino acid sequence of SEQ ID NO:84, and a light chain variable domain comprising the amino acid sequence of SEQ ID NO:85.

In certain embodiments, the anti-VEGF-C antibodies described herein blocks biological activity of VEGF-C. In certain embodiments, the VEGF-C is the full-length VEGF-C. In another embodiment, the VEGF-C is the mature VEGF-C.

In certain embodiments, the methods described above further comprise administering to the subject an effective amount of an anti-angiogenic agent. In certain embodiments, the anti-angiogenic agent is a VEGF antagonist. In certain embodiments, the VEGF antagonist is an anti-VEGF antibody. In certain embodiments, the anti-VEGF antibody is bevacizumab.

In certain embodiments, any of the methods described above further comprises administering to the subject an effective amount of a chemotherapeutic agent. An exemplary and non-limiting list of chemotherapeutic agents contemplated is provided herein under "Definitions." In certain embodiments, the chemotherapeutic agent is selected from the group consisting of paclitaxel, carboplatin, cisplatin, gemcitabine and pemetrexed.

In certain embodiments, anti-VEGF antibody is administered first to the subject and then anti-VEGF-C antibody is administered to the subject. In certain embodiments, anti-VEGF-C antibody and anti-VEGF antibody are administered simultaneously to the subject. In certain embodiments, anti-VEGF-C antibody, anti-VEGF antibody and chemotherapeutic agent are administered simultaneously to the subject.

Any embodiment described herein or any combination thereof applies to any and all anti-VEGF-C antibodies and methods of the invention described herein.

BRIEF DESCRIPTION OF THE DRAWINGS

FIG. 1A-F: Heavy chain and light chain HVR loop sequences of anti-VEGF-C antibodies. FIGS. 1A, 1B and 1C show the heavy chain HVR sequences, H1, H2, and H3, respectively, and FIGS. 1D, 1E and 1F show light chain HVR sequences, L1, L2 and L3, respectively. Sequence numbering is as follows: clone VC1 (HVR-H1 is SEQ ID NO:1; HVR-H2 is SEQ ID NO:5; HVR-H3 is SEQ ID NO:9; HVR-L1 is SEQ ID NO:27; HVR-L2 is SEQ ID NO:28; HVR-L3 is SEQ ID NO:29); clone VC1.1 (HVR-H1 is SEQ ID NO:1; HVR-H2 is SEQ ID NO:5; HVR-H3 is SEQ ID NO:10; HVR-L1 is SEQ ID NO:27; HVR-L2 is SEQ ID NO:28; HVR-L3 is SEQ ID NO:29); clone VC1.2 (HVR-H1 is SEQ ID NO:1; HVR-H2 is SEQ ID NO:5; HVR-H3 is SEQ ID NO:11; HVR-L1 is SEQ ID NO:27; HVR-L2 is SEQ ID NO:28; HVR-L3 is SEQ ID NO:29); clone VC1.3 (HVR-H1 is SEQ ID NO:1; HVR-H2 is SEQ ID NO:5; HVR-H3 is SEQ ID NO:12; HVR-L1 is SEQ ID NO:27; HVR-L2 is SEQ ID NO:28; HVR-L3 is SEQ ID NO:29); clone VC1.4 (HVR-H1 is SEQ ID NO:1; HVR-H2 is SEQ ID NO:5; HVR-H3 is SEQ ID NO:13; HVR-L1 is SEQ ID NO:27; HVR-L2 is SEQ ID NO:28; HVR-L3 is SEQ ID NO:29); clone VC1.5 (HVR-H1 is SEQ ID NO:1; HVR-H2 is SEQ ID NO:5; HVR-H3 is SEQ ID NO:14; HVR-L1 is SEQ ID NO:27; HVR-L2 is SEQ ID NO:28; HVR-L3 is SEQ ID NO:29); clone VC1.6 (HVR-H1 is SEQ ID NO:1; HVR-H2 is SEQ ID NO:5; HVR-H3 is SEQ ID NO:15; HVR-L1 is SEQ ID NO:27; HVR-L2 is SEQ ID NO:28; HVR-L3 is SEQ ID NO:29); clone VC1.7 (HVR-H1 is SEQ ID NO:1; HVR-H2 is SEQ ID NO:5; HVR-H3 is SEQ ID NO:16; HVR-L1 is SEQ ID NO:27; HVR-L2 is SEQ ID NO:28; HVR-L3 is SEQ ID NO:29); clone VC1.8 (HVR-H1 is SEQ ID NO:1; HVR-H2 is SEQ ID NO:5; HVR-H3 is SEQ ID NO:17; HVR-L1 is SEQ ID NO:27; HVR-L2 is SEQ ID NO:28; HVR-L3 is SEQ ID NO:29); clone VC1.9 (HVR-H1 is SEQ ID NO:1; HVR-H2 is SEQ ID NO:5; HVR-H3 is SEQ ID NO:18; HVR-L1 is SEQ ID NO:27; HVR-L2 is SEQ ID NO:28; HVR-L3 is SEQ ID NO:29); clone VC1.10 (HVR-H1 is SEQ ID NO:1; HVR- H2 is SEQ ID NO:5; HVR-H3 is SEQ ID NO:19; HVR-L1 is SEQ ID NO:27; HVR-L2 is SEQ ID NO:28; HVR-L3 is SEQ ID NO:29); clone VC1.11 (HVR-H1 is SEQ ID NO:1; HVR-H2 is SEQ ID NO:5; HVR-H3 is SEQ ID NO:20; HVR-L1 is SEQ ID NO:27; HVR-L2 is SEQ ID NO:28; HVR-L3 is SEQ ID NO:29); clone VC1.12 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:29); clone VC1.12.1 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:30); clone VC1.12.2 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:31); clone VC1.12.3 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:32); clone VC1.12.4 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:33); clone VC1.12.5 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:34); clone VC1.12.6 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:35); VC1.12.8 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:36); clone VC1.12.9 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:37); clone VC1.12.10 (HVR-H1 is SEQ ID NO:1; HVR-H2 is SEQ ID NO:6; HVR-H3 is SEQ ID NO:21; HVR-L1 is SEQ ID NO:27; HVR-L2 is SEQ ID NO:28; HVR-L3 is SEQ ID NO:38); clone VC3 (HVR-H1 is SEQ ID NO:2; HVR-H2 is SEQ ID NO:7; HVR-H3 is SEQ ID NO:22; HVR-L1 is SEQ ID NO:27; HVR-L2 is SEQ ID NO:28; HVR-L3 is SEQ ID NO:29); clone VC4 (HVR-H1 is SEQ ID NO:3; HVR-H2 is SEQ ID NO:8; HVR-H3 is SEQ ID NO:23; HVR-L1 is SEQ ID NO:27; HVR-L2 is SEQ ID NO:28; HVR-L3 is SEQ ID NO:29); clone VC4.2 (HVR-H1 is SEQ ID NO:3; HVR-H2 is SEQ ID NO:8; HVR-H3 is SEQ ID NO:24; HVR-L1 is SEQ ID NO:27; HVR-L2 is SEQ ID NO:28; HVR-L3 is SEQ ID NO:29); clone VC4.3 (HVR-H1 is SEQ ID NO:4; HVR-H2 is SEQ ID NO:91; HVR-H3 is SEQ ID NO:23; HVR-L1 is SEQ ID NO:27; HVR-L2 is SEQ ID NO:28; HVR-L3 is SEQ ID NO:39); clone VC4.4 (HVR-H1 is SEQ ID NO:3; HVR-H2 is SEQ ID NO:8; HVR-H3 is SEQ ID NO:25; HVR-L1 is SEQ ID NO:27; HVR-L2 is SEQ ID NO:28; HVR-L3 is SEQ ID NO:29); and clone VC4.5 (HVR-H1 is SEQ ID NO:3; HVR-H2 is SEQ ID NO:8; HVR-H3 is SEQ ID NO:26; HVR-L1 is SEQ ID NO:27; HVR-L2 is SEQ ID NO:28; HVR-L3 is SEQ ID NO:29).

Amino acid positions are numbered according to the Kabat numbering system as described below.

FIGS. 2A & 2B depict exemplary acceptor human consensus framework sequences for use in practicing the instant invention with sequence identifiers as follows:
Variable heavy (VH) consensus frameworks
FIG. 2A shows human VH subgroup I consensus framework minus Kabat CDRs (SEQ ID NO:40)
human VH subgroup I consensus framework minus extended hypervariable regions (SEQ ID NOs:41-43)
human VH subgroup II consensus framework minus Kabat CDRs (SEQ ID NO:44)
human VH subgroup II consensus framework minus extended hypervariable regions (SEQ ID NOs:45-47)
human VH subgroup II consensus framework minus extended
FIG. 2B shows human VH subgroup III consensus framework minus Kabat CDRs (SEQ ID NO:48)
human VH subgroup III consensus framework minus extended hypervariable regions (SEQ ID NOs:49-51)
human VH acceptor framework minus Kabat CDRs (SEQ ID NO:52)
human VH acceptor framework minus extended hypervariable regions (SEQ ID NOs:53-54)
human VH acceptor 2 framework minus Kabat CDRs (SEQ ID NO:55)
human VH acceptor 2 framework minus extended hypervariable regions (SEQ ID NOs:56-58)

Amino acid positions are numbered according to the Kabat numbering system as described below.

Figure 3:
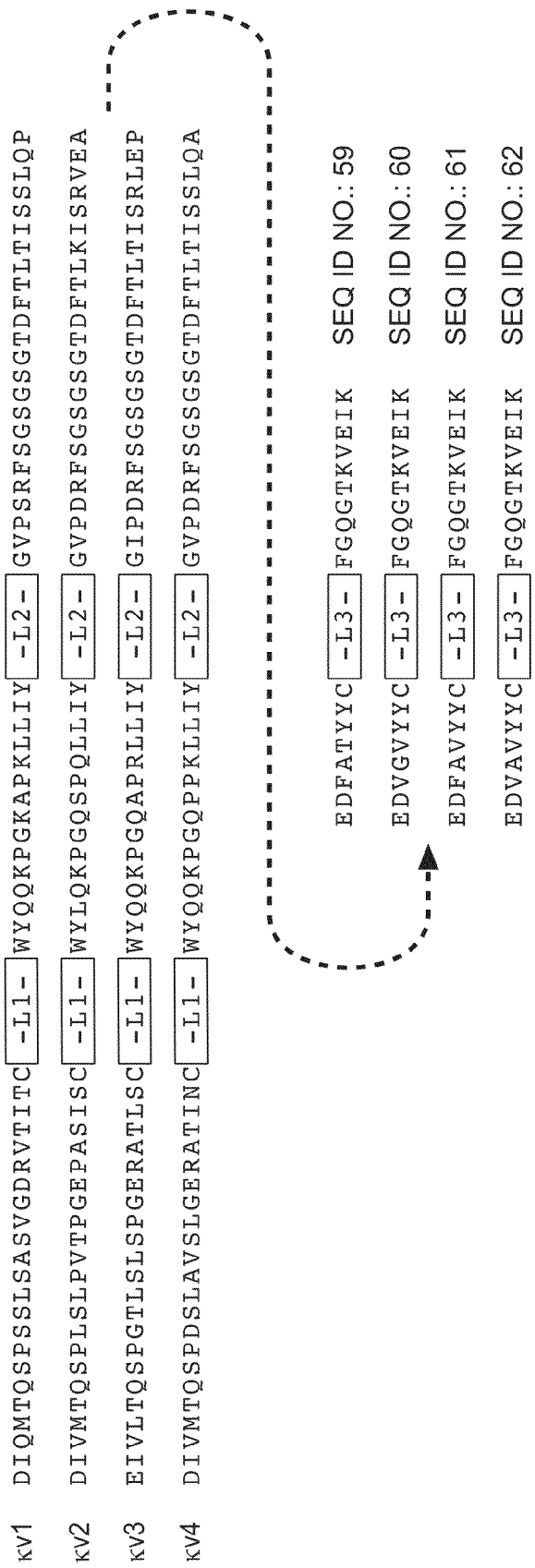

FIG. 3 depicts exemplary acceptor human consensus framework sequences for use in practicing the instant invention with sequence identifiers as follows:
Variable light (VL) consensus frameworks
human VL kappa subgroup I consensus framework (SEQ ID NO:59)
human VL kappa subgroup II consensus framework (SEQ ID NO:60)
human VL kappa subgroup III consensus framework (SEQ ID NO:61) human VL kappa subgroup IV consensus framework (SEQ ID NO:62)

FIG. 4 depicts framework region sequences of huMAb4D5-8 heavy and light chains. Numbers in superscript/bold indicate amino acid positions according to Kabat.

FIG. 5 depicts modified/variant framework region sequences of huMAb4D5-8 heavy and light chains. Numbers in superscript/bold indicate amino acid positions according to Kabat.

Figure 7A:
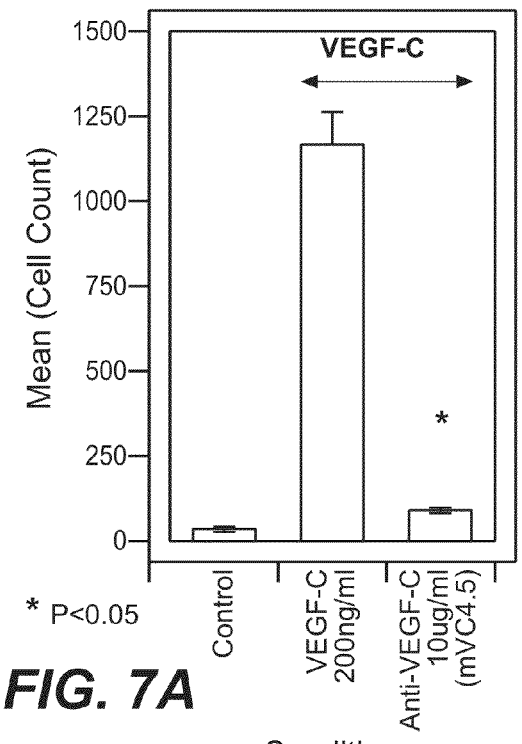
Figure 7B:
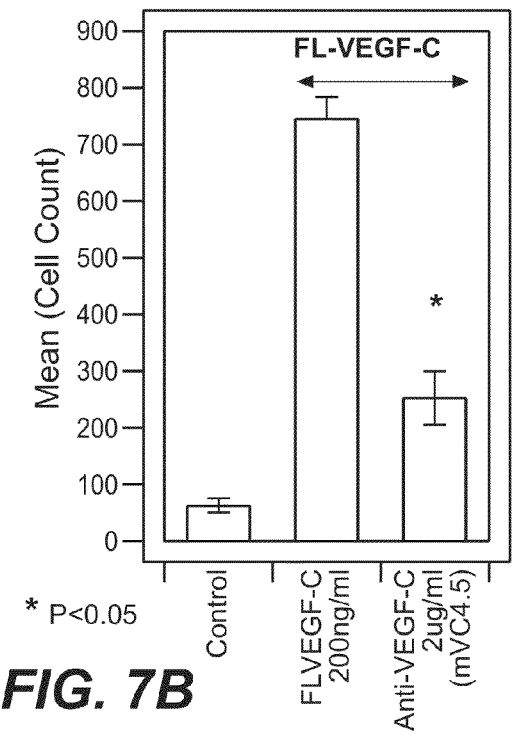

FIGS. 6A & 6B: A. Schematic of VEGF-C including VEGF homology domain (VHD). B. Receptor ligand interactions of the VEGF family of growth factors FIGS. 7A & 7B: Anti-VEGF-C antibody reduces VEGF-C-induced cellular migration in vitro. A. LECs migrating in response to 200 ng/ml of mature VEGF-C(R&D Systems) for 18 hours in the presence or absence of anti-VEGF-C (10 µg/ml) (n=6 for each condition). B. LECs migrating in response to 200 ng/ml of full-length VEGF-C for 18 hours in the presence or absence of anti-VEGF-C (10 µg/ml) (n=6 for each condition). Error bars represent SEM. *=p<0.05.

Figure 8A:
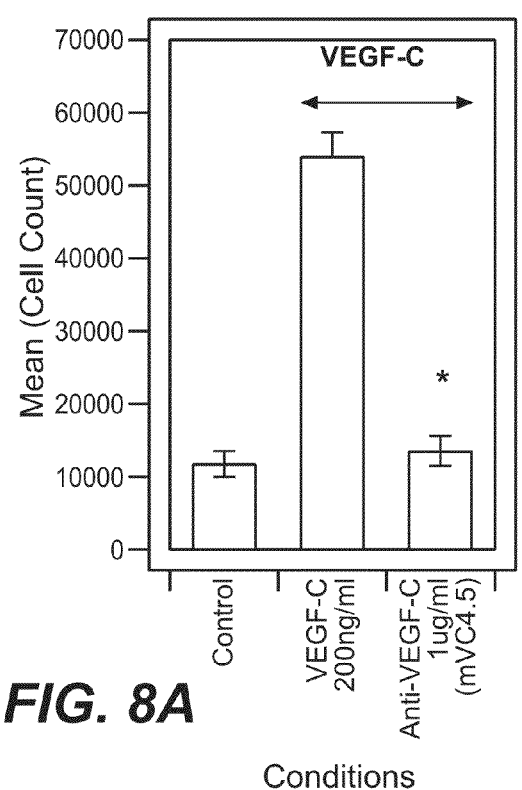
Figure 8B:
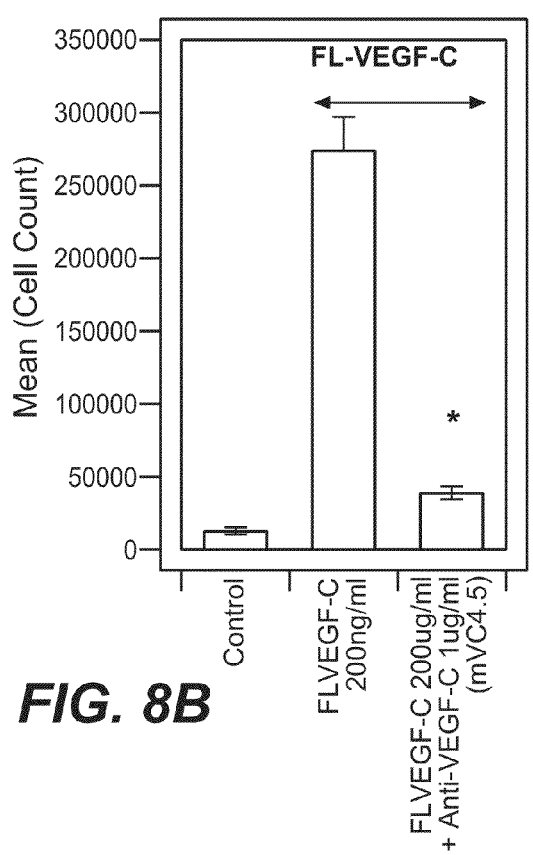

FIGS. 8A & 8B: Anti-VEGF-C antibody reduces VEGF-C-induced cellular proliferation in vitro. A. LECs proliferation in response to 200 ng/ml of mature VEGF-C(R&D Systems) in the presence or absence of anti-VEGF-C (1 µg/ml) (n=6 for each condition). B. LECs proliferation in response to 200 ng/ml of full-length VEGF-C in the presence or absence of anti-VEGF-C antibody (1 µg/ml) (n=6 for each condition). Error bars represent SEM. *=p<0.05.

Figure 9:
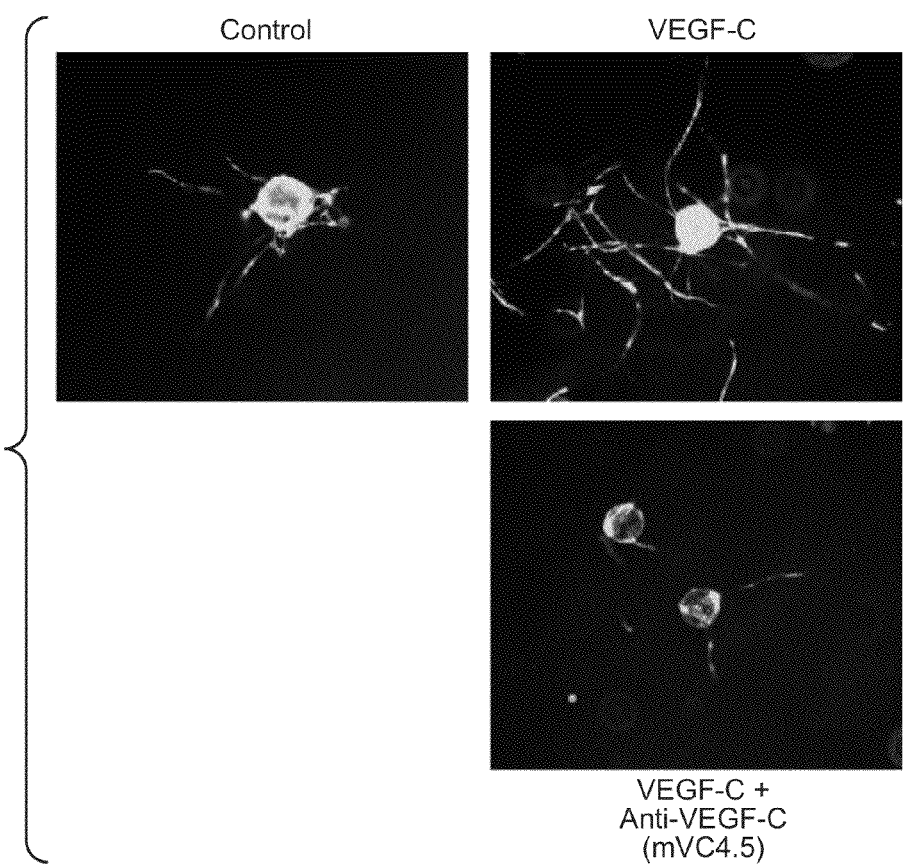

FIG. 9: Anti-VEGF-C antibody reduces VEGF-C-induced sprouting in vitro. LECs sprouting in a bead sprouting assay in response to 200 ng/ml of mature VEGF-C(R&D Systems) for 14 days in the presence or absence of anti-VEGF-C antibody (10 µg/ml). Cultures were stained with anti-LYVE-1 antibody to visualize LECs (representative images shown).

Figure 10:
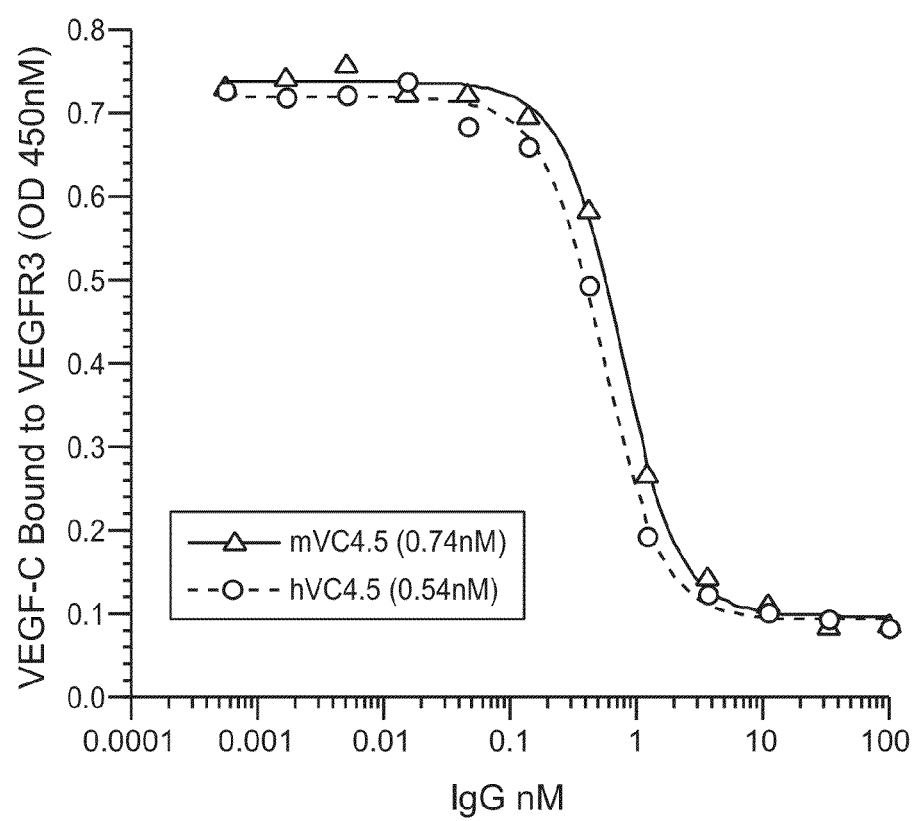

FIG. 10: Anti-VEGF-C antibody VC4.5 blocks VEGF-C binding to VEGFR3. Receptor blocking activities comparing the anti-VEGF-C antibody VC4.5 as murine IgG2a or human IgG1 form. Fixed concentration of biotin conjugated VEGF-C was incubated with serial dilutions of anti-VEGF-C antibody mVC4.5 (mIgG2a) and anti-VEGF-C antibody hVC4.5 (hIgG1) for 2 hours. The unbound VEGF-C was then captured by immobilized VEGFR3-Fc and detected with strepavidin-HRP conjugate.

Figure 11:
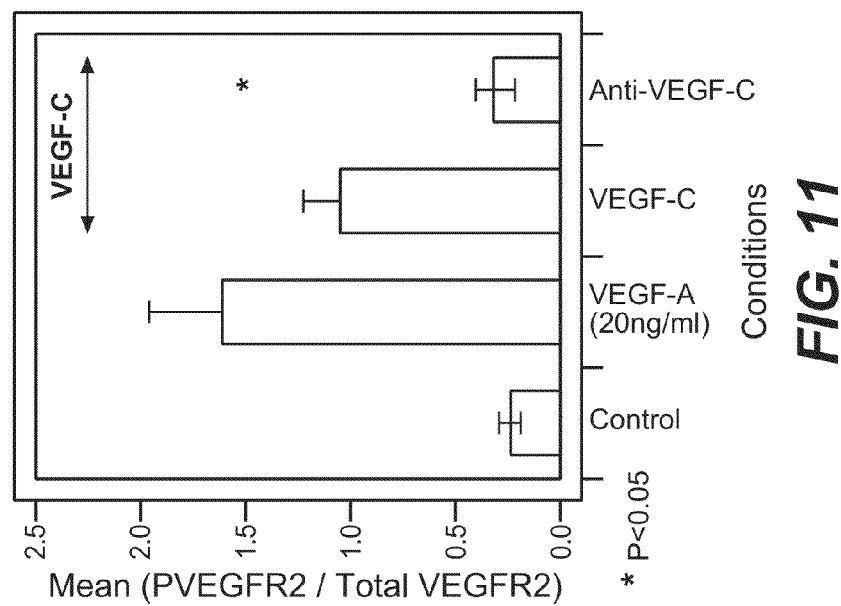

FIG. 11: Anti-VEGF-C antibody reduces VEGF-C-induced VEGFR2 activation in vitro. Receptor activation as assessed by pVEGFR2 production in response to 10 min of VEGF-A (20 ng/ml) or VEGF-C (200 ng/ml, R&D Systems) stimulation in the presence or absence of anti-VEGF-C antibody (10 µg/ml). Values are normalized to total VEGFR2 levels. pVEGFR2 and total VEGFR2 detected using ELISA kits (R&D Systems).

Figure 12:
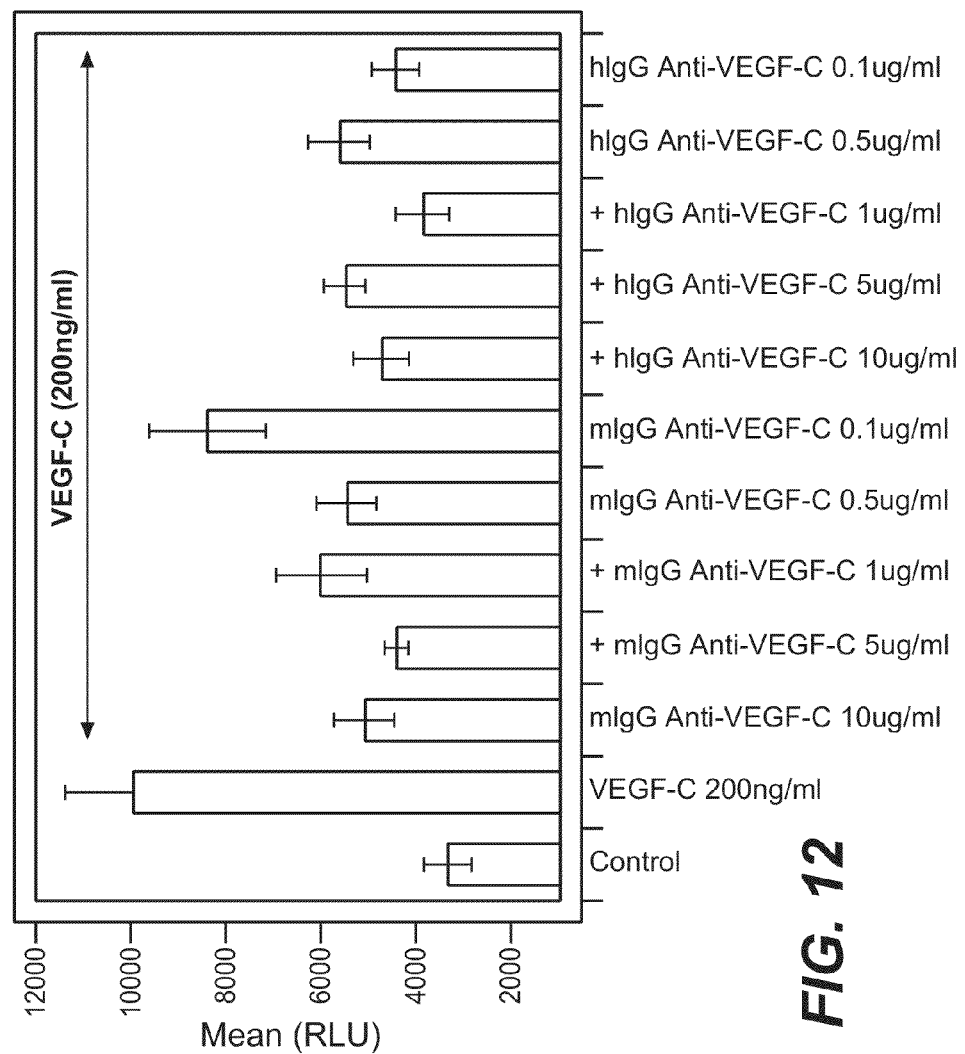

FIG. 12: Comparison of murine and human backbone anti-VEGF-C antibodies in a proliferation assay. LECs proliferation in response to 200 ng/ml of mature VEGF-C(R&D Systems) in the presence or absence of different doses of murine backbone or human backbone anti-VEGF-C antibodies (n=6 for each condition).

Figure 13:
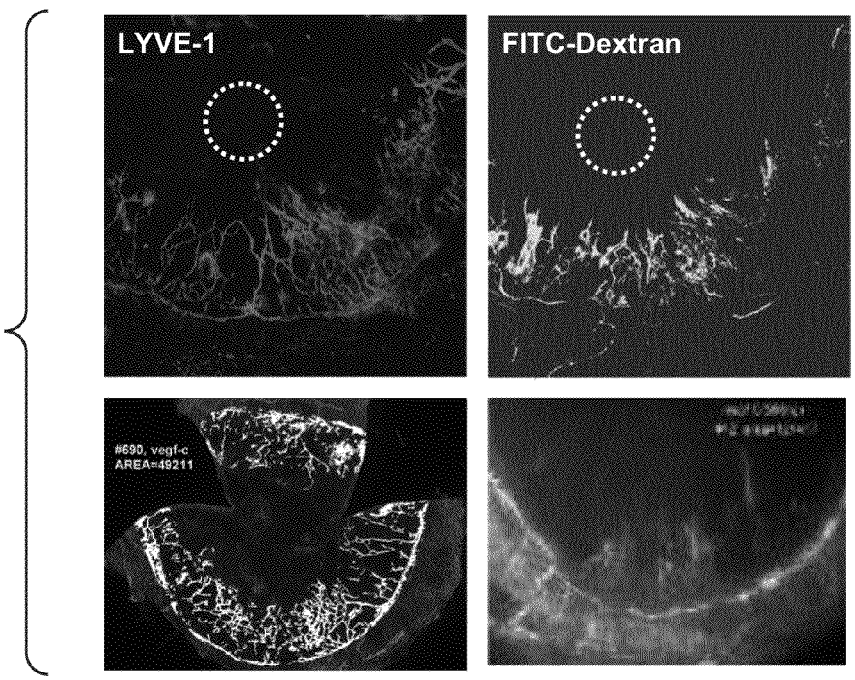

FIG. 13: Anti-VEGF-C antibody reduces VEGF-C-induced function in vivo. Representative images of LYVE-1 stained cornea, denoting lymphatics and FITC-Dextran denoting blood vessels, illustrating the effects of intracorneal placement of 150 ng pellet of VEGF-C (dotted circle) in the normally avascular cornea. The staining can be quantified as show in the panels below—areas to be included as positive in the analysis have been pseudocolored in the lower panels.

Figure 14A:
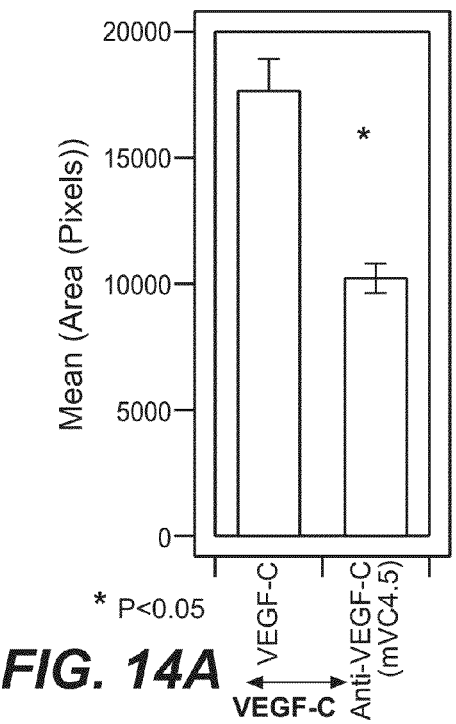
Figure 14B:
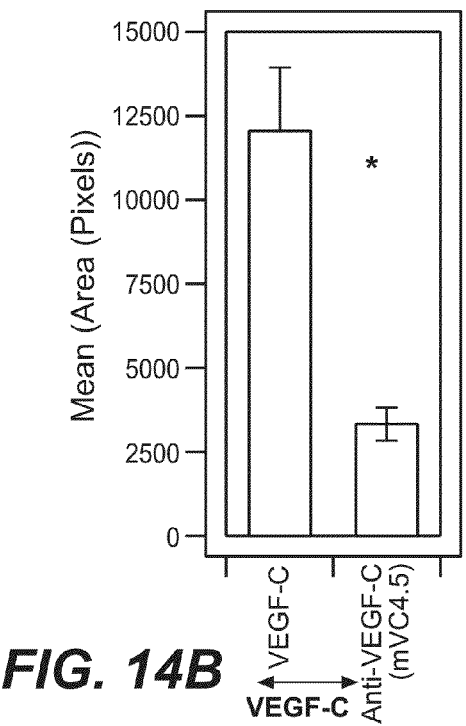

FIGS. 14A & 14B: Anti-VEGF-C antibody reduces VEGF-C-induced function in vivo. Quantification of the pixel counts evaluating (A) angiogenesis and (B) lymphangiogenesis from systemic treatment with anti-VEGF-C antibody (10 mg/kg twice weekly). *$p<0.05$; Error bars represent standard error of the mean.

Figure 15A:
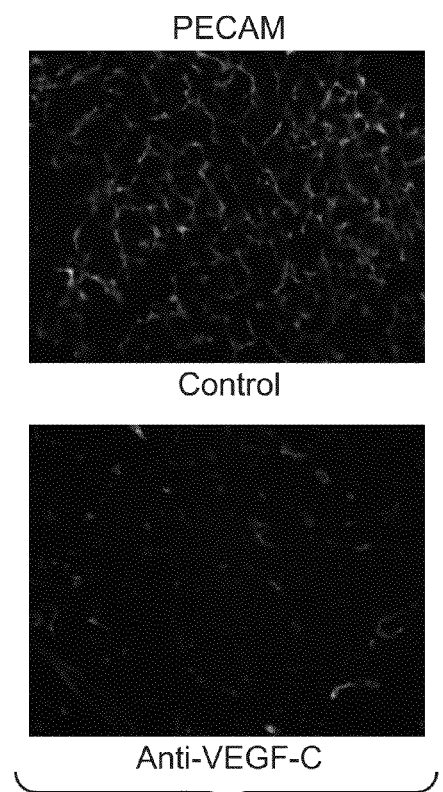
Figure 15B:
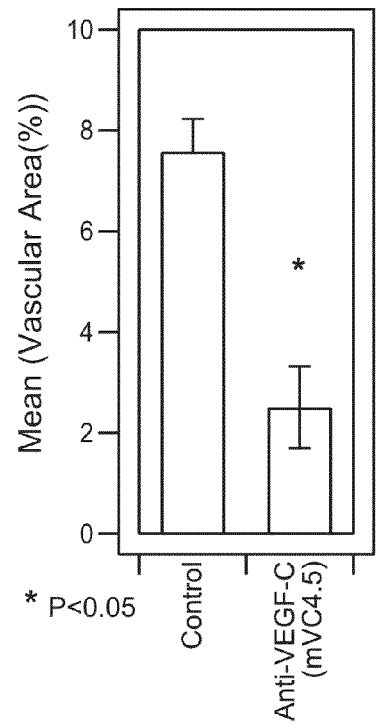

FIGS. 15A & 15B: Anti-VEGF-C antibody treatment results in a reduction of tumor angiogenesis in orthotopically grown 66c14 tumors. A. Representative images of PECAM-1 stained vessels in 66c14 tumors treated with isotype specific control (anti-Ragweed) antibody (top), or anti-VEGF-C antibody (bottom). B. Quantification of vascular vessel density was determined from 6 representative images from each of 6 tumors per group, evaluated for mean pixel number by ImageJ. *$p<0.05$; Error bars represent standard error of the mean.

Figure 16A:
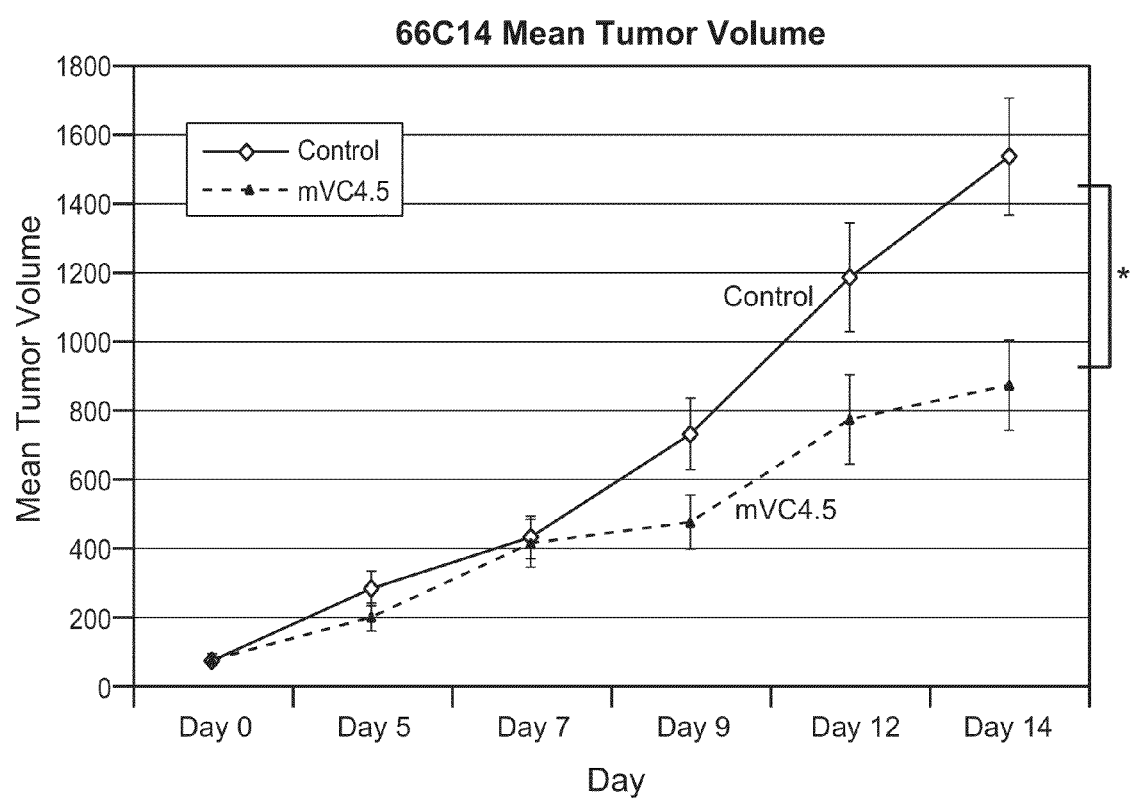
Figure 16B:
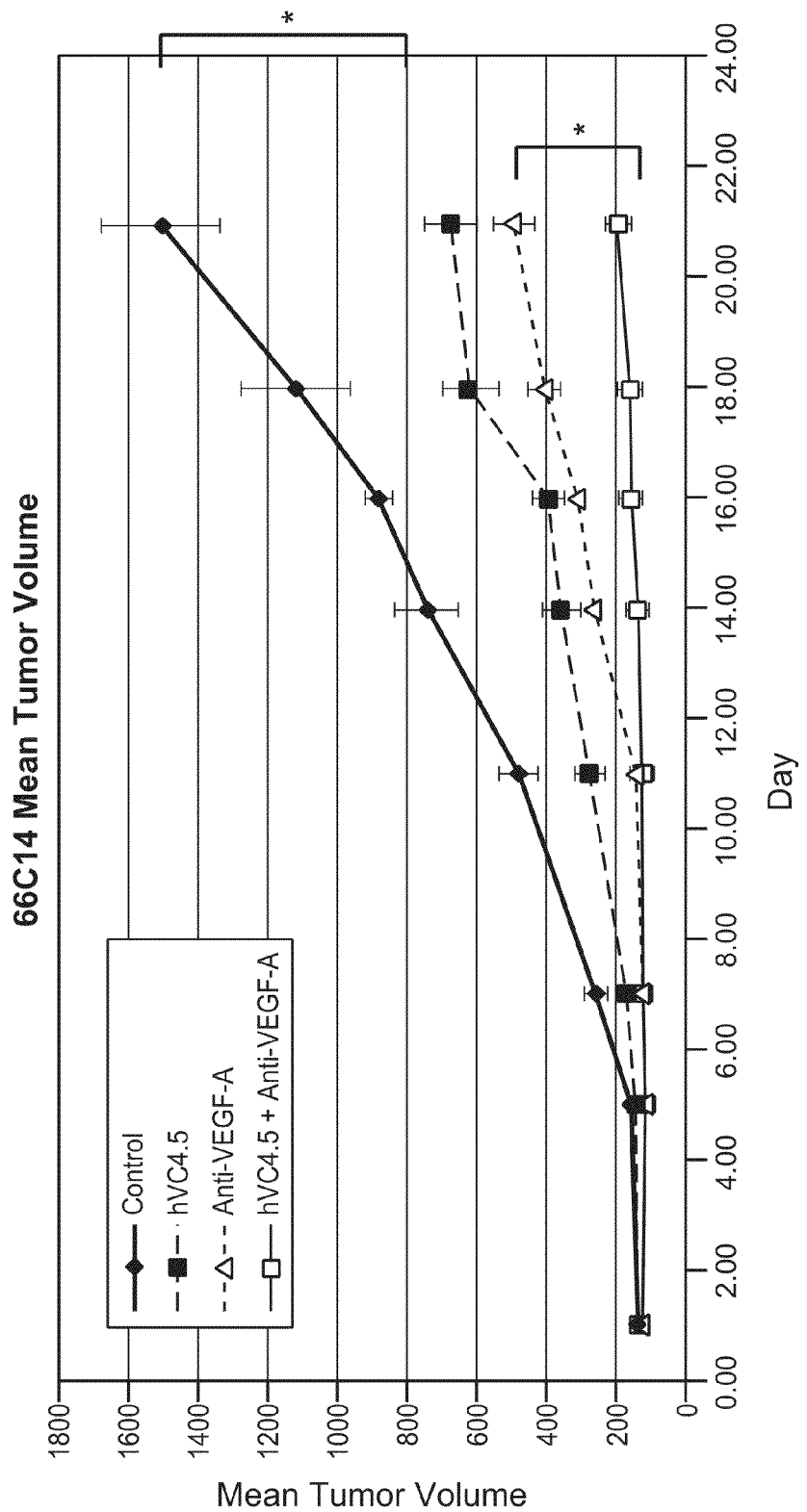

FIGS. 16A & 16B: Anti-VEGF-C antibody treatment results in a reduction of tumor growth in 66c14 tumors as a single agent or in combination with anti-VEGF-A. A. Mean tumor volume graph of 66c14 tumor model study analyzed in FIG. 15. Animals were dosed twice weekly i.p. with anti-VEGF-C antibody (10 mg/kg) once tumors reached an average size of 100 mm$^3$ and were dosed throughout the study. B. Mean tumor volume graph of an independent 66c14 tumor model study. Animals were dosed twice weekly i.p. with anti-VEGF-C (10 mg/kg), anti-VEGF-A antibody (5 mg/kg), or a combination of both agents, once tumors reached an average size of 100 mm$^3$ and were dosed throughout the study.

Figure 17:
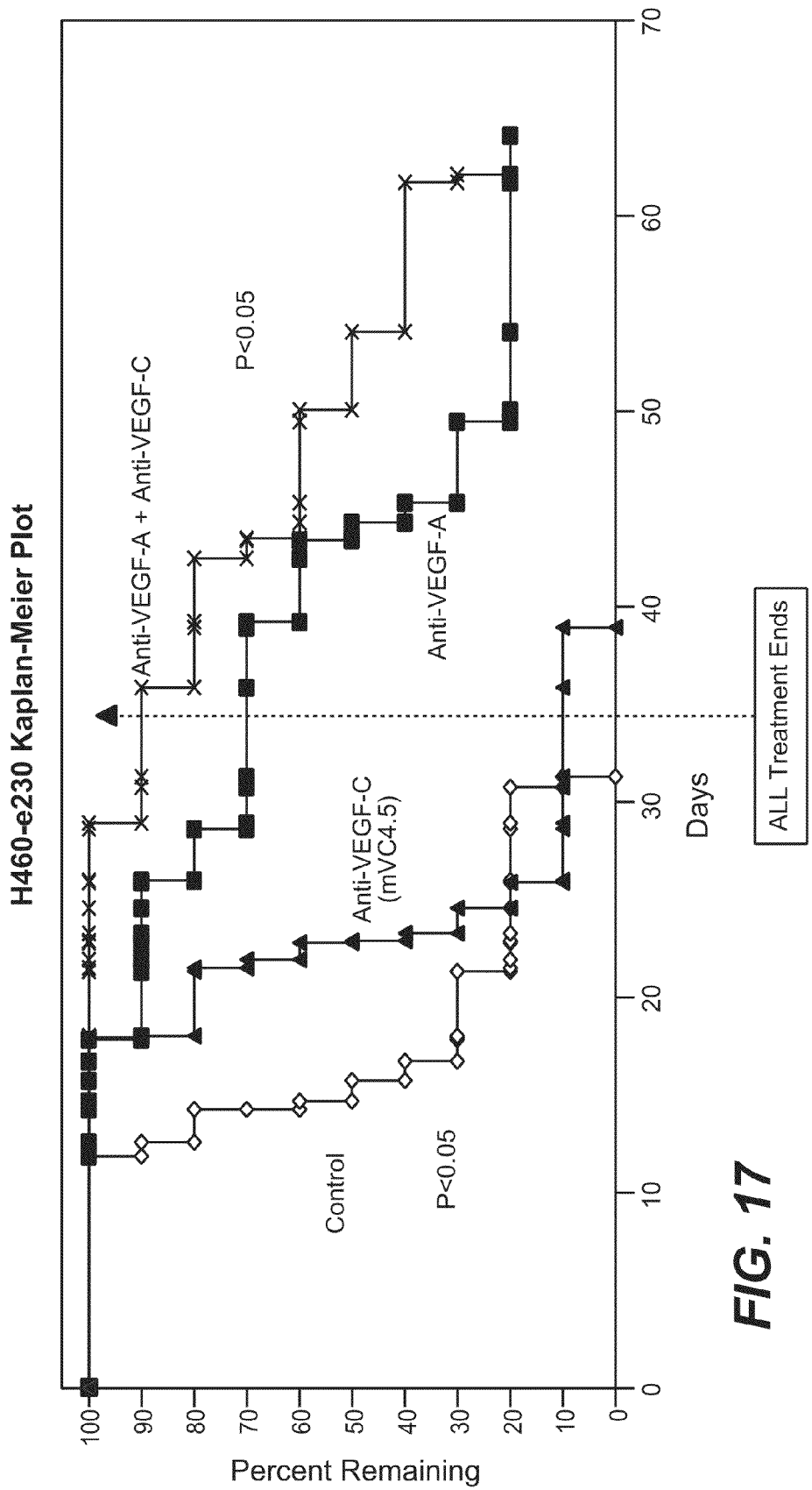

FIG. 17: Anti-VEGF-C antibody treatment results in a increased survival in H460 tumors as a single agent or in combination with anti-VEGF-A antibody. Kaplan-Meyer survival curves for groups of animals treated twice weekly i.p. with anti-VEGF-C antibody (10 mg/kg), anti-VEGF-A antibody (5 mg/kg), or a combination of both agents, once tumors reached an average size of 100 mm$^3$. Tumors were dosed for 5 weeks. Animals were removed from the study when tumor volume reached 1000 mm$^3$.

Figure 18B:
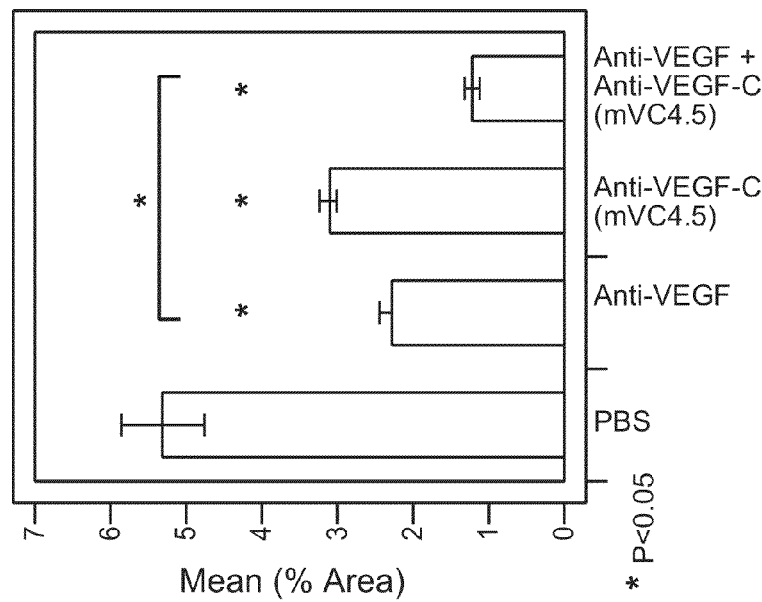
Figure 18A:
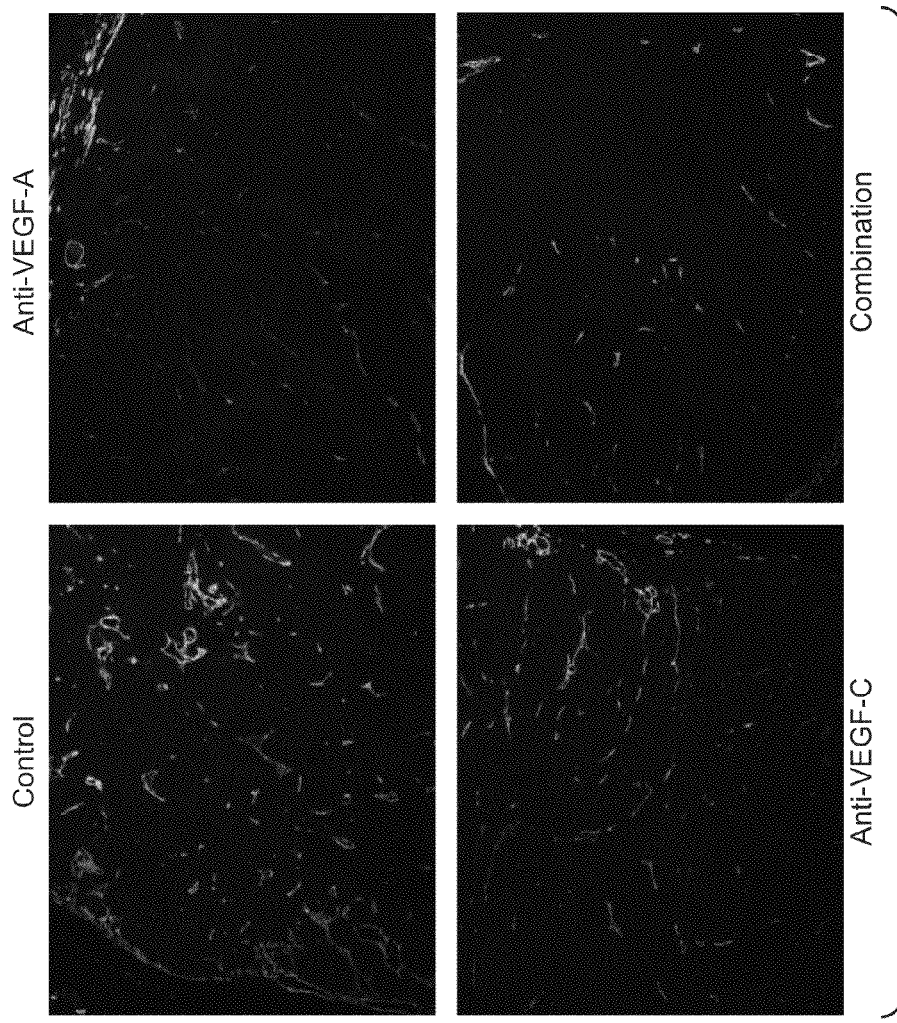

FIGS. 18A & 18B: Anti-VEGF-C antibody treatment results in a reduction of tumor angiogenesis in H460 tumors as a single agent or in combination with anti-VEGF-A antibody. A. Representative images of MECA32 stained vessels in H460 tumors treated with control antibody (top left), anti-VEGF-A antibody (top right), anti-VEGF-C antibody (bottom left) or combination of anti-VEGF-A antibody and anti-VEGF-C antibody (bottom right). B. Quantification of vascular vessel density was determined from 6 representative images from each of 6 tumors per group, evaluated for mean pixel number by ImageJ. Tumors were evaluated at study endpoint. *$p<0.05$; Error bars represent standard error of the mean.

Figure 19A:
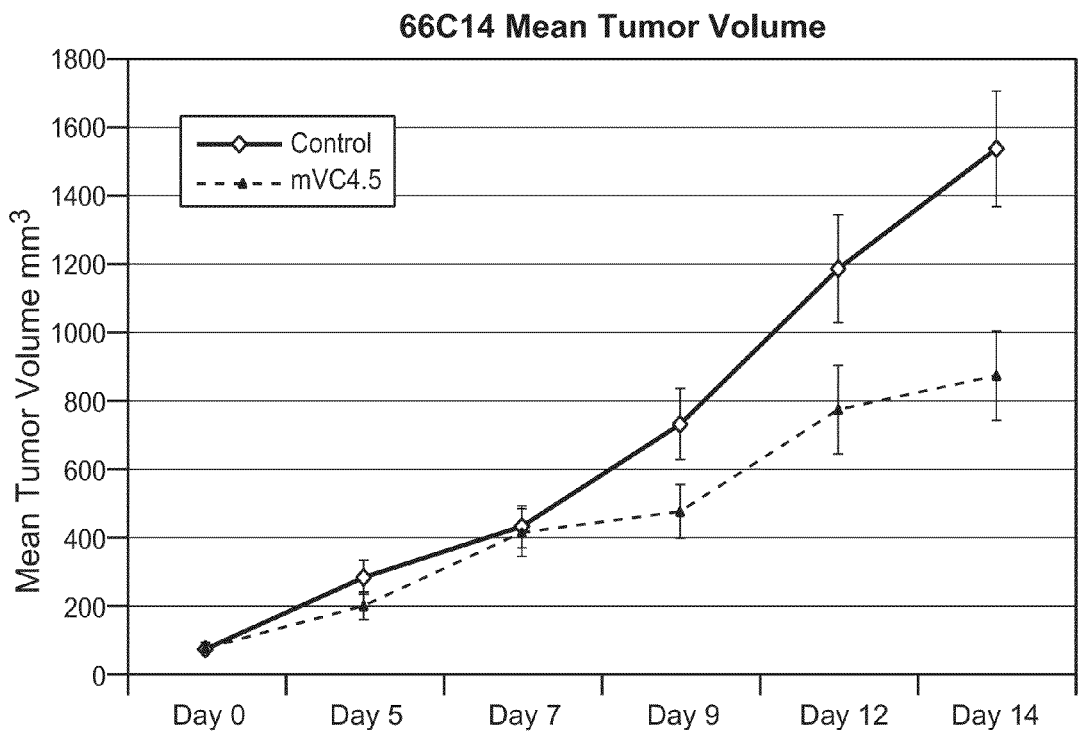
Figure 19B:
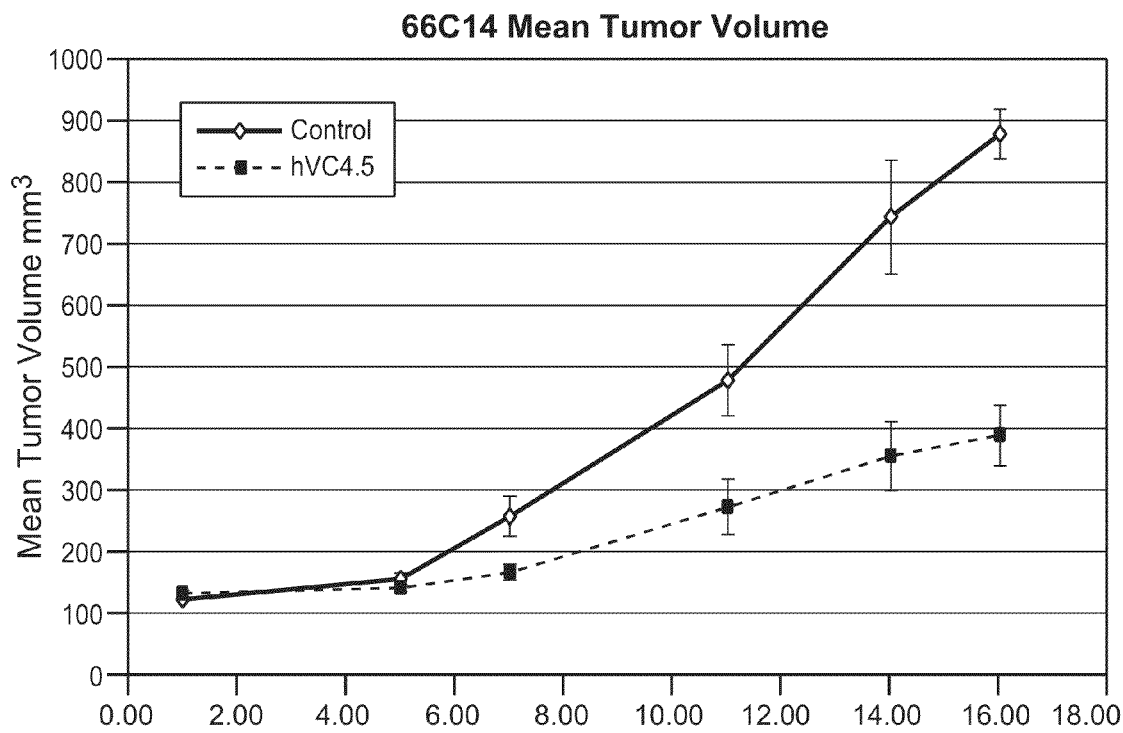

FIGS. 19A & 19B: Comparison of in vivo efficacy of the murine and human backbone anti-VEGF-C antibodies. Independent 66c14 tumor model studies were run with either A. murine or B. human backbone anti-VEGF-C antibody. Similar tumor growth curves are noted in the different studies suggesting equivalent activity in vivo.

Figure 20B:
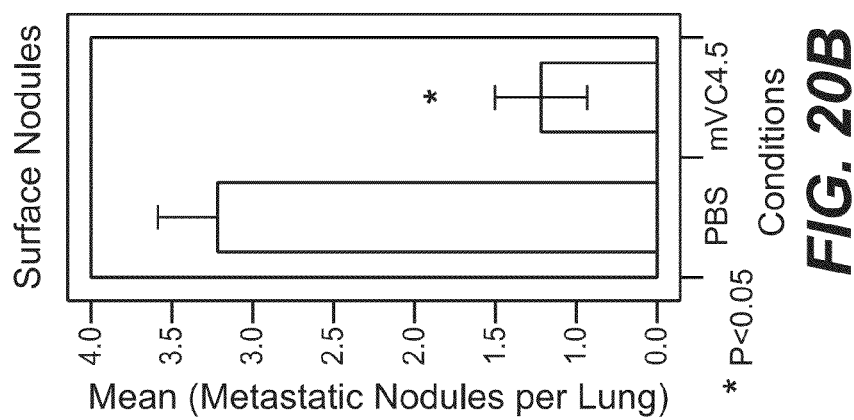
Figure 20A:
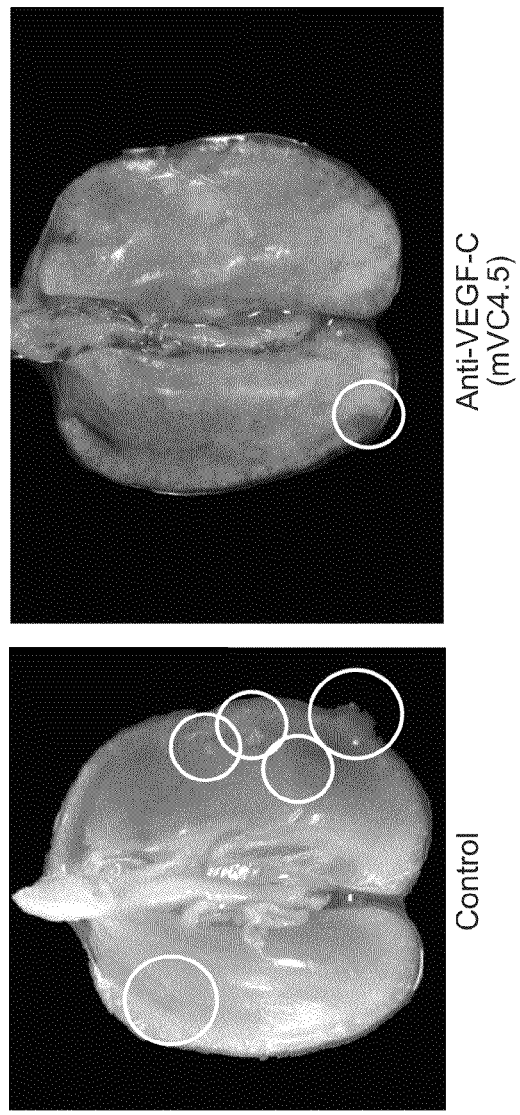

FIGS. 20A & 20B: Anti-VEGF-C antibody treatment results in a reduction of lung metastasis in 66c14 tumors. A. Representative images of lungs from control (left) and anti-VEGF-C antibody (right) treated animals. Lungs were inflated prior to fixation by right cardiac ventricular perfusion. Nodules are highlighted in white to facilitate visualization. B. Quantification by visual inspection of the number of metastatic nodules per lung in control and anti-VEGF-C antibody treated animals.

Figure 21A:
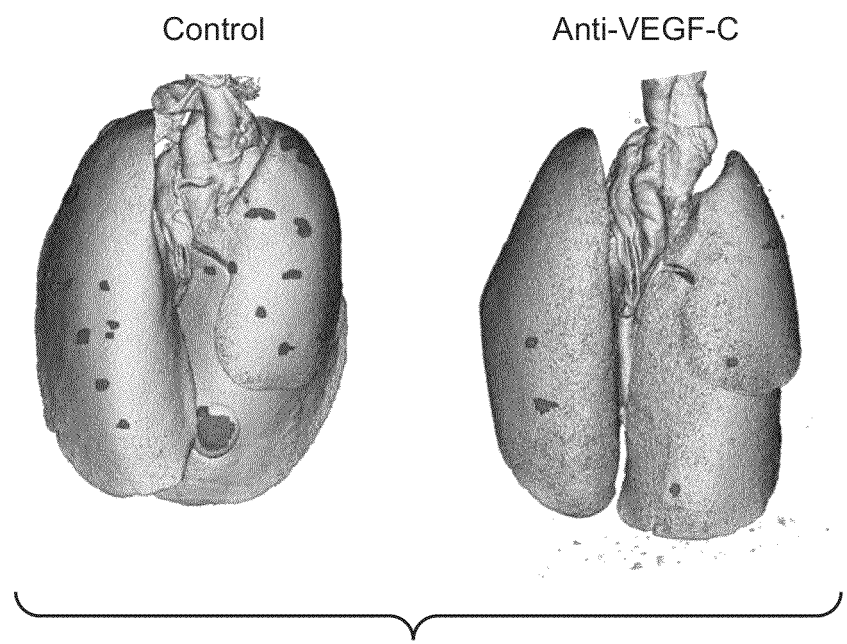
Figure 21B:
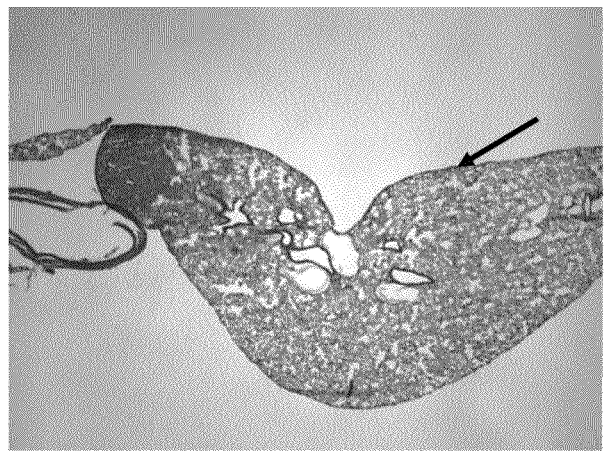

FIGS. 21A & 21B: A. Anti-VEGF-C antibody treatment results in a reduction of lung metastasis in 66c14 tumors. Three-dimensional renderings of representative micro-CT scanned lungs demonstrating metastatic nodules (red) in control and anti-VEGF-C antibody treated animals. B. H&E staining of a lung nodule (arrow) demonstrating metastatic tumor cells. *$p<0.05$; Error bars represent standard error of the mean.

Figure 22A:
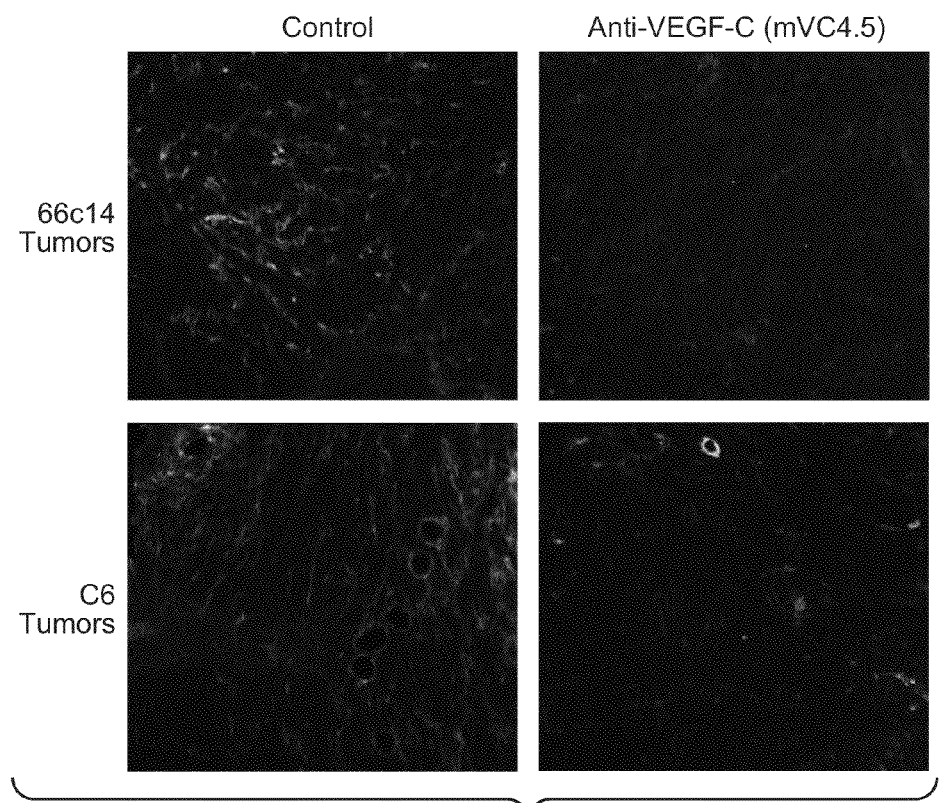
Figure 22B:
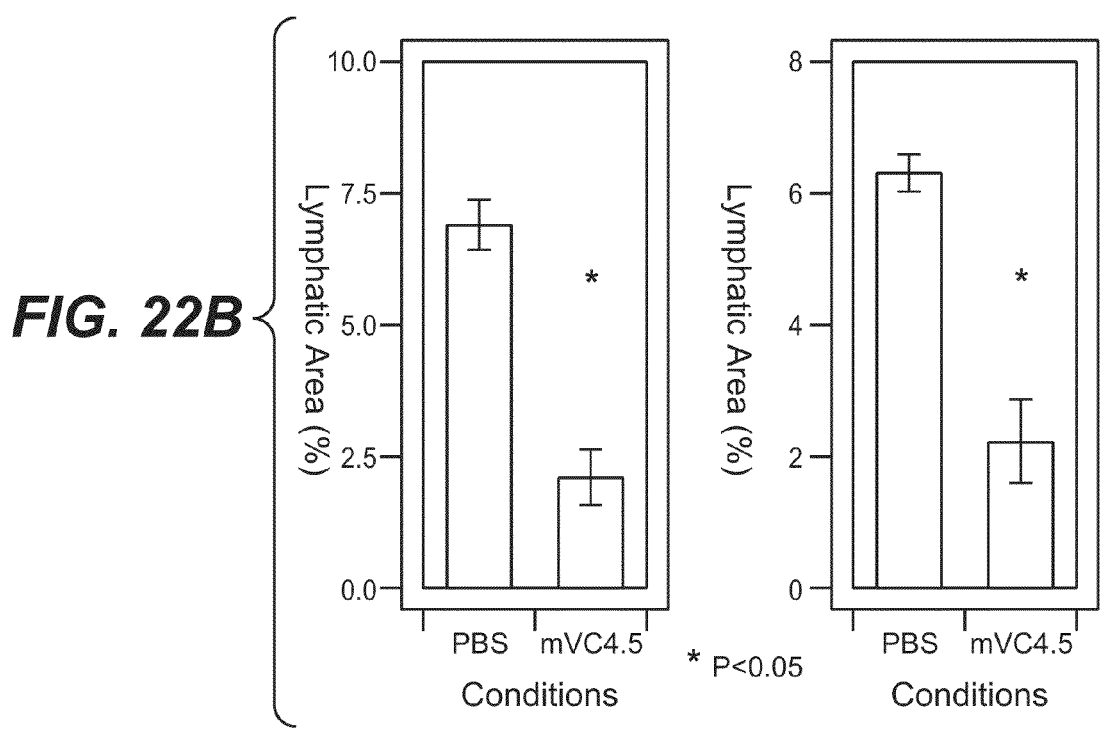

FIGS. 22A & 22B: Anti-VEGF-C antibody treatment results in a reduction of tumor lymphatic vessels. A. Representative images of LYVE-1 stained lymphatic vessels in 66c14 (top row) and C6 (bottom row) tumors treated with control antibody (left column) or anti-VEGF-C antibody (right column). B. Quantification of lymphatic vessel density was determined from 6 representative images from each of 6 tumors per group, evaluated for mean pixel number by ImageJ. *$p<0.05$; Error bars represent standard error of the mean.

FIG. 23: The L1, L2 and L3 amino acid sequences for anti-VEGF-C antibodies VC1, VC3 and VC4.

FIG. 24: The H1, H2 and H3 amino acid sequences for anti-VEGF-C antibodies VC1, VC3 and VC4.

FIG. 25: The L1, L2 and L3 amino acid sequences for anti-VEGF-C antibodies VC4, VC4.2, VC4.3, VC4.4 and VC4.5.

FIG. 26: The H1, H2 and H3 amino acid sequences for anti-VEGF-C antibodies VC4, VC4.2, VC4.3, VC4.4 and VC4.5.

FIG. 27: The L1, L2 and L3 amino acid sequences for anti-VEGF-C antibodies VC1, VC1.1, VC1.2, VC1.3, VC1.4, VC1.5, VC1.6, VC1.7, VC1.8, VC1.9, VC1.10, VC1.11 and VC1.12.

Figure 28:
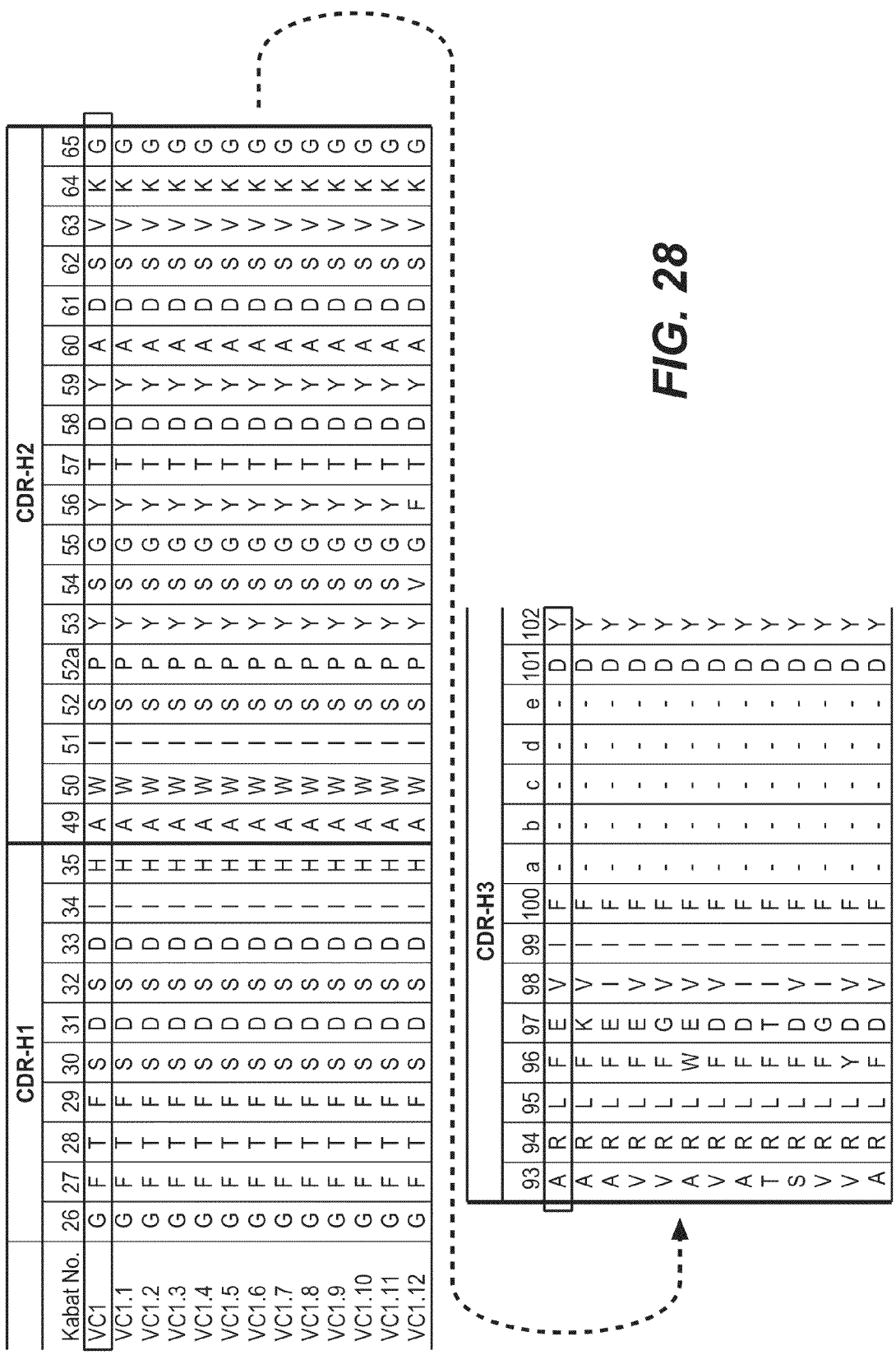

FIG. 28: The H1, H2 and H3 amino acid sequences for anti-VEGF-C antibodies VC1, VC1.1, VC1.2, VC1.3, VC1.4, VC1.5, VC1.6, VC1.7, VC1.8, VC1.9, VC1.10, VC1.11 and VC1.12.

FIG. 29: The L1, L2 and L3 amino acid sequences for anti-VEGF-C antibodies VC1.12, VC1.12.1, VC1.12.2, VC1.12.3, VC1.12.4, VC1.12.5, VC1.12.6, VC1.12.8, VC1.12.9 and VC1.12.10.

FIG. 30: The H1, H2 and H3 amino acid sequences for anti-VEGF-C antibodies VC1.12, VC1.12.1, VC1.12.2, VC1.12.3, VC1.12.4, VC1.12.5, VC1.12.6, VC1.12.8, VC1.12.9 and VC1.12.10.

FIG. 31: Table summarizing binding affinity data of anti-VEGF-C antibodies VC1, VC3 and VC4.

Figures 32, 33, 34:
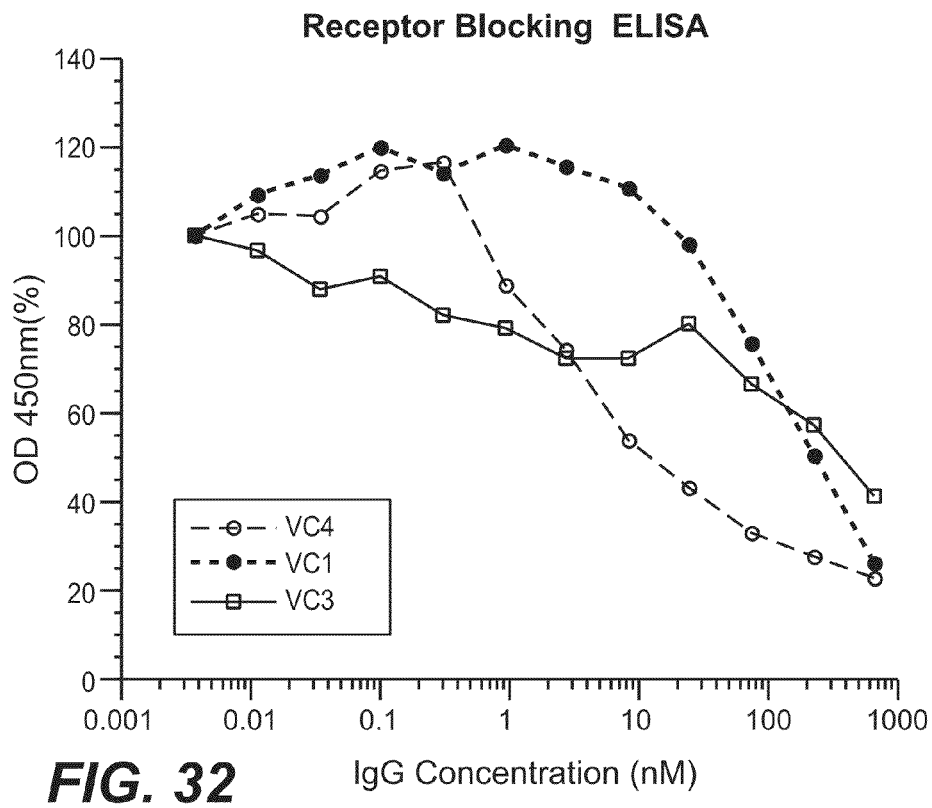

FIG. 32: Receptor blocking activities of anti-VEGF-C IgGs VC1, VC3 and VC4. Anti-VEGF-C IgGs VC1, VC3 and VC4 block biotinylated-human VEGF-C binding to VEGFR3 coated plate in dose-dependent manner.

FIG. 33: Table summarizing the Phage $IC_{50}$ data of VC4 affinity improved variants (VC4.2, VC4.3, VC4.4 and VC4.5) to human VEGF-C.

FIG. 34: Table summarizing the kinetic binding affinity measurement of anti-VEGF-C antibody VC4.5 Fab protein and anti-VEGF-C antibody VC4.5 IgG to human VEGF-C (R&D systems) and human VEGF-C C137S.

Figures 35, 36, 37:
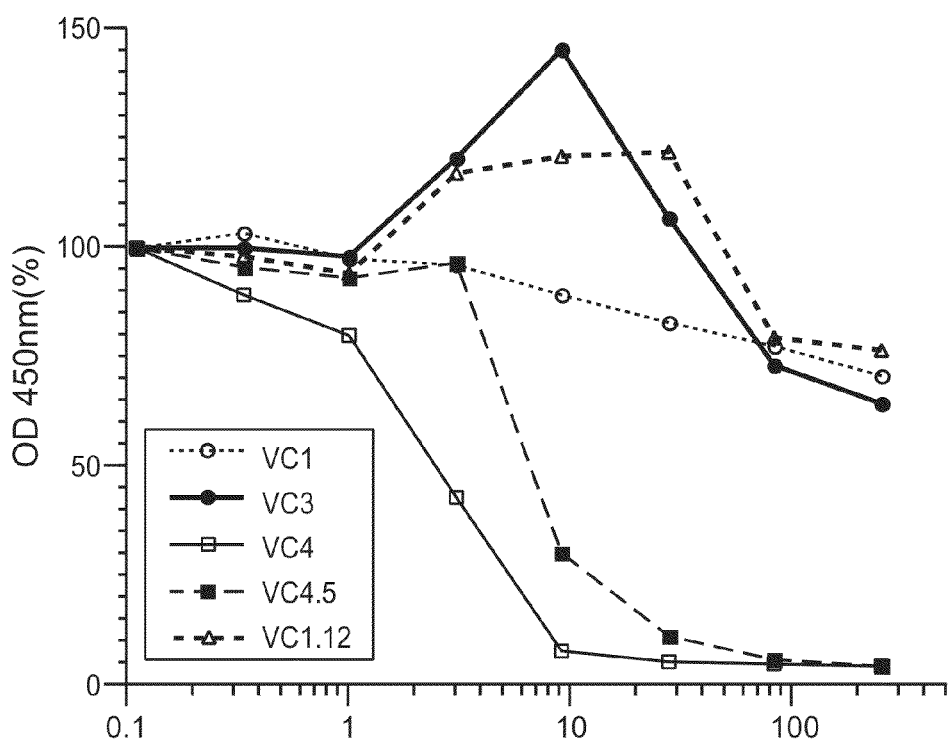

FIG. 35: Table summarizing the Phage $IC_{50}$ data of VC1 affinity improved variants (VC1.1, VC1.2, VC1.3, VC1.4, VC1.5, VC1.6, VC1.7, VC1.8, VC1.9, VC1.10, VC1.11 and VC1.12) to human VEGF-C.

FIG. 36: Table summarizing the Phage $IC_{50}$ data of VC1.12 affinity improved variants (VC1.12.1, VC1.12.2, VC1.12.3, VC1.12.4, VC1.12.5, VC1.12.6, VC1.12.8, VC1.12.9 and VC1.12.10) to human VEGF-C C137S.

FIG. 37: Epitope mapping of anti-VEGF-C antibodies. VC4 has different epitope to VC3 and VC1 series antibodies.

FIG. 38: Depicts the light chain variable regions of anti-VEGF-C antibodies VC1.12 and VC4.5.

FIG. 39: Depicts the heavy chain variable regions of anti-VEGF-C antibodies VC1.12 and VC4.5.

Figure 40:
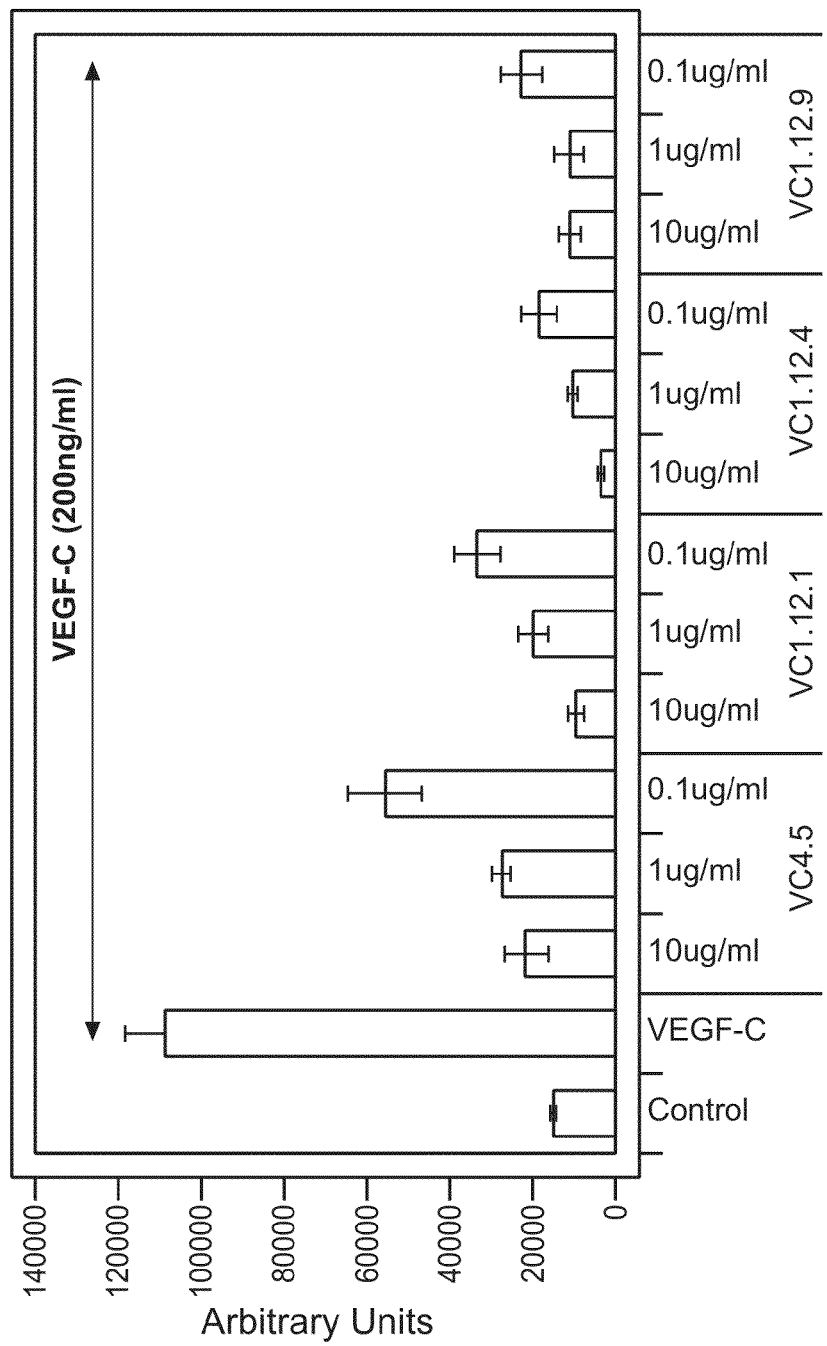

FIG. 40: Cell proliferation assay—anti-VEGF-C antibodies reduce VEGF-C-induced cellular proliferation in vitro.

Figure 41:
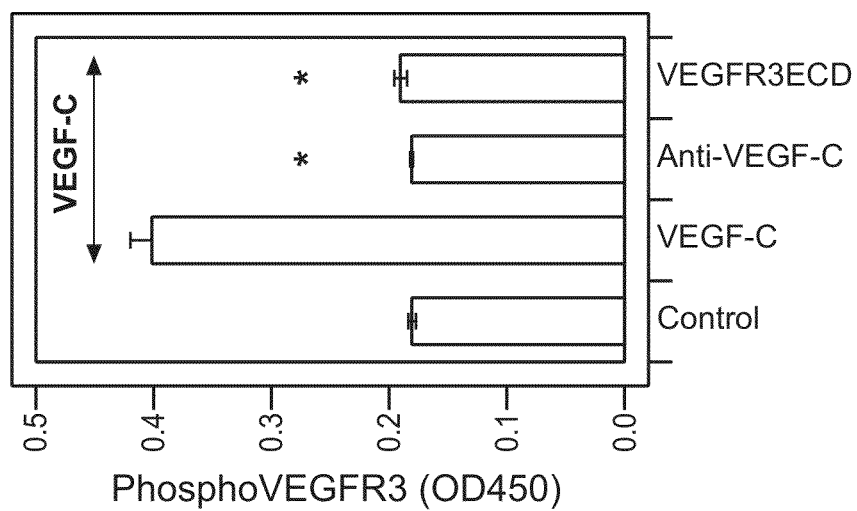

FIG. 41: Anti-VEGF-C antibody inhibits VEGF-C mediated phosphorylation of VEGFR3. VEGFR3 phosphorylation level as assayed by the VEGFR3 KIRA assay. VEGF-C (200 ng/ml) was added for 10 min in the presence or absence of anti-VEGF-C antibody (10 μg/ml) or VEGFR3 ECD (10 μg/ml) to evaluate the induction of the phosphorylation of VEGFR3 (n=6 for each condition). *$p<0.05$; Error bars represent standard error of the mean.

Figure 42:
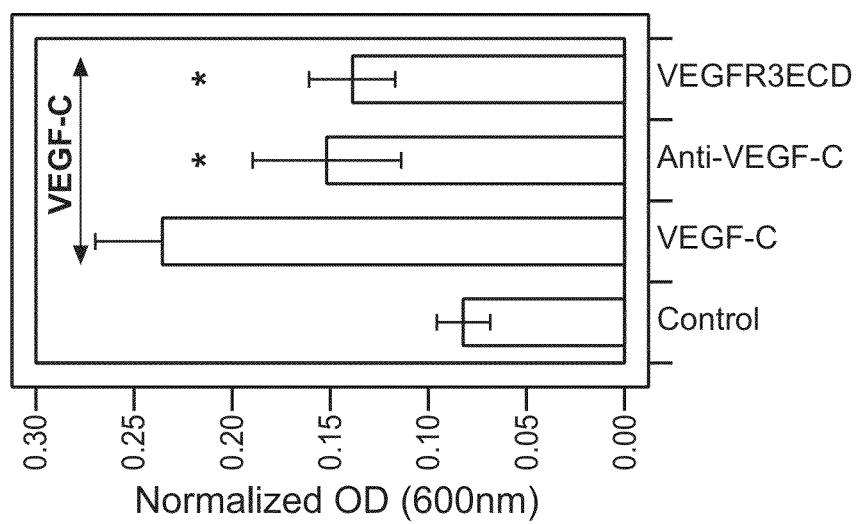

FIG. 42: Treatment with anti-VEGF-C antibody reduced VEGF-C induced vascular permeability. Quantification of results from mouse skin vascular permeability assay. The quantification was determined from the Evan's blue dye extracted from skin samples in the permeability assay. Animals were treated with anti-VEGF-C antibody (0.5 mg/ml) or VEGFR3 ECD (1.0 mg/ml). Values shown are the average of 6 independent experiments. *$p<0.05$; Error bars represent standard error of the mean.

Figure 43B:
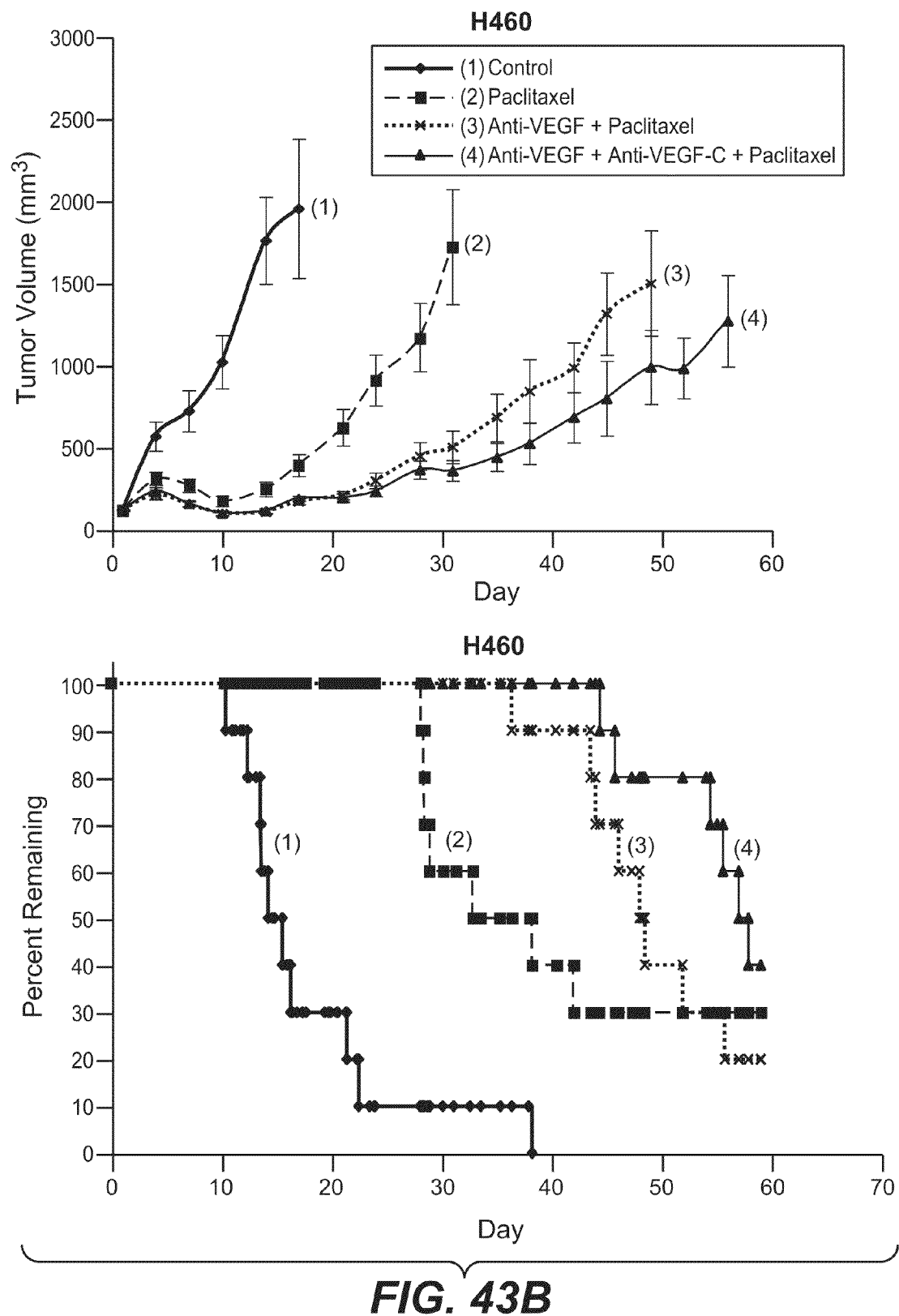

FIGS. 43A & 43B: Concomitant inhibition of VEGF-C and VEGF provides additional benefit for primary tumor growth stasis. A. Mean tumor growth curve for A549 where ordering of treatments was altered. Treatments were administered for the duration as noted by the arrows at 5 mg/kg twice weekly for anti-VEGF antibody and 10 mg/kg twice weekly for anti-VEGF-C antibody. B. Mean tumor growth curve and Kaplan Meier curve for H460 tumor model treated with control, paclitaxel, anti-VEGF+paclitaxel or anti-VEGF+anti-VEGF-C+paclitaxel. Treatments were administered at 5 mg/kg twice weekly for anti-VEGF antibody and 10 mg/kg twice weekly for anti-VEGF-C antibody for 5 weeks each and 30 mg/kg every other day for 10 days for paclitaxel.

Figure 44:
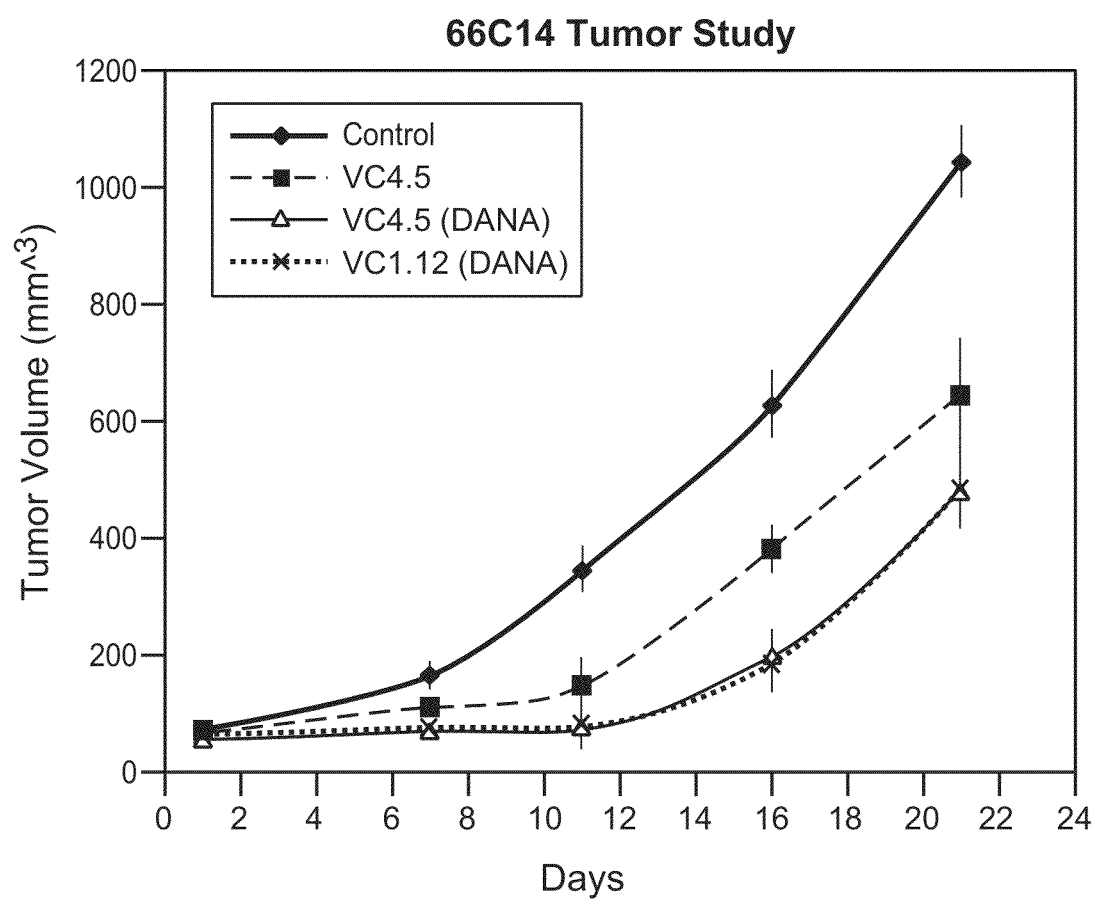

FIG. 44: Comparison of in vivo efficacy of the mouse backbone anti-VEGF-C antibodies using 66c14 tumor model.

Figure 45:
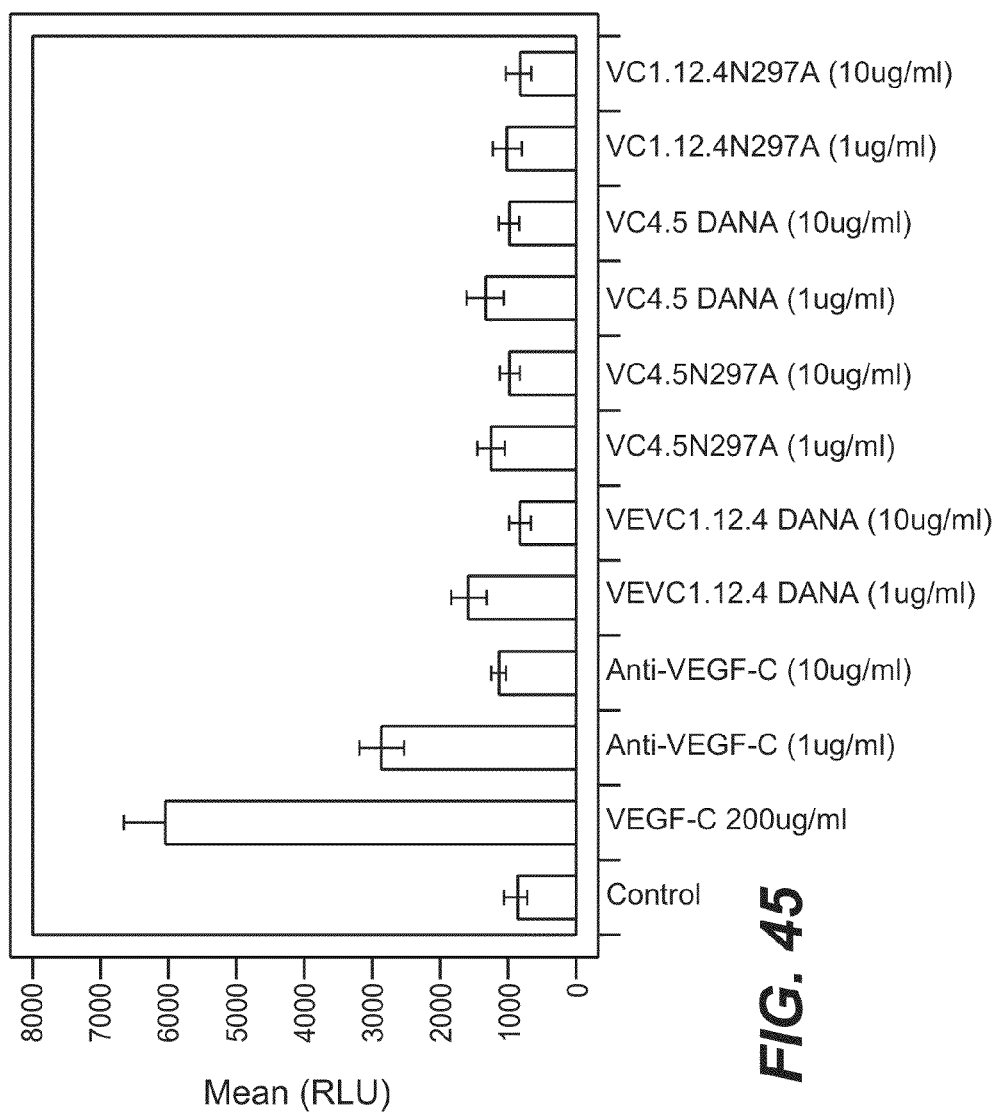

FIG. 45: Comparison of anti-VEGF-C antibodies in a proliferation assay. LECs proliferation in response to 200 ng/ml of mature VEGF-C in the presence or absence of different doses of anti-VEGF-C antibodies.

Figure 46:
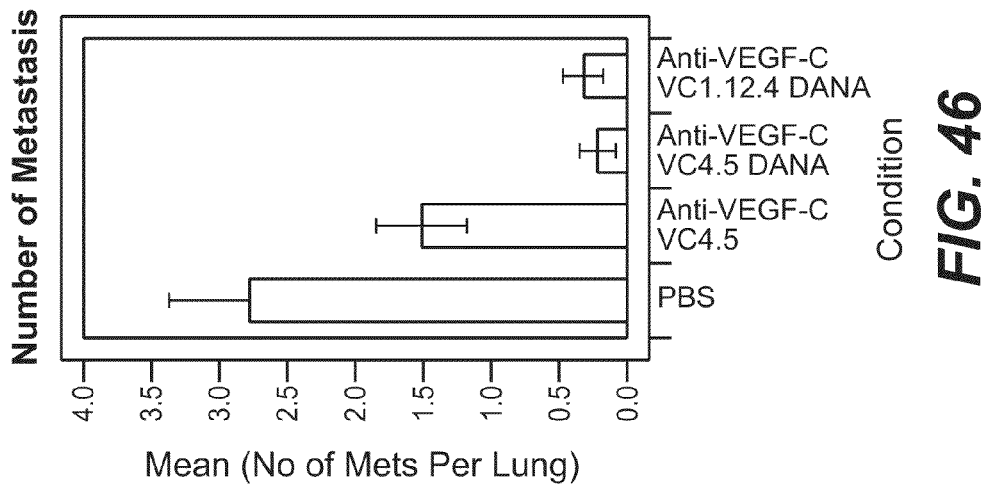

FIG. 46: Anti-VEGF-C treatment results in a reduction of number of metastatic tumor lesions in mice.

DETAILED DESCRIPTION OF THE INVENTION

The invention herein provides isolated antibodies that bind to VEGF-C, that are useful for, e.g., diagnosis, treatment or prevention of disease states associated with activity of VEGF-C. Pharmaceutical compositions as well as methods of treatment are also provided. In some embodiments, the antibodies of the invention are used to treat a tumor, a cancer, and/or a cell proliferative disorder. In some embodiments, the antibodies of the invention are used to treat a pathological condition associated with lymphangiogenesis and angiogenesis.

In another aspect, the anti-VEGF-C antibodies of the invention find utility as reagents for detection and/or isolation of VEGF-C, such as detection of VEGF-C in various tissues and cell type.

The invention further provides methods of making anti-VEGF-C antibodies, and polynucleotides encoding anti-VEGF-C antibodies.

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Definitions

For purposes of interpreting this specification, the following definitions will apply and whenever appropriate, terms used in the singular will also include the plural and vice versa.

In the event that any definition set forth below conflicts with any document incorporated herein by reference, the definition set forth below shall control.

The term "antibody" herein is used in the broadest sense and encompasses various immunoglobulin structures, including but not limited to monoclonal antibodies, polyclonal antibodies, multispecific antibodies, and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147 (1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, in another embodiment at least 80%, in another embodiment at least 85%, in another embodiment at least 90%, and yet in another embodiment at least 95%. Identity or similarity with respect to this sequence is defined herein as the percentage of amino acid residues in the candidate sequence that are identical (i.e. same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (V$_H$-V$_L$). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
|    |         | (Kabat Numbering) |  |  |
| H1 | H31-H35 | H26-H35 | H26-H32 | H30-H35 |
|    |         | (Chothia Numbering) |  |  |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Publication No. 2008/0181888, Figures for EU numbering).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), wherein the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies and antibody fragments that have been linked covalently or non-covalently. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

"Polyepitopic specificity" refers to the ability to specifically bind to two or more different epitopes on the same or different antigen(s). For example, "bispecific" as used herein refers to the ability to bind two different epitopes. "Monospecific" refers to the ability to bind only one epitope.

The expression "single domain antibodies" (sdAbs) or "single variable domain (SVD) antibodies" generally refers to antibodies in which a single variable domain ($V_H$ or $V_L$) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003):21:484-490; WO 2005/035572; WO 03/035694; Febs Lett (1994) 339: 285-290; WO00/29004; WO 02/051870).

The expression "linear antibodies" generally refers to the antibodies described in Zapata et al., Protein Eng. 8(10): 1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody," as used herein, is an antibody which partially or fully mimics at least one of the functional activities of a polypeptide of interest.

"Growth inhibitory" antibodies are those that prevent or reduce proliferation of a cell expressing an antigen to which the antibody binds.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capeli et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the Kd or Kd value is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN-20™ surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$," according to this invention can also be determined as described above using a BIACORE®-2000 or a BIACORE®-3000 system (BIAcore, Inc., Piscataway, N.J.).

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferably those changes occur at only three, two, or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. In one embodiment, for the VL, the subgroup is subgroup kappa I as in Kabat et al., supra. In one embodiment, for the VH, the subgroup is subgroup III as in Kabat et al., supra.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences:

EVQLVESGGGLVQPGGSLRLSCAAS (SEQ ID NO: 63)-H1-WVRQAPGKGLEWV (SEQ ID NO: 64)-H2-RFTISADTSKNTLYLQMNSLRAEDTAVYYC (SEQ ID NO: 65)-H3-WGQGTLVTVSS (SEQ ID NO: 66). See FIG. 4.

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

DIQMTQSPSSLSASVGDRVTITC (SEQ ID NO: 67)-L1-WYQQKPGKAPKLLIY (SEQ ID NO: 68)-L2-GVPSRFSGSGSGTDFTLTISSLQPEDFATYYC (SEQ ID NO: 69)-L3-FGQGTKVEIK (SEQ ID NO: 70). See FIG. 5.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, e.g., NNK, NNS, XYZ, DVK and the like. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al. (1999) *J. Mol. Biol.* 296:57-86); Garrard & Henner (1993) *Gene* 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

The expression "linear antibodies" refers to the antibodies described in Zapata et al. (1995 *Protein Eng,* 8(10):1057-1062). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) *Curr. Opin. Struct. Biol.* 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) *Methods: A companion to Methods in Enzymology* 3:205-0216.

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. In one embodiment, solvent accessible positions are determined using coordinates from a 3-dimensional model of an antibody, preferably using a computer program such as the InsightII program (Accelrys, San Diego, Calif.). Solvent accessible positions can also be determined using algorithms known in the art (e.g., Lee and Richards (1971) *J. Mol. Biol.* 55, 379 and Connolly (1983) *J. Appl. Cryst.* 16, 548). Determination of solvent accessible positions can be performed using software suitable for protein modeling and 3-dimensional structural information obtained from an antibody. Software that can be utilized for these purposes includes SYBYL Biopolymer Module software (Tripos Associates). Generally, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios (1994) *Comput. Chem.* 18(4): 377-386.

The process of vascular development is tightly regulated. To date, a significant number of molecules, mostly secreted factors produced by surrounding cells, have been shown to regulate EC differentiation, proliferation, migration and coalescence into cord-like structures. For example, vascular endothelial growth factor (VEGF) has been identified as the key factor involved in stimulating angiogenesis and in inducing vascular permeability. Ferrara et al., *Endocr. Rev.* 18:4-25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., *Endocr. Rev.* supra. The VEGF mRNA is overexpressed by the majority of human tumors examined. Berkman et al., *J. Clin. Invest.* 91:153-159 (1993); Brown et al., *Human Pathol.* 26:86-91 (1995); Brown et al., *Cancer Res.* 53:4727-4735 (1993); Mattern et al., *Brit. J. Cancer* 73:931-934 (1996); Dvorak et al., *Am. J. Pathol.* 146:1029-1039 (1995).

Anti-VEGF neutralizing antibodies suppress the growth of a variety of human tumor cell lines in nude mice (Kim et al., Nature 362:841-844 (1993); Warren et al., *J. Clin. Invest.* 95:1789-1797 (1995); Borgström et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Ophthalmol.* 114:66-71 (1996). Therefore, anti-VEGF monoclonal antibodies or other inhibitors of VEGF action are promising candidates for the treatment of tumors and various intraocular neovascular disorders. Such antibodies are described, for example, in EP 817,648 published Jan. 14, 1998; and in WO98/45331 and WO98/45332, both published Oct. 15, 1998. One of the anti-VEGF antibodies, bevacizumab, has been approved by the FDA for use in combination with a chemotherapy regimen to treat metastatic colorectal cancer (CRC) and non-samll cell lung cancer (NSCLC). And bevacizumab is being investigated in many ongoing clinical trials for treating various cancer indications.

Other anti-VEGF antibodies, anti-Nrp1 antibodies and anti-Nrp2 antibodies are also known, and described, for example, in Liang et al., *J Mol Biol* 366, 815-829 (2007) and Liang et al., *J Biol Chem* 281, 951-961 (2006), PCT publication number WO2007/056470 and PCT Application No. PCT/US2007/069179, the content of these patent applications are expressly incorporated herein by reference.

An "angiogenic factor or agent" is a growth factor which stimulates the development of blood vessels, e.g., promote angiogenesis, endothelial cell growth, stabiliy of blood vessels, and/or vasculogenesis, etc. For example, angiogenic factors, include, but are not limited to, e.g., VEGF and members of the VEGF family (VEGF-B, VEGF-C and VEGF-D), P1GF, PDGF family, fibroblast growth factor family (FGFs), TIE ligands (Angiopoietins), ephrins, Delta-like ligand 4 (DLL4), Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, neuropilins, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003)*Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or to the VEGF-A receptor (e.g., KDR receptor or Flt-1 receptor), anti-PDGFR inhibitors such as Gleevec™ (Imatinib Mesylate), small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12):1359-1364; Tonini et al. (2003) *Oncogene* 22:6549-6556 (e.g., Table 2 listing known antiangiogenic factors); and, Sato (2003) *Int. J. Clin. Oncol.* 8:200-206 (e.g., Table 1 listing anti-angiogenic agents used in clinical trials).

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) *Science* 246:1306, and Houck et al. (1991) *Mol. Endocrin,* 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

A "VEGF antagonist" refers to a molecule capable of neutralizing, blocking, inhibiting, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases. The term "VEGF antagonist," as used herein, specifically includes molecules, including antibodies, antibody fragments, other binding polypeptides, peptides, and non-peptide small molecules, that bind to VEGF and are capable of neutralizing, blocking, inhibiting, abrogating, reducing or interfering with VEGF activities. Thus, the term "VEGF activities" specifically includes VEGF mediated biological activities of VEGF.

An "anti-VEGF antibody" is an antibody that binds to VEGF with sufficient affinity and specificity. In one embodiment, the anti-VEGF antibody can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as P1GF, PDGF or bFGF. In one embodiment, anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody (see Presta et al. (1997) *Cancer Res.* 57:4593-4599), including but not limited to the antibody known as "bevacizumab (BV)," also known as "rhuMAb VEGF" or "AVASTIN®." AVASTIN® is presently commercially available. Bevacizumab comprises mutated human IgG$_1$ framework regions and antigen-binding complementarity-determining regions from the murine antibody A.4.6.1 that blocks binding of human VEGF to its receptors. Approximately 93% of the amino acid sequence of bevacizumab, including most of the framework regions, is derived from human IgG$_1$, and about 7% of the sequence is derived from A4.6.1. Bevacizumab has a molecular mass of about 149,000 daltons and is glycosylated. Bevacizumab and other humanized anti-VEGF antibodies are further described in U.S. Pat. No. 6,884,879, issued Feb. 26, 2005. Additional anti-VEGF antibodies include the G6 or B20 series antibodies (e.g., G6-23, G6-31, B20-4.1), as described in PCT Application Publication No. WO2005/012359. For additional antibodies see U.S. Pat. Nos. 7,060,269, 6,582,959, 6,703,020; 6,054, 297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004).

The term "B20 series polypeptide" as used herein refers to a polypeptide, including an antibody that binds to VEGF. B20 series polypeptides includes, but not limited to, antibodies derived from a sequence of the B20 antibody or a B20-derived antibody described in US Publication No. 20060280747, US Publication No. 20070141065 and/or US Publication No. 20070020267, the content of these patent applications are expressly incorporated herein by reference. In one embodiment, B20 series polypeptide is B20-4.1 as described in US Publication No. 20060280747, US Publication No. 20070141065 and/or US Publication No. 20070020267. In another embodiment, B20 series polypeptide is B20-4.1.1 described in PCT Publication No. WO 2009/073160, the entire disclosure of which is expressly incorporated herein by reference.

The term "G6 series polypeptide" as used herein refers to a polypeptide, including an antibody that binds to VEGF. G6 series polypeptides includes, but not limited to, antibodies derived from a sequence of the G6 antibody or a G6-derived antibody described in US Publication No. 20060280747, US Publication No. 20070141065 and/or US Publication No. 20070020267. G6 series polypeptides, as described in US Publication No. 20060280747, US Publication No. 20070141065 and/or US Publication No. 20070020267 include, but not limited to, G6-8, G6-23 and G6-31.

VEGF-C, a member of the VEGF family, is known to bind at least two cell surface receptor families, the tyrosine kinase VEGF receptors and the neuropilin (Nrp) receptors. Of the three VEGF receptors, VEGF-C can bind VEGFR2 (KDR receptor) and VEGFR3 (Flt-4 receptor) leading to receptor dimerization (Shinkai et al., *J Biol Chem* 273, 31283-31288 (1998)), kinase activation and autophosphorylation (Heldin, *Cell* 80, 213-223 (1995); Waltenberger et al., *J. Biol Chem* 269, 26988-26995 (1994)). The phosphorylated receptor induces the activation of multiple substrates leading to angiogenesis and lymphangiogenesis (Ferrara et al., *Nat Med* 9, 669-676 (2003)).

VEGF-C is one of the best studied mediators of lymphatic development. Overexpression of VEGF-C in tumor cells was shown to promote tumor-associated lymphangiogenesis, resulting in enhanced metastasis to regional lymph nodes (Karpanen et al., *Faseb J* 20, 1462-1472 (2001); Mandriota et al., *EMBO J* 20, 672-682 (2001); Skobe et al., *Nat Med* 7, 192-198 (2001); Stacker et al., *Nat Rev Cancer* 2, 573-583 (2002); Stacker et al., *Faseb J* 16, 922-934 (2002)). VEGF-C expression has also been correlated with tumor-associated lymphangiogenesis and lymph node metastasis for a number of human cancers (reviewed in Achen et al., 2006, supra. In addition, blockade of VEGF-C-mediated signaling has been shown to suppress tumor lymphangiogenesis and lymph node metastases in mice (Chen et al., Cancer Res 65, 9004-9011 (2005); He et al., *J. Natl Cancer Inst* 94, 8190825 (2002); Krishnan et al., Cancer Res 63, 713-722 (2003); Lin et al., *Cancer Res* 65, 6901-6909 (2005)).

The terms "vascular endothelial growth factor-C", "VEGF-C", "VEGFC", "VEGF-related protein", "VRP", "VEGF2" and "VEGF-2" are used interchangeably, and refer to the full-length polypeptide and/or the active fragments of the full-length polypeptide. In one embodiment, active fragments include any portions of the full-length amino acid sequence which have less than the full 419 amino acids of the full-length amino acid sequence as shown in SEQ ID NO:87. Such active fragments contain VEGF-C biological activity and include, but not limited to, mature VEGF-C. In one embodiment, the full-length VEGF-C polypeptide is proteolytically processed produce a mature form of VEGF-C polypeptide, also referred to as mature VEGF-C. Such processing includes cleavage of a signal peptide and cleavage of an amino-terminal peptide (corresponding approximately to amino acids 1-102 of SEQ ID NO:87) and cleavage of a carboxyl-terminal peptide (corresponding approximately to amino acids 228-419 of SEQ ID NO:87) to produced a fully-processed mature form (see FIG. 6). Experimental evidence demonstrates that the full-length VEGF-C, partially-processed forms of VEGF-C and fully processed mature forms of VEGF-C are able to bind VEGFR3 (Flt-4 receptor). However, high affinity binding to VEGFR2 occurs only with the fully processed mature forms of VEGF-C.

The term "VEGF-C" also refers to VEGF-C from non-human species such as mouse, rat or primate. Sometimes the VEGF-C from a specific species are indicated by terms such as hVEGF-C for human VEGF-C, mVEGF-C for murine VEGF-C, and etc.

The terms "C137S", "VEGF-C C137S", "vascular endothelial growth factor-C C137S", "VEGFC C137S" and "hVEGF-C C137S" are used interchangeably, and refer to the full-length polypeptide and the fragments of the full-length polypeptide wherein the cystein residue at amino acid residue position 137 was replaced by a serine residue as shown in SEQ ID NO:88.

The term "VEGF-C antagonist" is used herein to refer to a molecule capable of neutralizing, blocking, inhibiting, abrogating, reducing or interfering with VEGF-C activities. In certain embodiments, VEGF-C antagonist refers to a molecule capable of neutralizing, blocking, inhibiting, abrogating, reducing or interfering with the ability of VEGF-C to modulate angiogenesis, lymphatic endothelial cell (EC) migration, proliferation or adult lymphangiogenesis, especially tumoral lymphangiogenesis and tumor metastasis. VEGF-C antagonists include, without limitation, anti-VEGF-C antibodies and antigen-binding fragments thereof, receptor molecules and derivatives which bind specifically to VEGF-C thereby sequestering its binding to one or more receptors, anti-VEGF-C receptor antibodies and VEGF-C receptor antagonists such as small molecule inhibitors of the VEGFR2 and VEGFR3. The term "VEGF-C antagonist," as used herein, specifically includes molecules, including antibodies, antibody fragments, other binding polypeptides, peptides, and non-peptide small molecules, that bind to VEGF-C and are capable of neutralizing, blocking, inhibiting, abrogating, reducing or interfering with VEGF-C activities. Thus, the term "VEGF-C activities" specifically includes VEGF-C mediated biological activities (as hereinabove defined) of VEGF-C.

The term "anti-VEGF-C antibody" or "an antibody that binds to VEGF-C" refers to an antibody that is capable of binding VEGF-C with sufficient affinity such that the antibody is useful as a diagnostic and/or therapeutic agent in targeting VEGF-C. In one embodiment, the extent of binding of an anti-VEGF-C antibody to an unrelated, non-VEGF-C protein is less than about 10% of the binding of the antibody to VEGF-C as measured, e.g., by a radioimmunoassay (RIA). In certain embodiments, an antibody that binds to VEGF-C has a dissociation constant (Kd) of ≤1 µM, ≤100 nM, ≤10 nM, ≤1 nM, or ≤0.1 nM. In certain embodiments, an anti-VEGF-C antibody binds to an epitope of VEGF-C that is conserved among VEGF-C from different species.

The term "biological activity" and "biologically active" with regard to a VEGF-C polypeptide refer to physical/chemical properties and biological functions associated with full-length and/or mature VEGF-C. In some embodiments, VEGF-C "biological activity" means having the ability to bind to, and stimulate the phosphorylation of, the Flt-4 receptor (VEGFR3). Generally, VEGF-C will bind to the extracellular domain of the Flt-4 receptor and thereby activate or inhibit the intracellular tyrosine kinase domain thereof. Consequently, binding of VEGF-C to the receptor may result in enhancement or inhibition of proliferation and/or differentiation and/or activation of cells having the Flt-4 receptor for the VEGF-C in vivo or in vitro. Binding of VEGF-C to the Flt-4 receptor can be determined using conventional techniques, including competitive binding methods, such as RIAs, ELISAs, and other competitive binding assays. Ligand/receptor complexes can be identified using such separation methods as filtration, centrifugation, flow cytometry (see, e.g., Lyman et al., *Cell,* 75:1157-1167 [1993]; Urdal et al., *J. Biol. Chem.,* 263:2870-2877 [1988]; and Gearing et al., *EMBO J.,* 8:3667-3676 [1989]), and the like. Results from binding studies can be analyzed using any conventional graphical representation of the binding data, such as Scatchard analysis (Scatchard, *Ann. NY Acad. Sci.,* 51:660-672 [1949]; Goodwin et al., *Cell,* 73:447-456 [1993]), and the like. Since VEGF-C induces phosphorylation of the Flt-4 receptor, conventional tyrosine phosphorylation assays can also be used as an indication of the formation of a Flt-4 receptor/VEGF-C complex. In another embodiment, VEGF-C "biological activity" means having the ability to bind to KDR receptor (VEGFR2). vascular permeability, as well as the migration and proliferation of endothelial cells. In certain embodiments, binding of VEGF-C to the KDR receptor may result in enhancement or inhibition of vascular permeability as well as migration and/or proliferation and/or differentiation and/or activation of endothelial cells having the KDR receptor for the VEGF-C in vivo or in vitro.

As used herein, "treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder or to slow the progression of a disease or disorder.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

A "disorder" is any condition that would benefit from treatment. For example, mammals who suffer from or need prophylaxis against abnormal angiogenesis (excessive, inappropriate or uncontrolled angiogenesis) or vascular permeability. This includes chronic and acute disorders or diseases including those pathological conditions which predispose the mammal to the disorder in question. Non-limiting examples of disorders to be treated herein include malignant and benign tumors; non-leukemias and lymphoid malignancies; and, in particular, tumor (cancer) metastasis.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from the group consisting of small cell lung cancer, glioblastoma, neuroblastomas, melanoma, breast carcinoma, gastric cancer, colorectal cancer (CRC), and hepatocellular carcinoma. Yet, in some embodiments, the cancer is selected from the group consisting of non-small cell lung cancer, colorectal cancer, renal cancer, ovarian cancer, glioblastoma and breast carcinoma, including metastatic forms of those cancers.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream or lymphatics, and stopping at a distant site. At the new site, the cells establish a blood supply and can grow to form a life-threatening mass. In certain embodiments, the term metastatic tumor refers to a tumor that is capable of metastasizing, but has not yet metastasized to tissues or organs elsewhere in the body. In certain embodiments, the term metastatic tumor refers to a tumor that has metastasized to tissues or organs elsewhere in the body.

The "metastatic organ" or "metastatic tissue" is used in the broadest sense, refers to an organ or a tissue in which the cancer cells from a primary tumor or the cancer cells from another part of the body have spread. Examples of metastatic organ and metastatic tissue include, but not limited to, lung, liver, brain, ovary, bone and bone marrow.

The "pre-metastatic organ" or "pre-metastatic tissue" as used herein, refers to an organ or a tissue in which no cancer cells from a primary tumor or from another part of the body have been detected. In certain embodiments, the pre-metastatic organ or pre-metastatic tissue as used herein, refers to an organ or tissue that is in the phase before the spread of cancer cells from a primary tumor or from another part of the body to this organ or tissue have occurred. Examples of pre-metastatic organ or pre-metastatic tissue include, but not limited to, lung, liver, brain, ovary, bone and bone marrow.

By "primary tumor" or "primary cancer" is meant the original cancer and not a metastatic lesion located in another tissue, organ, or location in the subject's body.

"Cancer recurrence" herein refers to a return of cancer following treatment, and includes return of cancer in the primary organ, as well as distant recurrence, where the cancer returns outside of the primary organ.

By "tumor burden" is meant the number of cancer cells, the size of a tumor, or the amount of cancer in the body. Tumor burden is also referred to as tumor load.

By "tumor number" is meant the number of tumors.

"Refractory" refers to the resistance or non-responsiveness of a disease or condition to a treatment (e.g., the number of neoplastic plasma cells increases even though treatment if given). In certain embodiments, the term "refractory" refers a resistance or non-responsiveness to any previous treatment including, but not limited to, VEGF antagonist, anti-angiogenic agents and chemotherapy treatments. In certain embodiments, the term "refractory" refers an intrinsically non-responsiveness of a disease or condition to any previous treatment comprising a VEGF antagonist, anti-angiogenic agents and/or chemotherapy treatments. In certain embodiments, the VEGF antagonist is an anti-VEGF antibody.

"Relapsed" refers to the regression of the patient's illness back to its former diseased state, especially the return of symptoms following an apparent recovery or partial recovery. In certain embodiments, relapsed state refers to the process of returning to or the return to illness before the previous treatment including, but not limited to, VEGF antagonist, anti-angiogenic agents and/or chemotherapy treatments. In certain embodiments, relapsed state refers to the process of returning to or the return to illness after an initial strong response to a cancer therapy comprising a VEGF antagonist, anti-angiogenic agents and/or chemotherapy treatments. In certain embodiments, the VEGF antagonist is an anti-VEGF antibody.

The term "anti-cancer therapy" or "cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenic agents, apoptotic agents, anti-tubulin agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), Erbitux® (cetuximab, Imclone), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "sample" or "biological sample" as used herein, refers to a composition that is obtained or derived from a subject of interest that contains a cellular and/or other molecular entity that is to be characterized and/or identified, for example based on physical, biochemical, chemical and/or physiological characteristics. In certain embodiments, the definition encompasses blood and other liquid samples of biological origin and tissue samples such as a biopsy specimen or tissue cultures or cells derived therefrom. The source of the tissue sample may be solid tissue as from a fresh, frozen and/or preserved organ or tissue sample or biopsy or aspirate;

blood or any blood constituents; bodily fluids; and cells from any time in gestation or development of the subject or plasma.

In another embodiment, the definition includes biological samples that have been manipulated in any way after their procurement, such as by treatment with reagents, solubilization, or enrichment for certain components, such as proteins or polynucleotides, or embedding in a semi-solid or solid matrix for sectioning purposes. In certain embodiments, a "section" of a tissue sample is meant a single part or piece of a tissue sample, e.g. a thin slice of tissue or cells cut from a tissue sample.

Samples include, but not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, tumor lysates, and tissue culture medium, as well as tissue extracts such as homogenized tissue, tumor tissue, and cellular extracts.

In one embodiment, the sample is a clinical sample. In another embodiment, the sample is used in a diagnostic assay. In certain embodiments, the sample is obtained from a pre-metastatic organ or a pre-metastatic tissue. In certain embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood.

In certain embodimenst, a sample is obtained from a subject or patient prior to treatment with anti-VEGF-C antibodies. In certain embodimenst, a sample is obtained from a subject or patient after the treatment with anti-VEGF-C antibodies. In certain embodiments, a sample is obtained from a subject or patient prior to VEGF antagonist therapy. In certain embodiments, a sample is obtained from a subject or patient prior to anti-VEGF antibody therapy. In certain embodiments, a sample is obtained before a cancer has metastasized. In certain embodiments, a sample is obtained after a cancer has metastasized.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

The term "efficacy" is used herein in the broadest sense and refers to immunoglobuin's, antibody's or Fc fusion protein's ability to produce a desired effect. In certain embodiments, efficacy refers to the maximal observed effect of an immunoglobulin, antibody or Fc fusion protein at saturating levels. In certain embodiments, efficacy refers to the $EC_{50}$ of an immunoglobulin, antibody or Fc fusion protein. In certain embodiments, efficacy refers to the potency of an immunoglobulin, antibody or Fc fusion protein. In certain embodiments, efficacy refers to immunoglobulin's, antibody's or Fc fusion protein's ability to produce beneficial effects on the course or duration of a disease, including clinical benefit as defined herein.

The term "$EC_{50}$" refers to the concentration of an immunoglobulin, antibody or Fc fusion protein which induces a response halfway between the baseline and maximum. In certain embodiments, $EC_{50}$ represents the concentration of an immunoglobulin, antibody or Fc fusion protein where 50% of its maximal effect is observed. In certain embodiments, $EC_{50}$ represents the plasma or serum concentration required for obtaining 50% of the maximum effect in vivo.

Efficacy in treating cancer may be demonstrated by detecting the ability of an antibody, a fusion protein, a conjugated molecule, or a composition of the invention to inhibit or reduce the growth or metastasis of cancerous cells or to ameliorate or alleviate one or more symptoms associated with cancer. The treatment is considered therapeutic if there is, for example, a reduction in the growth or metastasis of cancerous cells, amelioration of one or more symptoms associated with cancer, or a decrease in mortality and/or morbidity following administration of an antibody, a fusion protein, a conjugated molecule, or a composition of the invention. Antibodies, fusion proteins or compositions of the invention can be tested for their ability to reduce tumor formation in in vitro, ex vivo, and in vivo assays. For cancer therapy, efficacy in vivo can, for example, be also measured by assessing the duration of survival, time to disease progression (TTP), the response rates (RR), duration of response, and/or quality of life.

Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

"Adjuvant therapy" herein refers to therapy given after surgery, where no evidence of residual disease can be detected, so as to reduce the risk of disease recurrence. The goal of adjuvant therapy is to prevent recurrence of the cancer, and therefore to reduce the chance of cancer-related death.

Administration "in combination with" one or more further therapeutic agents includes simultaneous (concurrent) and consecutive administration in any order.

The term "simultaneously" or "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

The term "pharmaceutical formulation" refers to a preparation which is in such form as to permit the biological activity of the active ingredient to be effective, and which contains no additional components which are unacceptably toxic to a subject to which the formulation would be administered. Such formulations may be sterile.

A "sterile" formulation is aseptic or free from all living microorganisms and their spores.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug (such as a VEGF-C polypeptide or antibody thereto) to a mammal. The components of the liposome are commonly arranged in a bilayer formation, similar to the lipid arrangement of biological membranes.

The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; pemetrexed (ALIMTA®); gemcitabine (GEMZAR®); anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATINT™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

A "growth inhibitory agent" when used herein refers to a compound or composition which inhibits growth of a cell (such as a cell expressing VEGF-C or cells acted upon by VEGF-C) either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman (1986) "Prodrugs in Cancer Chemotherapy" *Biochemical Society Transactions,* 14, pp. 375-382, 615th Meeting Belfast and Stella et al. (1985). "Prodrugs: A Chemical Approach to Targeted Drug Delivery," *Directed Drug Delivery*, Borchardt et al, (ed.), pp. 247-267, Humana Press. The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "small molecule" is defined herein to have a molecular weight below about 500 Daltons.

"Purified" means that a molecule is present in a sample at a concentration of at least 95% by weight, or at least 98% by weight of the sample in which it is contained.

An "isolated" nucleic acid molecule is a nucleic acid molecule that is separated from at least one other nucleic acid molecule with which it is ordinarily associated, for example, in its natural environment. An isolated nucleic acid molecule further includes a nucleic acid molecule contained in cells that ordinarily express the nucleic acid molecule, but the nucleic acid molecule is present extrachromosomally or at a chromosomal location that is different from its natural chromosomal location.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O) OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Cancer recurrence" herein refers to a return of cancer following treatment. In one embodiment, cancer recurrence includes return of cancer in the breast, as well as distant recurrence, where the cancer returns outside of the breast.

Compositions of the Invention

A key event in the multi-step process of metastasis involves the egress of a tumor cell away from the primary tumor mass. For solid tumors, the lymphatic system often provides a route for the departing cells. VEGF-C is known to be a key modulator of angiogenesis, lymphangiogenesis and metastasis in many tumor models, and inhibition of the VEGF-C axis is considered a promising strategy for inhibiting the development of metastasis.

The studies underlying the present invention, which are presented in the examples below, support an important role of VEGF-C in angiogenesis, tumor lymphangiogenesis and metastasis. Additionally, the data set forth in the Examples demonstrate the presence of functional lymphatic vessels within tumors and show that treating with anti-VEGF-C results in a reduction of these functional lymphatics. See also FIGS. 7-9, 12-14 and 22

The invention encompasses isolated antibody and polynucleotide embodiments. In one embodiment, an anti-VEGF-C antibody is purified.

This invention also encompasses compositions, including pharmaceutical compositions, comprising an anti-VEGF-C antibody; and polynucleotides comprising sequences encoding an anti-VEGF-C antibody. As used herein, compositions comprise one or more antibodies that bind to VEGF-C, and/or one or more polynucleotides comprising sequences encoding one or more antibodies that bind to VEGF-C. These compositions may further comprise suitable carriers, such as pharmaceutically acceptable excipients including buffers, which are well known in the art.

In one embodiment, the anti-VEGF-C antibodies of the invention are monoclonal. In yet another embodiment, the anti-VEGF-C antibodies are polyclonal. Also encompassed within the scope of the invention are Fab, Fab', Fab'-SH and F(ab')$_2$ fragments of the anti-VEGF-C antibodies provided herein. These antibody fragments can be created by traditional means, such as enzymatic digestion, or may be generated by recombinant techniques. Such antibody fragments may be chimeric or humanized. These fragments are useful for the diagnostic and purposes set forth below. In one embodiment, an anti-VEGF-C antibody is a chimeric, humanized, or human antibody.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

Exemplary monoclonal antibodies derived from a phage library are provided herein and described in Example 1. Those antibodies include, but not limited to VC1, VC1.1, VC1.2, VC1.3, VC1.4, VC1.5, VC1.6, VC1.7, VC1.8, VC1.9, VC1.10, VC1.11, VC1.12, VC1.12.1, VC1.12.2, VC1.12.3, VC1.12.4, VC1.12.5, VC1.12.6, VC1.12.8, VC1.12.9, VC1.12.10, VC3, VC4, VC4.2, VC4.3, VC4.4, VC4.5. The sequences of the heavy and light chain variable domains of VC1, VC1.1, VC1.2, VC1.3, VC1.4, VC1.5, VC1.6, VC1.7, VC1.8, VC1.9, VC1.10, VC1.11, VC1.12, VC1.12.1, VC1.12.2, VC1.12.3, VC1.12.4, VC1.12.5, VC1.12.6, VC1.12.8, VC1.12.9, VC1.12.10, VC3, VC4, VC4.2, VC4.3, VC4.4, VC4.5 are shown in FIG. 1*a-f*. The sequences of the heavy and light chain variable domains of anti-VEGF-C antibodies are also shown in FIGS. 23-30 and 38-39.

The HVR-H3 sequences of antibodies VC1, VC1.1, VC1.2, VC1.3, VC1.4, VC1.5, VC1.6, VC1.7, VC1.8, VC1.9, VC1.10, VC1.11, VC1.12, VC1.12.1, VC1.12.2, VC1.12.3, VC1.12.4, VC1.12.5, VC1.12.6, VC1.12.8, VC1.12.9, VC1.12.10 have no amino acid residues at positions 100a, 100b, 100c, 100d and 100e. The HVR-H3 sequence of antibody VC3 has no amino acid residue at position 100d. See also FIGS. 24, 28 and 30.

In certain embodiments, the monoclonal antibodies that binds to VEGF-C or a fragment described herein further comprises an amino acid substitution at position 297 to alanine. In certain embodiments, the monoclonal antibodies that binds to VEGF-C or a fragment described herein further comprises an amino acid substitution at position 297 to alanine and at position 265 to alanine. In certain embodiments, anti-VEGF-C antibody VC4.5 comprises the amino acid substitution at position 297 with alanine. In certain embodiments, anti-VEGF-C antibody VC4.5 comprises the amino acid substitution at position 297 with alanine and at position 265 to alanine. In certain embodiments, anti-VEGF-C antibodies VC1.12.1, VC1.12.4 and VC1.12.9 comprise the amino acid substitution at position 297 with alanine. In certain embodiments, anti-VEGF-C antibodies VC1.12.1, VC1.12.4 and VC1.12.9 comprise the amino acid substitution at position 297 with alanine and at position 265 to alanine. In certain embodiments, antibodies comprising amino acid substitions at positions 265 and 297 with alanine are referred to as "DANA".

To screen for antibodies which bind to a particular epitope on the antigen of interest, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al. (1995) *J. Biol. Chem.* 270:1388-1394, can be performed to determine whether the antibody binds an epitope of interest. Further exemplary embodiments of anti-VEGF-C antibodies are provided below.

Specific Embodiments of Anti-VEGF-C Antibodies

The amino acid sequences of SEQ ID NOs:1 to 39 are numbered with respect to individual HVR (i.e., H1, H2 or H3) as indicated in FIG. 1*a-f*, the numbering being consistent with the Kabat numbering system as described herein.

In one aspect, the invention provides an antibody comprising a HVR-H1 region comprising the sequence of SEQ ID NO:1, SEQ ID NO:2, SEQ ID NO:3 or SEQ ID NO:4. In one aspect, the invention provides an antibody comprising a HVR-H2 region comprising the sequence of SEQ ID NO:5, SEQ ID NO:6, SEQ ID NO:7 or SEQ ID NO:8. In one aspect, the invention provides an antibody comprising a HVR-H3 region comprising the sequence of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26.

In one embodiment, the invention provides an antibody comprising a HVR-H1 region comprising the sequence of SEQ ID NO:1, and a HVR-H2 region comprising the sequence of SEQ ID NO:6. In one embodiment, the invention provides an antibody comprising a HVR-H1 region comprising the sequence of SEQ ID NO:1, and a HVR-H3 region comprising the sequence of SEQ ID NO:21. In one embodiment, the invention provides an antibody comprising a HVR-H2 region comprising the sequence of SEQ ID NO:6, and a HVR-H3 region comprising the sequence of SEQ ID NO:21. In one embodiment, the invention provides an antibody comprising a HVR-H1 region comprising the sequence of SEQ ID NO:1, a HVR-H2 region comprising the sequence of SEQ ID NO:6, and a HVR-H3 region comprising the sequence of SEQ ID NO:21.

In one embodiment, the invention provides an antibody comprising a HVR-H1 region comprising the sequence of SEQ ID NO:3, and a HVR-H2 region comprising the sequence of SEQ ID NO:8. In one embodiment, the invention provides an antibody comprising a HVR-H1 region comprising the sequence of SEQ ID NO:3, and a HVR-H3 region comprising the sequence of SEQ ID NO:26. In one embodiment, the invention provides an antibody comprising a HVR-H2 region comprising the sequence of SEQ ID NO:8, and a HVR-H3 region comprising the sequence of SEQ ID NO:26. In one embodiment, the invention provides an antibody comprising a HVR-H1 region comprising the sequence of SEQ ID NO:3, a HVR-H2 region comprising the sequence of SEQ ID NO:8, and a HVR-H3 region comprising the sequence of SEQ ID NO:26.

In one aspect, the invention provides an antibody comprising at least one, at least two, or all three of the following:
  (i) a HVR-H1 sequence comprising the sequence of SEQ ID NO:1;
  (ii) a HVR-H2 sequence comprising the sequence of SEQ ID NO:6;
  (iii) a HVR-H3 sequence comprising the sequence of SEQ ID NO:21.

In one aspect, the invention provides an antibody comprising at least one, at least two, or all three of the following:
  (i) a HVR-H1 sequence comprising the sequence of SEQ ID NO:3;
  (ii) a HVR-H2 sequence comprising the sequence of SEQ ID NO:8;
  (iii) a HVR-H3 sequence comprising the sequence of SEQ ID NO:26.

In one aspect, the invention provides an antibody comprising at least one, at least two, or all three of the following:
  (i) a HVR-L1 sequence comprising the sequence of SEQ ID NO:27;
  (ii) a HVR-L2 sequence comprising the sequence of SEQ ID NO:28;
  (iii) a HVR-L3 sequence comprising the sequence of SEQ ID NO:29.

In one aspect, the invention provides an antibody comprising at least one, at least two, or all three of the following:
  (i) a HVR-L1 sequence comprising the sequence of SEQ ID NO:27;
  (ii) a HVR-L2 sequence comprising the sequence of SEQ ID NO:28;
  (iii) a HVR-L3 sequence comprising the sequence of SEQ ID NO:30.

In one aspect, the invention provides an antibody comprising at least one, at least two, or all three of the following:
  (i) a HVR-L1 sequence comprising the sequence of SEQ ID NO:27;
  (ii) a HVR-L2 sequence comprising the sequence of SEQ ID NO:28;
  (iii) a HVR-L3 sequence comprising the sequence of SEQ ID NO:33.

In one aspect, the invention provides an antibody comprising at least one, at least two, or all three of the following:
  (i) a HVR-L1 sequence comprising the sequence of SEQ ID NO:27;
  (ii) a HVR-L2 sequence comprising the sequence of SEQ ID NO:28;
  (iii) a HVR-L3 sequence comprising the sequence of SEQ ID NO:37.

In one aspect, the invention provides antibodies comprising heavy chain HVR sequences as depicted in FIG. 1A-C. In one embodiment, the invention provides antibodies comprising heavy chain sequence SEQ ID NO:73 or SEQ ID NO:84.

In another aspect, the invention provides antibodies comprising light chain HVR sequences as depicted in FIG. 1D-F. In one embodiment, the invention provides antibodies comprising light chain sequence SEQ ID NO:74, SEQ ID NO:75, SEQ ID NO:76, SEQ ID NO:77, SEQ ID NO:78, SEQ ID NO:79, SEQ ID NO:80. SEQ ID NO:81, SEQ ID NO:82, SEQ ID NO:83 or SEQ ID NO:85.

In another aspect of the invention, any anti-VEGF-C antibody of the invention described herein, amino acid asparagine at position 297 is substituted with amino acid alanine. I another embodiment, amino acid aspartic acid at position 265 is substituted with amino acid alanine. In one embodiment, the antibody further comprises heavy chain sequence SEQ ID NO:73 or SEQ ID NO:84. In another embodiment, the antibody further comprises light chain HVR sequences as depicted in FIG. 1D-F. In another embodiment, the antibody further comprises light chain sequence SEQ ID NO:74, SEQ ID NO:75, SEQ ID NO:76, SEQ ID NO:77, SEQ ID NO:78, SEQ ID NO:79, SEQ ID NO:80. SEQ ID NO:81, SEQ ID NO:82, SEQ ID NO:83 or SEQ ID NO:85.

In certain embodiments, the antibodies of the invention comprise a light chain variable domain of humanized 4D5 antibody (huMAb4D5-8) (HERCEPTIN®, Genentech, Inc., South San Francisco, Calif., USA) (also referred to in U.S. Pat. No. 6,407,213 and Lee et al., J. Mol. Biol. (2004), 340 (5):1073-93) as depicted in SEQ ID NO:71 below.

```
                                                       (SEQ ID NO: 71)
¹Asp Ile Gln Met Thr Gln Ser Pro Ser Ser Leu Ser Ala Ser Val Gly Asp Arg

Val Thr Ile Thr Cys Arg Ala Ser Gln Asp Val Asn Thr Ala Val Ala Trp Tyr

Gln Gln Lys Pro Gly Lys Ala Pro Lys Leu Leu Ile Tyr Ser Ala Ser Phe Leu

Tyr Ser Gly Val Pro Ser Arg Phe Ser Gly Ser Arg Ser Gly Thr Asp Phe Thr

Leu Thr Ile Ser Ser Leu Gln Pro Glu Asp Phe Ala Thr Tyr Tyr Cys Gln Gln

His Tyr Thr Thr Pro Pro Thr Phe Gly Gln Gly Thr Lys Val Glu Ile Lys¹⁰⁷
(HVR residues are underlined)
```

In one embodiment, the huMAb4D5-8 light chain variable domain sequence is modified at one or more of positions 30, 66 and 91 (Asn, Arg and His as indicated in bold/italics above, respectively). In one embodiment, the modified huMAb4D5-8 sequence comprises Ser in position 30, Gly in position 66 and/or Ser in position 91. Accordingly, in one embodiment, an antibody of the invention comprises a light chain variable domain comprising the sequence depicted in SEQ ID NO:72 below:

```
                                                       (SEQ ID NO: 72)
¹Asp Ile Gln Met Thr Gln Ser Pro Ser Ser Leu Ser Ala Ser Val Gly Asp Arg

Val Thr Ile Thr Cys Arg Ala Ser Gln Asp Val Ser Thr Ala Val Ala Trp Tyr

Gln Gln Lys Pro Gly Lys Ala Pro Lys Leu Leu Ile Tyr Ser Ala Ser Phe Leu

Tyr Ser Gly Val Pro Ser Arg Phe Ser Gly Ser Gly Ser Gly Thr Asp Phe Thr

Leu Thr Ile Ser Ser Leu Gln Pro Glu Asp Phe Ala Thr Tyr Tyr Cys Gln Gln

Ser Tyr Thr Thr Pro Pro Thr Phe Gly Gln Gly Thr Lys Val Glu Ile Lys¹⁰⁷
(HVR residues are underlined)
```

Substituted residues with respect to huMAb4D5-8 are indicated in bold/italics above.

Antibodies of the invention can comprise any suitable framework variable domain sequence, provided binding activity to VEGF-C is substantially retained. For example, in some embodiments, antibodies of the invention comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-93). In one embodiment, these antibodies further comprise a human I light chain framework consensus sequence. In one embodiment, these antibodies comprise light chain HVR sequences of huMAb4D5-8 as described in U.S. Pat. Nos. 6,407,213 & 5,821,337). In one embodiment, these antibodies comprise light chain variable domain sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-93).

In one embodiment, an antibody of the invention comprises a heavy chain variable domain, wherein the framework sequence comprises the sequences of SEQ ID NOs:40, 41, 42, 43, 44, 45, 46, 47, 48, 49, 50, 51, 52, 53, 54, 55, 56, 57, or 58 (FIGS. 2A and 2B), and HVR H1, H2 and H3 sequences are SEQ ID NOS:1, 6 and/or 21, respectively. In one embodiment, an antibody of the invention comprises a light chain variable domain, wherein the framework sequence comprises the sequences of SEQ ID NOs:59, 60, 61 or 62 (FIG. 3), HVR L1 and L2 sequences are SEQ ID NOS:27 and 28, respectively, and HVR L3 sequence is SEQ ID NOs:30, 31, 32, 33, 34, 35, 36, 37 or 38, respectively.

In one embodiment, an antibody of the invention comprises a heavy chain variable domain, wherein the framework sequence comprises the sequences of SEQ ID NOs:40, 41, 42, 43, 44, 45, 46, 47, 48, 49, 50, 51, 52, 53, 54, 55, 56, 57, or 58, and HVR H1, H2 and H3 sequences are SEQ ID NOs:3, 8 and 26, respectively. In one embodiment, an antibody of the invention comprises a light chain variable domain, wherein the framework sequence comprises the sequences of SEQ ID NOs:59, 60, 61 andor 62, and HVR L1, L2 and L3 sequences are SEQ ID NOs:27, 28 and 29, respectively.

In one embodiment, an antibody of the invention comprises a heavy chain variable domain comprising the sequence of SEQ ID NO:73. In one embodiment, an antibody of the invention comprises a light chain variable domain comprising the sequence of SEQ ID NOs:74, 75, 76, 77, 78, 79, 80, 81, 82 or 83. In one embodiment, an antibody of the invention comprises a heavy chain variable domain comprising the sequence of SEQ ID NO:84 and a light chain variable domain comprising the sequence of SEQ ID NO:85.

In one aspect, the invention provides an antibody that competes with any of the above-mentioned antibodies for binding to VEGF-C. In another aspect, the invention provides an antibody that binds to the same epitope on VEGF-C as any of the above-mentioned antibodies.

Antibody Fragments

The present invention encompasses antibody fragments. Antibody fragments may be generated by traditional means, such as enzymatic digestion, or by recombinant techniques.

In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA,* 89:4285; Presta et al. (1993) *J. Immunol.,* 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90: 2551 (1993); Jakobovits et al., *Nature,* 362: 255 (1993); Bruggermann et al., *Year in Immunol.,* 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Multispecific Antibodies

One example of a multispecific antibody of this invention includes an antibody that binds to VEGF-C and to another antigen. In other embodiments, multispecific antibodies may bind to two different epitopes of VEGF-C. Multispecific antibodies may also be used to localize cytotoxic agents to cells which express VEGF-C. These antibodies possess a VEGF-C-binding arm and an arm which binds a cytotoxic agent, such as, e.g., saporin, anti-interferon-α, vinca alkaloid, ricin A chain, methotrexate or radioactive isotope hapten. Multispecific antibodies can be prepared as full length antibodies or antibody fragments (e.g. F(ab')$_2$ bispecific antibodies).

Various methods for making bispecific antibodies have been described in the art. One of the first approaches involved co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different approach, antibody variable domains are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1) is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, "knob-into-hole" or "KnH" technology refers to a technology that directs the pairing of two polypeptides together in vitro or in vivo by introducing a pertuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (e.g., US20007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. According to one embodiment, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Multipecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents and techniques are known (e.g., U.S. Pat. No. 4,676,980).

Techniques for generating multispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments can be recovered from E. coli and can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6- fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, an anti-VEGF-C antibody variant comprises an Fc region with an amino substitution at position 297.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-92 (1991). Non-limiting examples of in vitro assays to assess ADCC activity of a molecule of interest is described in U.S. Pat. No. 5,500,362 (see, e.g. Hellstrom, I., et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. MountainView, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). Clq binding assays may also be carried out to confirm that the antibody is unable to bind Clq and hence lacks CDC activity. To assess complement activation, a CDC assaymay be performed (see, for example, Gazzano-Santoro et al., *J. Immunol. Methods* 202: 163 (1996); Cragg, M. S. et al., *Blood* 101:1045-1052 (2003); and Cragg, M. S, and M. J. Glennie, *Blood* 103:2738-2743 (2004)). FcRn binding and in vivo clearance/half life determinations can also be performed using methods known in the art (see, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes. Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter, Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region.

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005)*Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) *Adv. Drug Deliv. Rev.* 26:151-172; U.S. Pat. No. 4,975,278). Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., *Lancet* (Mar. 15, 1986) pp. 603-05; Thorpe (1985) "Antibody Carriers Of Cytotoxic Agents In Cancer Therapy: A Review," in *Monoclonal Antibodies '84: Biological And Clinical Applications* (A. Pinchera et al., eds) pp. 475-506. Both polyclonal antibodies and monoclonal antibodies have been reported as useful in these strategies (Rowland et al., (1986) *Cancer Immunol. Immunother.* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al (1998) *Cancer Res.* 58:2928; Hinman et al (1993) *Cancer Res.* 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) *Eur. Jour. Nucl. Med.* 27(7):766-77; Wiseman et al (2002) *Blood* 99(12):4336-42; Witzig et al (2002) *J. Clin. Oncol.* 20(10):2453-63; Witzig et al (2002) *J. Clin. Oncol.* 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (*Drugs of the Future* (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) *Nature Biotechnol.* 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC 1065, and the derivatives of these toxins that have toxin activity, are also contemplated herein.

Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983, 340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α3I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad\qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC'), and N-Succinimidyl (4-iodo-acetyl)aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Certain Methods of Making Antibodies
Certain Hybridoma-Based Methods

Monoclonal antibodies of the invention can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4):265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide comprising VEGF-C or a fragment thereof, and an adjuvant, such as monophosphoryl lipid A (MPL)/trehalose dicrynomycolate (TDM) (Ribi Immunochem. Research, Inc., Hamilton, Mont.). A polypeptide comprising VEGF-C or a fragment thereof may be prepared using methods well known in the art, such as recombinant methods, some of which are further described herein. Serum from immunized animals is assayed for anti-VEGF-C antibodies, and booster immunizations are optionally administered. Lymphocytes from animals producing anti-VEGF-C antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001

(1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to VEGF-C. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

Certain Library Screening Methods

Antibodies of the invention can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., *J. Mol. Biol.* (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the invention can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-VEGF-C clones is desired, the subject is immunized with VEGF-C to generate an antibody response, and spleen cells and/or circulating B cells other peripheral blood lymphocytes (PBLs) are recovered for library construction. In a preferred embodiment, a human antibody gene fragment library biased in favor of anti-VEGF-C clones is obtained by generating an anti-VEGF-C antibody response in transgenic mice carrying a functional human immunoglobulin gene array (and lacking a functional endogenous antibody production system) such that VEGF-C immunization gives rise to B cells producing human antibodies against VEGF-C. The generation of human antibody-producing transgenic mice is described below.

Additional enrichment for anti-VEGF-C reactive cell populations can be obtained by using a suitable screening procedure to isolate B cells expressing VEGF-C-specific membrane bound antibody, e.g., by cell separation using VEGF-C affinity chromatography or adsorption of cells to fluorochrome-labeled VEGF-C followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which VEGF-C is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (*USA*), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature,* 341: 544-546 (1989). However, for amplifying from cDNA, back primers can also be based in the leader exon as described in Jones et al., *Biotechnol.,* 9: 88-89 (1991), and forward primers within the constant region as described in Sastry et al., *Proc. Natl. Acad. Sci.* (*USA*), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.,* 222: 581-597 (1991) or as described in the method of Orum et al., *Nucleic Acids Res.,* 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.,* 227: 776-798 (1992)), and mapped (reported in Matsuda et al., *Nature Genet.,* 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.,* 227: 381-388 (1992). VH repertoires can also be made with all the sequence diversity focused in a long H3 loop of a single length as described in Barbas et al., *Proc. Natl. Acad. Sci. USA,* 89: 4457-4461 (1992). Human Vκ and Vλ segments have been cloned and sequenced (reported in Williams and Winter, *Eur. J. Immunol.,* 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.,* 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128: 119-126 (1993), or in vivo by combinatorial infection, e.g., the loxP system described in Waterhouse et al., *Nucl. Acids Res.,* 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA,* 88: 7978-7982 (1991), or assembled together by PCR and then cloned, e.g. as described in Clackson et al., *Nature,* 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.,* 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique,* 1: 11-15 (1989)) in the method of Hawkins et al., *J. Mol. Biol.,* 226: 889-896 (1992) or in the method of Gram et al., *Proc. Natl. Acad. Sci. USA,* 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities of about $10^{-9}$ M or less.

Screening of the libraries can be accomplished by various techniques known in the art. For example, VEGF-C can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized VEGF-C under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA,* 88: 7978-7982 (1991), or by alkali, e.g. as described in Marks et al., *J. Mol. Biol.,* 222: 581-597 (1991), or by VEGF-C antigen competition, e.g. in a procedure similar to the antigen competition method of Clackson et al., *Nature,* 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins,* 8: 309-314 (1990) and in WO 92/09690, and a low coating density of antigen as described in Marks et al., *Biotechnol.,* 10: 779-783 (1992).

It is possible to select between phage antibodies of different affinities, even with affinities that differ slightly, for VEGF-C. However, random mutation of a selected antibody (e.g. as performed in some affinity maturation techniques) is likely to give rise to many mutants, most binding to antigen, and a few with higher affinity. With limiting VEGF-C, rare high affinity phage could be competed out. To retain all higher affinity mutants, phages can be incubated with excess biotinylated VEGF-C, but with the biotinylated VEGF-C at a concentration of lower molarity than the target molar affinity constant for VEGF-C. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-VEGF-C clones may be selected based on activity. In certain embodiments, the invention provides anti-VEGF-C antibodies that bind to living cells that naturally express VEGF-C. In one embodiment, the invention provides anti-VEGF-C antibodies that block the binding between a VEGF-C ligand and VEGF-C, but do not block the binding between a VEGF-C ligand and a second protein. Fv clones corresponding to such anti-VEGF-C antibodies can be selected by (1) isolating anti-VEGF-C clones from a phage library as described above, and optionally amplifying the isolated population of phage clones by growing up the population in a suitable bacterial host; (2) selecting VEGF-C and a second protein against which blocking and non-blocking activity, respectively, is desired; (3) adsorbing the anti-VEGF-C phage clones to immobilized VEGF-C; (4) using an excess of the second protein to elute any undesired clones that recognize VEGF-C-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.,* 5: 256 (1993) and Pluckthun, *Immunol. Revs,* 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-VEGF-C antibody derived from a hybridoma of the invention can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA,* 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Vectors, Host Cells, and Recombinant Methods

Antibodies may also be produced using recombinant methods. For recombinant production of an anti-VEGF-C antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, Nat. Biotech. 22:1409-1414 (2004).

Certain fungi and yeast strains may be selected in which glycosylation pathways have been "humanized," resulting in the production of an antibody with a partially or fully human glycosylation pattern. See, e.g., Li et al., Nat. Biotech. 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, duckweed (Lemnaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABXTMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

In general, various methodologies for preparing antibodies for use in research, testing, and clinical are well-established in the art, consistent with the above-described methodologies and/or as deemed appropriate by one skilled in the art for a particular antibody of interest.

Pharmaceutical Formulations and Dosages

The antibody composition will be formulated, dosed, and administered in a fashion consistent with good medical practice. Factors for consideration in this context include, but not limited to, the particular disorder being treated, the particular mammal being treated, the clinical condition of the individual patient, the cause of the disorder, the site of delivery of the agent, the method of administration, the scheduling of administration, and other factors known to medical practitioners. For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Pharmaceutical formulations herein may also contain more than one active compound as necessary for the particular indication being treated, preferably those with complementary activities that do not adversely affect each other. Such molecules are suitably present in combination in amounts that are effective for the purpose intended.

The "therapeutically effective amount" of the antibody to be administered will be governed by considerations discussed above, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages. Generally, alleviation or treatment of a disease or disorder involves the lessening of one or more symptoms or medical problems associated with the disease or disorder. In the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. In some embodiments, a composition of this invention can be used to prevent the onset or reoccurrence of the disease or disorder in a subject or mammal.

In certain embodiments, depending on the type and severity of the disease, about 1 µg/kg to 50 mg/kg (e.g., 0.1-20 mg/kg) of antibody is an initial candidate dosage for administration to the patient, whether, for example, by one or more separate administrations, or by continuous infusion. In another embodiment, about 1 µg/kg to 15 mg/kg (e.g. 0.1 mg/kg-10 mg/kg) of antibody is an initial candidate dosage for administration to the patient. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs.

One exemplary dosage of the antibody would be in the range from about 0.05 mg/kg to about 15 mg/kg. Thus, one or more doses of about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 7.5 mg/kg, 8.0 mg/kg, 9.0 mg/kg, 10 mg/kg or 15 mg/kg (or any combination thereof) may be administered to the patient. Such doses may be administered intermittently, e.g. every day, every three days, every week or every two to three weeks (e.g. such that the patient receives from about two to about twenty, or e.g. about six doses of the antibody). In one embodiment, dose of about 10 mg/kg is administered every three days. An initial higher loading dose, followed by one or more lower doses may be administered. In one embodiment, an exemplary dosing regimen comprises administering an initial loading dose of about 4 mg/kg, followed by a weekly maintenance dose of about 2 mg/kg of the antibody. However, other dosage regimens may be useful.

In certain embodiments, dosing regimens discussed herein are used in combination with anti-VEGF antibody and/or a chemotherapy regimen as the first line therapy for treating metastatic colorectal cancer. In some aspects, the chemotherapy regimen involves the traditional high-dose intermittent administration. In some other aspects, the chemotherapeutic agents are administered using smaller and more frequent doses without scheduled breaks ("metronomic chemotherapy").

The progress of the therapy of the invention is easily monitored by conventional techniques and assays.

An antibody of the invention (and any additional therapeutic agent or adjuvant) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target of an antibody is located in the brain, certain embodiments of the invention provide for the antibody to traverse the blood-brain barrier. Several art-known approaches exist for transporting molecules across the blood-brain barrier, including, but not limited to, physical methods, lipid-based methods, stem cell-based methods, and receptor and channel-based methods.

Physical methods of transporting an antibody across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., *Gene Therapy* 9: 398-406 (2002)), interstitial infusion/convection-enhanced delivery (see, e.g., Bobo et al., *Proc. Natl. Acad. Sci. USA* 91: 2076-2080 (1994)), and implanting a delivery device in the brain (see, e.g., Gill et al., *Nature Med.* 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody (see, e.g., U.S. Patent Publication No. 2003/0083299).

Lipid-based methods of transporting an antibody across the blood-brain barrier include, but are not limited to, encapsulating the antibody in liposomes that are coupled to antibody binding fragments that bind to receptors on the vascular endothelium of the blood-brain barrier (see, e.g., U.S. Patent Application Publication No. 20020025313), and coating the antibody in low-density lipoprotein particles (see, e.g., U.S. Patent Application Publication No. 20040204354) or apolipoprotein E (see, e.g., U.S. Patent Application Publication No. 20040131692).

Stem-cell based methods of transporting an antibody across the blood-brain barrier entail genetically engineering neural progenitor cells (NPCs) to express the antibody of interest and then implanting the stem cells into the brain of the individual to be treated. See Behrstock et al. (2005) Gene Ther. 15 Dec. 2005 advanced online publication (reporting that NPCs genetically engineered to express the neurotrophic factor GDNF reduced symptoms of Parkinson disease when implanted into the brains of rodent and primate models).

Receptor and channel-based methods of transporting an antibody across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Pharmaceutical formulations comprising an antibody of the invention are prepared for storage by mixing the antibody having the desired degree of purity with optional physiologically acceptable carriers, excipients or stabilizers (*Remington: The Science and Practice of Pharmacy* 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy* 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Methods

The invention further provides methods, kits and articles of manufacture for modulating (e.g., inhibiting) processes involved in lympthangiogenesis and angiogenesis and for use in targeting pathological conditions associated with lymphangiogenesis and angiogenesis, such as cancer.

Anti-angiogenic therapy in relationship to cancer is a cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics.

Accordingly, the invention encompasses methods for inhibiting angiogenesis using an effective amount of a VEGF-C antagonist (such as an anti-VEGF-C antibody or a VEGF-C immunoadhesin) to inhibit VEGF-C activation of VEGF-C receptors (such as VEGFR3 and VEGFR2). In another aspect, the invention provides methods for inhibiting lymphangiogenesis comprising administering an effective amount of a VEGF-C antagonist to a subject in need of such treatment. In some embodiments, the VEGF-C antagonist is capable of inhibiting LEC endothelial cell migration, proliferation and/or inhibiting LEC sprouting. In another embodiment, the invention provides methods for inhibiting LEC endothelial cell proliferation and/or inhibiting LEC endothelial cell migration comprising administering an effective amount of a VEGF-C antagonist and a VEGF-A antagonist to a subject in need of such treatment. In one embodiment, the VEGF-C antagonist is anti-VEGF-C antibody and the VEGF-A antagonist is anti-VEGF-A antibody. In yet another embodiment, the anti-VEGF-A antibody is bevacizumab.

Therapeutic Methods

An antibody of the invention may be used in, for example, in vitro, ex vivo, and in vivo therapeutic methods.

In one aspect, the invention provides methods for treating or preventing a tumor, a cancer, and/or a cell proliferative disorder (e.g., disorder associated with increased expression and/or activity of VEGF-C) comprising administering an effective amount of an anti-VEGF-C antibody to a subject in need of such treatment.

In one aspect, the invention provides methods for reducing, inhibiting, blocking, or preventing growth of a tumor or cancer, the methods comprising administering an effective amount of an anti-VEGF-C antibody to a subject in need of such treatment.

In one aspect, the invention provides methods for inhibiting angiogenesis comprising administering an effective amount of an anti-VEGF-C antibody to a subject in need of such treatment.

In one aspect, the invention provides methods for treating a pathological condition associated with angiogenesis comprising administering an effective amount of an anti-VEGF-C antibody to a subject in need of such treatment. In some embodiments, the pathological condition associated with angiogenesis is a tumor, a cancer, and/or a cell proliferative disorder.

An antibody of the invention can be administered to a human for therapeutic purposes. In one embodiment, an antibody of the invention is used in a method for binding VEGF-C in an individual suffering from a disorder associated with increased VEGF-C expression and/or activity, the method comprising administering to the individual the antibody such that VEGF-C in the individual is bound. In one embodiment, the VEGF-C is human VEGF-C, and the individual is a human individual. Alternatively, the individual can be a mammal expressing VEGF-C to which an antibody of the invention binds. Still further the individual can be a mammal into which VEGF-C has been introduced (e.g., by administration of VEGF-C or by expression of a transgene encoding VEGF-C).

In one aspect, at least some of the antibodies of the invention can bind VEGF-C from species other than human. Accordingly, the antibodies of the invention can be used to bind specific antigen activity, e.g., in a cell culture containing the antigen, in human subjects or in other mammalian subjects having the antigen with which an antibody of the invention cross-reacts (e.g., chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

Moreover, an antibody of the invention can be administered to a non-human mammal expressing VEGF-C with which the antibody cross-reacts (e.g., a primate, pig, rat, or mouse) for veterinary purposes or as an animal model of human disease. Regarding the latter, such animal models may be useful for evaluating the therapeutic efficacy of antibodies of the invention (e.g., testing of dosages and time courses of administration).

The antibodies of the invention can be used to treat, inhibit, delay progression of, prevent/delay recurrence of, ameliorate, or prevent diseases, disorders or conditions associated with expression and/or activity of one or more antigen molecules.

The present invention also encompasses the prevention and treatment of tumoral lymphangiogenesis, the prevention and treatment of tumor metastasis and anti-angiogenic cancer therapy, a novel cancer treatment strategy aimed at inhibiting the development of tumor blood vessels required for providing nutrients to support tumor growth.

The invention specifically includes inhibiting the neoplastic growth of tumor at the primary site as well as preventing and/or treating metastasis of tumors at the secondary sites, therefore allowing attack of the tumors by other therapeutics. Examples of cancer to be treated (including prevention) herein include, but are not limited to, cancers provided herein under "Definitions," such as carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from the group consisting of small cell lung cancer, glioblastoma, neuroblastomas, melanoma, breast carcinoma, gastric cancer, colorectal cancer (CRC), and hepatocellular carcinoma. Yet, in some embodiments, the cancer is selected from the group consisting of non-small cell lung cancer, colorectal cancer, renal cancer, ovarian cancer, glioblastoma and breast carcinoma, including metastatic forms of those cancers.

The invention further specifically includes preventing and/or treating non-neoplastic conditions. Non-neoplastic conditions that are amenable to treatment with antagonists useful in the invention include, but are not limited to, e.g., undesired or aberrant hypertrophy, arthritis, rheumatoid arthritis (RA), psoriasis, psoriatic plaques, sarcoidosis, atherosclerosis, atherosclerotic plaques, edema from myocardial infarction, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), obesity, adipose tissue mass growth, hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

Further examples of disorders to be treated with a VEGF-C antagonist (such as an anti-VEGF-C antibody) include an epithelial or cardiac disorder.

It is understood that therapeutic methods described herein may be carried out using an immunoconjugate of the invention in place of or in addition to the anti-VEGF-C antibody. In certain embodiments, an immunoconjugate comprising an antibody conjugated with one or more cytotoxic agent(s) is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. In one embodiment, the cytotoxic agent targets or interferes with microtubule polymerization. Examples of such cytotoxic agents include any of the chemotherapeutic agents noted herein (such as a maytansinoid, auristatin, dolastatin, or a calicheamicin), a radioactive isotope, or a ribonuclease or a DNA endonuclease.

Combination Therapies

Antibodies of the invention can be used either alone or in combination with other compositions in a therapy. In certain embodiments, an antibody of the invention may be co-administered with at least one additional therapeutic agent and/or adjuvant For instance, an anti-VEGF-C antibody of the invention may be co-administered with another antibody (e.g., anti-VEGF antibody), chemotherapeutic agent(s) (including cocktails of chemotherapeutic agents), other cytotoxic agent(s), anti-angiogenic agent(s), cytokines, and/or growth inhibitory agent(s).

Where an antibody of the invention inhibits tumor growth, it may be particularly desirable to combine it with one or more other therapeutic agent(s) which also inhibits tumor growth, e.g., anti-angiogenic agents and/or chemotherapeutic agents. Typically, the anti-VEGF-C antibodies and anti-cancer agents are suitable for the same or similar diseases to block or reduce a pathological disorder such as a tumor, a cancer or a cell proliferative disorder. In one embodiment, anti-VEGF-C antibodies may be used in combinations with anti-cancer therapeutics or anti-neovascularization therapeutics to treat various neoplastic or non-neoplastic conditions. Alternatively, or additionally, anti-VEGF-C antibodies may be used in combinations with other inhibitors of VEGF-C. In one embodiment, the neoplastic or non-neoplastic condition is characterized by pathological disorder associated with aberrant or undesired angiogenesis. In another embodiment the anti-cancer agent is an anti-angiogenic agent.

Many anti-angiogenic agents and chemotherapeutic agents have been identified and are known in the arts. An exemplary and non-limiting list of anti-angiogenic agents and chemotherapeutic agents contemplated is provided herein under "Definitions." See also e.g., Carmeliet and Jain, *Nature* 407: 249-257 (2000); Ferrara et al., *Nature Reviews*: Drug Discovery, 3:391-400 (2004); and Sato *Int. J. Clin. Oncol.*, 8:200-206 (2003) and US Patent Publication No. US20030055006.

In certain embodiments, the anti-VEGF-C antibody of the invention is used in combination with an anti-VEGF antibody to generate additive or synergistic effects. In one embodiment, two or more antibodies binding the same or two or more different antigens disclosed herein can be co-administered to the patient. In another embodiment, anti-VEGF antibodies include those that bind to the same epitope as the anti-hVEGF antibody A4.6.1. In yet another embodiment, the anti-VEGF antibody is bevacizumab or ranibizumab. Sometimes, it may be beneficial to also administer one or more cytokines to the patient.

In one embodiment, a VEGF-C antagonist is used in combination with an anti-angiogenic agent such as anti-VEGF neutralizing antibody (or fragment) and/or another VEGF antagonist and/or a VEGF receptor antagonist including, but not limited to, for example, soluble VEGF receptor (e.g., VEGFR-1, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. In one embodiment, anti-angiogenic agent is a VEGF antagonist. In yet another embodiment, VEGF antagonist is an anti-VEGF antibody. In yet another embodiment, anti-VEGF antibody is bevacizumab (AVASTIN®, Genentech, Inc., South San Francisco, Calif.). In another embodiment, anti-VEGF antibody is B20-4.1.1 described in US Patent Publication No. 2009/0142343. In yet another embodiment, anti-angiogenic agent is an anti-NRP1 antibody as described in PCT Publication No. WO2007056470, the entire disclosure of which is expressly incorporated herein by reference. In yet another embodiment, anti-angiogenic agent is an anti-NRP2 antibody as described in PCT Application No. PCT/US2007/069179, the entire disclosure of which is expressly incorporated herein by reference. In yet another embodiment, anti-angiogenic agent is an antibody described in PCT Application No. PCT/US2007/069185, the entire disclosure of which is expressly incorporated herein by reference.

In certain embodiments, the anti-VEGF antibody of the invention can be used in combination with small molecule receptor tyrosine kinase inhibitors (RTKIs) that target one or more tyrosine kinase receptors such as VEGF receptors, FGF receptors, EGF receptors and PDGF receptors. Many therapeutic small molecule RTKIs are known in the art, including, but are not limited to, vatalanib (PTK787), erlotinib (TARCEVA®), OSI-7904, ZD6474 (ZACTIMA®), ZD6126 (ANG453), ZD1839, sunitinib (SUTENT®), semaxanib (SU5416), AMG706, AG013736, Imatinib (GLEEVEC®), MLN-518, CEP-701, PKC-412, Lapatinib (GSK572016), VELCADE®, AZD2171, sorafenib (NEXAVAR®), XL880, and CHIR-265. Other therapeutic agents useful for combination tumor therapy with the antibody of the invention include antagonist of other factors that are involved in tumor growth, such as EGFR, ErbB2 (also known as Her2) ErbB3, ErbB4, or TNF.

In certain embodiments, two or more angiogenesis inhibitors may optionally be co-administered to the patient in addition to VEGF-C antagonist and other agent. In one embodiment, one or more additional therapeutic agents, e.g., anti-cancer agents, can be administered in combination with VEGF-C antagonist, the VEGF antagonist, and an anti-angiogenic agent.

In certain aspects of the invention, other therapeutic agents useful for combination tumor therapy with an anti-VEGF-C antibody include other cancer therapies, e.g., surgery and radiological treatments (e.g. external beam irradiation or therapy with a radioactive labeled agent, such as an antibody. In one embodiment, the patient may receive an antibody of the invention combined with radiation therapy.

The administration of the VEGF-C antagonist and the other therapeutic agent (e.g., anti-cancer agent, anti-angiogenic agent) can be done simultaneously, e.g., as a single composition or as two or more distinct compositions using the same or different administration routes. Alternatively, or additionally, the administration can be done sequentially, in any order. For example, the anti-cancer agent may be administered first, followed by the VEGF-C antagonist. Alternatively, or additionally, the steps can be performed as a combination of both sequentially and simultaneously, in any order. In certain embodiments, intervals ranging from minutes to days, to weeks to months, can be present between the administrations of the two or more compositions.

The effective amounts of therapeutic agents administered in combination with a VEGF-C antagonist will be at the physician's or veterinarian's discretion. Dosage administration and adjustment is done to achieve maximal management of the conditions to be treated. The dose will additionally depend on such factors as the type of therapeutic agent to be used and the specific patient being treated. Suitable dosages for the anti-cancer agent are those presently used and can be lowered due to the combined action (synergy) of the anti-cancer agent and the VEGF-C antagonist. In certain embodiments, the combination of the inhibitors potentiates the efficacy of a single inhibitor. The term "potentiate" refers to an improvement in the efficacy of a therapeutic agent at its common or approved dose. See also the section entitled Pharmaceutical Formulations and Dosages herein.

Chemotherapeutic Agents

In one aspect, the invention provides a method of treating a disorder (such as a tumor, a cancer, or a cell proliferative disorder) by administering effective amounts of an antagonist of VEGF-C and/or an angiogenesis inhibitor(s) and one or more chemotherapeutic agents. A variety of chemotherapeutic agents may be used in the combined treatment methods of the invention. An exemplary and non-limiting list of chemotherapeutic agents contemplated is provided herein under "Definitions." The administration of the VEGF-C antagonist and the chemotherapeutic agent can be done simultaneously, e.g., as a single composition or as two or more distinct compositions, using the same or different administration routes. Alternatively, or additionally, the administration can be done sequentially, in any order. Alternatively, or additionally, the steps can be performed as a combination of both sequentially and simultaneously, in any order. In certain embodiments, intervals ranging from minutes to days, to weeks to months, can be present between the administrations of the two or more compositions. For example, the chemotherapeutic agent may be administered first, followed by the VEGF-C antagonist. However, simultaneous administration or administration of the VEGF-C antagonist first is also contemplated. Accordingly, in one aspect, the invention provides methods comprising administration of a VEGF-C antagonist (such as an anti-VEGF-C antibody), followed by administration of a chemotherapeutic agent. In certain embodiments, intervals ranging from minutes to days, to weeks to months, can be present between the administrations of the two or more compositions.

As will be understood by those of ordinary skill in the art, the appropriate doses of chemotherapeutic agents will be generally around those already employed in clinical therapies wherein the chemotherapeutics are administered alone or in combination with other chemotherapeutics. Variation in dosage will likely occur depending on the condition being treated. The physician administering treatment will be able to determine the appropriate dose for the individual subject.

Relapse Tumor Growth

The invention also provides methods and compositions for inhibiting or preventing relapse tumor growth or relapse cancer cell growth. Relapse tumor growth or relapse cancer cell growth is used to describe a condition in which patients undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the patients or the patients are no longer receiving any beneficial effect from the therapy such that these patients need additional effective therapy. As used herein, the phrase can also refer to a condition of the "non-responsive/refractory" patient, e.g., which describe patients who respond to therapy yet suffer from side effects, develop resistance, do not respond to the therapy, do not respond satisfactorily to the therapy, etc. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells, using the art-accepted meanings of "relapse" or "refractory" or "non-responsive" in such a context. A tumor resistant to anti-VEGF treatment is an example of a relapse tumor growth.

The invention provides methods of blocking or reducing relapse tumor growth or relapse cancer cell growth in a subject by administering one or more VEGF-C antagonist to block or reduce the relapse tumor growth or relapse cancer cell growth in subject. In certain embodiments, the antagonist can be administered subsequent to the cancer therapeutic. In certain embodiments, the VEGF-C antagonists are administered simultaneously with cancer therapy. Alternatively, or additionally, the VEGF-C antagonist therapy alternates with another cancer therapy, which can be performed in any order. The invention also encompasses methods for administering one or more inhibitory antibodies to prevent the onset or recurrence of cancer in patients predisposed to having cancer. Generally, the subject was or is concurrently undergoing cancer therapy. In one embodiment, the cancer therapy is treatment with an anti-angiogenesis agent, e.g., a VEGF antagonist. The anti-angiogenesis agent includes those known in the art and those found under the Definitions herein. In one embodiment, the anti-angiogenesis agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., Journal of Immunological Methods 288:149-164 (2004); and, WO2005012359. Additional agents can be administered in combination with VEGF antagonist and a VEGF-C antagonist for blocking or reducing relapse tumor growth or relapse cancer cell growth, e.g., see section entitled Combination therapies herein.

Diagnostic Methods and Methods of Detection

In one aspect, the invention provides a method of diagnosing a disorder associated with increased expression of VEGF-C. In certain embodiments, the method comprises contacting a test cell with an anti-VEGF-C antibody; determining the level of expression (either quantitatively or qualitatively) of VEGF-C by the test cell by detecting binding of the anti-VEGF-C antibody to VEGF-C; and comparing the level of expression of VEGF-C by the test cell with the level of expression of VEGF-C by a control cell (e.g., a normal cell of the same tissue origin as the test cell or a cell that expresses VEGF-C at levels comparable to such a normal cell), wherein a higher level of expression of VEGF-C by the test cell as compared to the control cell indicates the presence of a disorder associated with increased expression of VEGF-C. In certain embodiments, the test cell is obtained from an individual suspected of having a disorder associated with increased expression of VEGF-C. In certain embodiments, the disorder is a tumor, cancer, and/or cell proliferative disorder.

Exemplary disorders that may be diagnosed using an antibody of the invention include, but not limited to, list of disorders, tumors and cancers provided herein under "Definitions."

In another aspect, the invention provides a method of detecting the presence of VEGF-C in a biological sample. The term "detecting" as used herein encompasses quantitative or qualitative detection.

In certain embodiments, the method comprises contacting the biological sample with an anti-VEGF-C antibody under conditions permissive for binding of the anti-VEGF-C antibody to VEGF, and detecting whether a complex is formed between the anti-VEGF-C antibody and VEGF-C. In some embodiments, the complex is in vivo or in vitro. In some embodiments, the complex comprises a cancer cell.

Analytical methods for VEGF-C all use one or more of the following reagents: labeled VEGF-C analogue, immobilized VEGF-C analogue, labeled anti-VEGF-C antibody, immobilized anti-VEGF-C antibody and/or steric conjugates. The labeled reagents also are known as "tracers."

In certain embodiments, the anti-VEGF-C antibody is detectably labeled. The label used is any detectable functionality that does not interfere with the binding of VEGF-C and anti-VEGF-C antibody. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature, 144: 945 (1962); David et al., Biochemistry, 13: 1014-1021 (1974); Pain et al., J. Immunol. Methods, 40: 219-230 (1981); and Nygren, J. Histochem. and Cytochem., 30: 407-412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

In certain embodiments, antibodies are immobilized on an insoluble matrix. Immobilization may entail separating an anti-VEGF-C antibody from any VEGF-C that remains free in solution. This conventionally is accomplished by either insolubilizing the anti-VEGF-C antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-VEGF-C antibody after formation of a complex between the anti-VEGF-C antibody and VEGF-C, e.g., by immunoprecipitation.

Anti-VEGF-C antibodies can be used for the detection of VEGF-C in any one of a number of well known detection assay methods. For example, a biological sample may be assayed for VEGF-C by obtaining the sample from a desired source, admixing the sample with anti-VEGF-C antibody to allow the antibody to form antibody/VEGF-C complex with any VEGF-C present in the mixture, and detecting any antibody/VEGF-C complex present in the mixture. The biological sample may be prepared for assay by methods known in the art which are suitable for the particular sample. The methods of admixing the sample with antibodies and the methods of detecting antibody/VEGF-C complex are chosen according to the type of assay used.

Assays used to detect binding of anti-VEGF-C antibodies to VEGF-C include, but not limited to, antigen-binding assays that are well known in the art, such as western blots, radioimmunoassays, ELISA (enzyme linked immunosorbent assay), competitive and "sandwich" assays, immunoprecipitation assays, fluorescent immunoassays, protein A immunoassays, immunohistochemistry (IHC) and steric inhibition assays.

In one embodiment, the expression of VEGF-C in a sample may be examined using immunohistochemistry and staining protocols. Immunohistochemical staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. For sample preparation, a tissue or cell sample from a mammal (typically a human patient) may be used.

Examples of samples include, but are not limited to, cancer cells such as colon, breast, prostate, ovary, lung, stomach, pancreas, lymphoma, and leukemia cancer cells. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., VEGF-C) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody. The primary and/or secondary antibody used for immunohistochemistry typically will be labeled with a detectable moiety.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g., the primary antibody is rabbit polyclonal antibody and secondary antibody is goat anti-rabbit antibody).

Specimens thus prepared may be mounted and coverslipped. Slide evaluation is then determined, e.g., using a microscope, and staining intensity criteria, routinely used in the art, may be employed. Staining intensity criteria may be evaluated as follows:

TABLE 2

| Staining Pattern | Score |
| --- | --- |
| No staining is observed in cells. | 0 |
| Faint/barely perceptible staining is detected in more than 10% of the cells. | 1+ |
| Weak to moderate staining is observed in more than 10% of the cells. | 2+ |

TABLE 2-continued

| Staining Pattern | Score |
| --- | --- |
| Moderate to strong staining is observed in more than 10% of the cells. | 3+ |

Typically, a staining pattern score of about 2+ or higher in an IHC assay is diagnostic and/or prognostic. In some embodiments, a staining pattern score of about 1+ or higher is diagnostic and/or prognostic. In other embodiments, a staining pattern score of about 3 of higher is diagnostic and/or prognostic. It is understood that when cells and/or tissue from a tumor or colon adenoma are examined using IHC, staining is generally determined or assessed in tumor cell and/or tissue (as opposed to stromal or surrounding tissue that may be present in the sample).

Other assay methods, known as competitive or sandwich assays, are well established and widely used in the commercial diagnostics industry. In one embodiment, to screen for antibodies which bind to a particular epitope on the antigen of interest, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al. (1995) *J. Biol. Chem.* 270:1388-1394, can be performed to determine whether the antibody binds an epitope of interest. Detailed exemplary methods for mapping an epitope to which an antibody binds are also provided in Morris (1996) "Epitope Mapping Protocols," in *Methods in Molecular Biology* vol. 66 (Humana Press, Totowa, N.J.). Two antibodies are said to bind to the same epitope if each blocks binding of the other by 50% or more.

Competitive assays rely on the ability of a tracer VEGF-C analogue to compete with the test sample VEGF-C for a limited number of anti-VEGF-C antibody antigen-binding sites. The anti-VEGF-C antibody generally is insolubilized before or after the competition and then the tracer and VEGF-C bound to the anti-VEGF-C antibody are separated from the unbound tracer and VEGF-C. This separation is accomplished by decanting (where the binding partner was preinsolubilized) or by centrifuging (where the binding partner was precipitated after the competitive reaction). The amount of test sample VEGF-C is inversely proportional to the amount of bound tracer as measured by the amount of marker substance. Dose-response curves with known amounts of VEGF-C are prepared and compared with the test results to quantitatively determine the amount of VEGF-C present in the test sample. These assays are called ELISA systems when enzymes are used as the detectable markers.

Another species of competitive assay, called a "homogeneous" assay, does not require a phase separation. Here, a conjugate of an enzyme with the VEGF-C is prepared and used such that when anti-VEGF-C antibody binds to the VEGF-C the presence of the anti-VEGF-C antibody modifies the enzyme activity. In this case, the VEGF-C or its immunologically active fragments are conjugated with a bifunctional organic bridge to an enzyme such as peroxidase. Conjugates are selected for use with anti-VEGF-C antibody so that binding of the anti-VEGF-C antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small VEGF-C fragment so that antibody to hapten is substantially unable to bind the conjugate at the same time as anti-VEGF-C antibody. Under this assay procedure the VEGF-C present in the test sample will bind anti-VEGF-C antibody, thereby allowing anti-hapten to bind the conjugate, resulting in a change in the character of the conjugate hapten, e.g., a change in fluorescence when the hapten is a fluorophore.

Sandwich assays particularly are useful for the determination of VEGF-C or anti-VEGF-C antibodies. In sequential sandwich assays an immobilized anti-VEGF-C antibody is used to adsorb test sample VEGF-C, the test sample is removed as by washing, the bound VEGF-C is used to adsorb a second, labeled anti-VEGF-C antibody and bound material is then separated from residual tracer. The amount of bound tracer is directly proportional to test sample VEGF-C. In "simultaneous" sandwich assays the test sample is not separated before adding the labeled anti-VEGF-C. A sequential sandwich assay using an anti-VEGF-C monoclonal antibody as one antibody and a polyclonal anti-VEGF-C antibody as the other is useful in testing samples for VEGF-C.

The foregoing are merely exemplary detection assays for VEGF-C. Other methods now or hereafter developed that use anti-VEGF-C antibody for the determination of VEGF-C are included within the scope hereof.

It is understood that any of the above embodiments of diagnosis or detection may be carried out using an immunoconjugate of the invention in place of or in addition to an anti-VEGF-C antibody.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims. All references cited throughout the specification, and the references cited therein, are hereby expressly incorporated by reference in their entirety. Throughout the present application, including the claims, the term "comprising" is used as an inclusive, open-ended transition phrase, which does not exclude additional, unrecited elements or method steps.

EXAMPLES

Example 1

Generation and Characterization of Anti-VEGF-C Antibodies

Synthetic phage antibody libraries were built on a single framework (humanized anti-ErbB2 antibody, 4D5) by introducing diversity within the complementarity-determining regions (CDRs) of heavy and light chains (Lee, C. V. et al. *J Mol Biol* 340, 1073-93 (2004)). In brief, phage-displayed synthetic antibody libraries were built on a single human framework by introducing synthetic diversity at solvent-exposed positions within the heavy chain complementarity-determining regions (CDRs). To improve library performance, monovalent and bivalent antigen-binding fragment (Fab) libraries were constructed, and explored different CDR-H3 diversities by varying the amino acid composition and CDR length. The library was then expanded by increasing the variability of CDR-H3 length and using tailored codons that mimicked the amino acid composition of natural CDR-H3 sequences. Using these libraries with completely synthetic CDRs displayed on a single scaffold high affinity antibodies were generated. For further details of strategies and methods for generating synthetic antibody libraries with single template, see, e.g., WO 2005/012359 published Feb. 10, 2005, the entire disclosure of which is expressly incorporated herein by reference.

Plate panning with naïve libraries was performed against human VEGF-C matured form (R&D systems) 5 ug/ml immobilized on MaxiSorp™ immunoplates. After four rounds of enrichment, clones were randomly picked and specific binders were identified using phage ELISA. For each positive phage clone, variable regions of heavy and light chains were subcloned into pRK expression vectors that were engineered to express full-length IgG chains. Heavy chain and light chain constructs were co-transfected into 293 or CHO cells, and the expressed antibodies were purified from serum-free medium using protein A affinity column. Purified antibodies were tested by ELISA for blocking the interaction between human VEGF-C and human VEGFR3. For affinity maturation, phage libraries with different combination of CDR loops (CDR-L3 and H3) derived from the initial clone of interest were constructed by soft randomization strategy so that each selected position was mutated to a non-wild type residue or maintained as wild type at about 50:50 frequency (Lee, C. V et al., *Blood,* 108:3103-3111, 2006). High affinity clones were then identified through four rounds of solution phase panning against biotinylated human VEGF-C and then captured by neutravidin coated on the 96-well Maxisorp plate (5 μg/ml). Decreasing biotinylated antigen concentration allowed more stringency in panning.

Example 2

Anti-VEGE-C Antibodies Binding Affinities, Epitope Mapping and Blocking Analysis Phage clones were propagated from a single colony by growing in 30 ml of 2YT culture supplemented with carbenicillin and KO7 helper phage overnight at 30° C., and purified as described (Lee, C V, *J Mol Biol* 340, 2004). Phage were first titrated by diluting in PBS with 0.5% BSA and 0.05% Tween20 (PBT) and tested for binding to hVEGF-C coated plate. The dilution that gave 50%-70% saturation was used to perform the competition binding assay in which phage were first incubated with increasing concentrations of hVEGF-C for 1-2 hour and then transferred to hVEGF-C coated plates to capture the unbound phage. The amount of phage bound was measured with anti-M13 antibody horse-radish peroxidase conjugate (Amersham) and developed with tetramethylbenzidine (TMB) (Kirkegaard and Perry Laboratories, Gaithersburg, Md.) as substrate for ~5 min, quenched with 1.0 M $H_3PO_4$ and read spectrophotometrically at 450 nm wavelength. $IC_{50}$ values were calculated as the concentration of soluble antigen that inhibited 50% of the phage from binding to immobilized antigen. See also FIGS. 33, 35 and 36.

To determine binding affinities of anti-VEGF-C IgGs, surface plasmon resonance (SRP) measurement with a BIAcore™-3000 instrument was used. First of all, anti-VEGF-C human IgGs were captured by CM5 biosensor chips to achieve approximately 500 response units (RU). For kinetics measurements, two-fold serial dilutions of human VEGF-C (12.5 nM to 500 nM) were injected separately in PBT buffer (PBS with 0.05% (v/v) Tween 20) at 25° C. with a flow rate of 300 min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$. See also FIGS. 31 and 34.

To evaluate the receptor blocking activities of anti-VEGF-C IgG, three-fold serial dilutions of anti-VEGF-C IgGs were first incubated with optimized biotinylated VEGF-C concentration in PBST buffer for 2 hour, following by captured on VEGFR3 coated Maxisorp plate for 15 minutes. The amount of biotinylated VEGF-C binding to VEGFR3 was detected by streptavidin-HRP conjugates. See also FIGS. 10 and 32.

To map the epitope of anti-VEGF-C antibodies, three-fold serial dilutions of VC4.5 IgG were first incubated with 96-well Maxisorp plate coated hVEGF-C C137S (5 µg/ml) in PBST buffer for 2 hr, following by adding anti-VEGF-C phage with concentration of optimized OD 450 nm signal for 15 minutes. The amount of anti-VEGF-C phage binding to hVEGF-C C137S was detected by anti-M13 HRP conjugates. See also FIG. 37.

Example 3

Cell Cultures

HMVEC-dLyAd—Human Dermal Lymphatic Microvascular Endothelial Cells (LECs) and HUVECS were purchased from Cambrex and cultured in EGM-2 medium (Cambrex). C6 LacZ cells were purchased from ATCC. Tumor cells were cultured in DMEM (Gibco) supplemented with 10% FBS. All cells were maintained at 37° C. in a 5% $CO_2$, 95% humidity incubator.
Cell Migration Assay VEGF-C has been shown to potently induce migration and proliferation of endothelial cells of lymphatic (LEC's) and venous (HUVEC) origin likely, by binding to and activating VEGFR2 and VEGFR3.

Migration assays were performed using a modified Boyden chamber with 8 µM pore size Falcon 24-multiwell insert system (BD Biosciences). The plates were coated with 5µ/ml Fibronectin (Invitrogen) for 2 hours at 37° C. Cells in 100 µl assay medium (0.1% BSA, EGM-2) with/without antibodies were added to the upper chamber. Chemoattractant was added to the lower chamber in 500 µl assay medium, and cells were incubated at 37° C. for 16 hours. Cells on the upper membrane were removed with a sponge swa.b and cells on the lower surface were fixed in 70% ethanol and stained with Sytox green (Molecular Probes). Images were taken of the entire lower surface of the well, and number of migrated cells counted (6 wells per condition). See also FIGS. 7 and 40. Anti-VEGF-C antibody strongly blocked both mature VEGF-C and FL VEGF-C induced migration. The anti-VEGF-C antibody did not have any effect on VEGF or HGF induced migration of HUVECs, confirming its specificity.
Cell Proliferation Assays A 96-well black-clear bottom plate (VWR) was coated with 5 ug/ml Fibronectin (Invitrogen) at 37° C. for 2 hours. LEC's were harvested and resuspended in assay medium (0.1% BSA, EGM-2) 3000 cells/100 ul and added to wells. Cells were incubated at 37° C. for 16 hours. BrdU labeling solution (Cell Proliferation ELISA kit; Roche) was added and the cells were incubated for a further 24 hours at 37° C. BrdU incorporation was determined by chemiluminescence immunoassay (6 wells per condition). See also FIGS. 8, 12 and 45. Anti-VEGF-C antibody strongly blocked both mature VEGF-C and full-length VEGF-C induced proliferation. The anti-VEGF-C antibody did not have any effect on VEGF or HGF induced proliferation of HUVECs, confirming its specificity.
Sprouting Assays Dextran-coated Cytodex 3 microcarrier beads (Amersham) were incubated with LECs (400 cells per bead) in EGM-2, which contains 200 ng/ml VEGF-C, for 4 hours at 37° C., inverting every 20 minutes. Beads were then plated overnight at 37° C. to separate cells not coated on beads. To induce clotting, 0.5 ml cell-coated beads in EGM-2 with 2.5 mg/ml fibrinogen (200 beads/ml)+/−VEGF-C and antibodies was added into one well of a 24-well tissue culture plate containing 0.625 units thrombin and incubated for 5 min at room temperature and then for 20 min at 37° C. The clot was equilibrated in EGM-2 for 30 min at 37° C. The medium was then replaced with EGM-2 containing skin fibroblast cells (Detroit 551, 20,000 cells/ml). VEGF-C+/−antibodies were added to each well, and the assay was monitored for 14 days with change in medium every 2-3 days. 10 images of the beads were captured per condition by an inverted microscope. See also FIG. 9.
Mouse Corneal Micro Pocket Assay Adult CD-1 mice (Charles-River) were anesthetized and a pocket of 2×3 mm were created 1 mm from the center of the cornea in the epithelium by micro-dissection as described previously (Polyerini et al., *Methods Enzymol* 198:440-450 (1991)). Agents to be tested for lymphangiogenic activity were immobilized in an inert hydron pellet (2×2 mm). The pellet was then implanted into the base of the pocket. Animals were treated with control antibody (10 mg/kg) or anti-VEGF-C (10 mg/kg) i.p. twice weekly for 2 weeks. Then animals were perfused with FITC-labeled Isolectin B4 (Sigma) to identify blood vessels and then perfused with 4% PFA via left ventricular cardiac puncture, sacrificed and corneas dissected. The lymphatics were visualized by whole-mount IHC with anti-LYVE-1 antibody (R&D Systems 1:500). The corneas were photographed and blood vessels (FITC label) and LYVE-1 positive lymphatic vessels arising from the limbus were quantified. See also FIGS. 13 and 14. Angiogenesis and lymphangiogenesis in this model are completely blocked by the systemic administration of anti-VEGF-C antibody, but is unaffected by anti-VEGF antibody.

VEGF Receptor Signaling Assays

Confluent HUVECs were stimulated for 10 minutes with 200 ng/ml of VEGF-C in the presence or absence of control or anti-VEGF-C antibodies. The cells were lysed and assayed for many mediators know to play a role if VEGF receptor signaling. VEGFR2 activation was evaluated using total VEGFR2 and phospho-VEGFR2 ELISA assays (DuoSet IC ELISA kit, R&D). See also FIG. 11. VEGFR3 activation was evaluated using a kinase receptor activation assay (KIRA) with an VEGFR3-293 cell line as previously described (Sadick et al., 1999). See also FIG. 41. Briefly, stable 293 cell lines expressing full length Flag tagged human hVEGFR3 were assayed for receptor phosphorylation following stimulation. $5 \times 10^4$ cells were starved overnight (DMEM with 0.1% BSA) and then stimulated with 40 ng/ml VEGF-A (Genentech South San Francisco, Calif.) or 200 ng/ml VEGF-C (Genentech Inc., South San Francisco, Calif.) for 8 minutes. Cells were lysed in PBS containing 1% triton and sodium orthovanadate. ELISA plates were coated with capture Flag antibody (Sigma St Louis, Mo.). The plates were coated (PBS+1 ug/ml of antibody) overnight and blocked (PBS+0.5% BSA) for 1 hr. After 3 washes (PBS+0.05% Tween 20), lysates were added for 2 hours, washed three times, followed by addition of phospho-detection antibody 4G10 (Upstate Lake Placed, N.Y.) for 2 hours. Detection was performed with HRP antibody (Amersham Piscataway, N.J.) and TMB substrate. Plates were read at 450 nm. Anti-VEGF-C completely inhibited VEGF-C mediated phosphorylation of VEGFR2 and VEGFR3.

Mouse Skin Vessel Permeability Assay

The backs and flanks of adult C57BL6J female mice were shaved and divided into 4 treatment areas. They were then injected i.v. with 150 µl 0.5% Evan's blue solution. 1 hr after the Evan's blue injection, 20 µA of PBS containing BSA or VEGF-C (7.5 µg/ml) with or without anti-VEGF-C antibody or VEGFR3 ECD (0.5 mg/ml) was injected intradermally, randomly on one of the four zones. 1 hr later, the animals were sacrificed and the skin was dissected out and imaged. Skin samples for each injection zone were cut out and incubated in formamide solution at 55° C. for 48 hrs to extract the blue dye. The absorbance of the solution was then measured with a spectrometer at 600 nm. Quantification of the Evan's blue dye extracted from skin samples in the permeability assay is shown in FIG. 42. Treatment with anti-VEGF-C antibody and VEGFR3 ECD reduced VEGF-C induced vascular permeability. VEGF induced vascular permeability was not blocked by anti-VEGF-C, confirming specificity.

Animal Studies

All studies were conducted in accordance with the Guide for the Care and Use of Laboratory Animals, published by the NIH (NIH Publication 85-23, revised 1985). An Institutional Animal Care and Use Committee (IACUC) approved all animal protocols.

Tumor Models

It has previously been reported that VEGF-C plays a role in primary tumor growth and dissemination of tumor cells by inducing angiogenesis and lymphangiogenesis (Alitalo and Carmeliet, *Cancer Cell* 1, 219-227 (2002); Cao et al., PNAS 95, 14389-14394 (1998); Skobe et al., *Nature Medicine* 7, 192-198 (2001b); Su et al., *Cancer Cell* 9, 209-223 (2006)). Since anti-VEGF-C antibody described herein blocked angiogenesis and lymphangiogenesis in the corneal micro pocket assay, we evaluated its ability to modulate primary tumor growth in 66c14, and H460 tumor models where anti-VEGF has been shown to have an incomplete anti-angiogenic activity.

For 66C14, cells were harvested by trypsinization, washed, and resuspended in PBS at a concentration of $2 \times 10^5$ cells in 10 µl PBS. Mice were anesthetized using 75 mg/kg ketamine and 7.5 mg/kg xylazine, and an incision made underneath the right forelimb. $2 \times 10^5$ cells in 10 µl PBS was injected directly into the exposed $4^{th}$ mammary fat pad of 6-8 week old female balb-C mice. For C6, $2 \times 10^6$ tumor cells in 100 µl PBS were injected subcutaneously into the right flank of 6-8 week old female balb-C nude mice. For both sets of studies, tumor growth was monitored 3 times weekly. When tumors reach an average size of 80-120 mm³, mice were sorted to give nearly identical group mean tumor sizes, and treatment was started. This was considered day 1 of each study. Animals were treated with control antibody (10 mg/kg) or anti-VEGF-C (10 mg/kg) i.p. twice weekly till study termination. All studies were repeated 3 times to ensure reproduceability. See also FIGS. 15-16, 19-20 and 44.

H460 and A549 tumor model studies were conducted at Piedmont Research Center, LLC (Morrisville, N.C.) using standardized techniques. Briefly, xenografts were initiated from cultured H460 human non-small cell lung carcinoma cells (grown to mid-log phase in RPMI-1640 medium containing 10% heat-inactivated fetal bovine serum, 100 units/mL penicillin G, 100 µg/mL streptomycin sulfate, 0.25 µg/mL amphotericin B, 1 mM sodium pyruvate, 2 mM glutamine, 10 mM HEPES, 0.075% sodium bicarbonate, and 25 µg/mL gentamicin) or from A549 human lung adenocarcinoma cells (cultured in Kaighn's modified Ham's F12 medium containing 10% heat-inactivated fetal bovine serum, 100 units/mL penicillin G, 100 µg/mL streptomycin sulfate, 0.25 µg/mL amphotericin B, 2 mM glutamine, 1 mM sodium pyruvate, and 25 µg/mL gentamicin). On the day of tumor implant, H460 cells were harvested and resuspended in PBS at a concentration of $5 \times 10^7$ cells/mL. Each test mouse received $1 \times 10^7$ H460 tumor cells implanted subcutaneously in the right flank. For A549 tumors, A549 cells were resuspended in 100% Matrigel™ matrix (BD Biosciences) at a concentration of $5 \times 10^7$ cells/mL. A549 cells ($1 \times 10^7$ in 0.2 mL) were implanted subcutaneously in the right flank of each test mouse, and tumor growth was monitored. The animals were sorted by tumor size into four groups (n=10) with group mean tumor volumes of 111-112 mm³ and individual tumor sizes ranging from 75 to 196 mm³ and this was considered day 1 of study. Tumor volume was calculated using the formula: Tumor Volume $(mm^3) = ((w^{2*l})/2)$ where w=width and l=length in mm of a H460 tumor.

All treatments were administered intraperitoneally twice weekly for five weeks (i.p. 2×/wk×5), with anti-VEGF antibody B20-4.1 dosed at 5 mg/kg, and anti-VEGF-C antibody dosed at 10 mg/kg. Group 1 mice received PBS and served as the tumor growth control group. Groups 2 and 3 received monotherapy with anti-VEGF B20-4.1 and anti-VEGF-C antibodies, respectively. Group 4 received anti-VEGF antibody B20-4.1 administered in combination with anti-VEGF-C antibody. For the combination treatment group, anti-VEGF-C antibody was administered no later than thirty minutes after anti-VEGF antibody B20-4.1 dosing. Each dose was delivered in a volume of 0.2 mL per 20 grams body weight (10 mL/kg), and was scaled to the body weight of the animal.

Calculations were performed as follows: percent tumor growth inhibition (% TGI)=(median tumor volume of the control arm−median tumor volume of the treatment arm/median tumor volume of the control arm)×100. % TGI is only measured as long as all animals remain on the study. Time to endpoint (TTE)=$\log_{10}$ (endpoint volume, mm³)−b/m; were b is the intercept and m is the slope of the line obtained by linear regression of the log-transformed tumor growth data. Percent tumor growth delay (% TGD)=(median TTE for a treatment arm−median TTE for the control arm/median TTE for the control arm)×100. See also FIGS. 17 and 18.

At study end animals were anethetiszed and perfused with 4% PFA. Tumors were harvested, cryoprotected and frozen in OCT (Tissue-Tek). Lungs were inflated via a right ventricular perfusion of 10 ml of PBS followed by 4% PFA, and visual counts of metastatic lesions were performed prior to Micro-CT analysis.

In the 66c14 model, anti-VEGF-C antibody significantly reduced primary tumor growth. See FIGS. 16 and 44. This response translated into an increased survival benefit with anti-VEGF-C treatment. Additionally, anti-VEGF-C antibody also showed efficacy in the H460 model.

The ability of both anti-VEGF antibody and anti-VEGF-C antibody to inhibit tumor growth when utilized as single agents suggested that both VEGF and VEGF-C play important roles in promoting angiogenesis. In the 66c14 model, combination treatment of anti-VEGF-C antibody with anti-VEGF antibody showed an almost complete reduction in primary tumor growth compared to either single agent alone. See FIG. 16. This also resulted in an increased survival benefit. This effect was also seen in the H460 tumor model where combination treatment was more effective at inhibiting primary tumor growth than either treatment alone. See FIG. 17. Primary tumor growth inhibition was reduced significantly in the combination arm over the anti-VEGF antibody treatment arm.

Furthermore, our data suggest that concomitant inhibition of VEGF-C and VEGF provides additional benefit for primary tumor growth stasis. See FIG. 43.

Anti-VEGF-C antibody treatment resulted in a reduction of median tumor growth and increase in survival in A549 tumors in combination with anti-VEGF-A antibody. However, anti-VEGF-C antibody treatment did not result in a reduction of tumor growth as a single agent in this model. We reasoned that this is due to the high VEGF protein levels found in this model, which could mask the effect of blocking VEGF-C. Furthermore, we hypothesized that VEGF-C would become biologically significant in the setting of VEGF inhibition, when the levels of VEGF-C may, to some degree, functionally compensate for the blocked VEGF. To test this we evaluated combination treatment in the A549 model and found that this treatment resulted in a significant decrease in primary tumor growth in the combination arm over the anti-VEGF antibody treatment arm (TGI of 62% compared to anti-VEGF; p=0.007). This improvement is also observed in survival, as shown by the Kaplan-Meier plot with TGD increasing from 65% in the anti-VEGF treated arm to 263% in the combination treated arm. Representative images of H&E stained sections in A549 tumors treated with combination of anti-VEGF-A and anti-VEGF-C further show that anti-VEGF-C antibody and anti-VEGF-A antibody combination treatment results in dramatic histologic changes in the primary tumor mass.

Micro-CT Analysis of Lungs

Lungs were immersed in 10% NBF for 24 hours, then immersed in a 20% solution of an iodine-based x-ray computed tomography contrast agent, Isovue370 (Bracco Diagnostics Inc, Princeton, N.J.), for 24 hours. Lungs were then immersed in and perfused via the trachea cannula with 20 mls of soy bean oil (Sigma-Aldrich, St. Louis, Mo.) at a rate of 0.25 ml/min. The soy bean oil was used to remove excess contrast agent and provide a background media for imaging.

The mouse lungs were imaged ex-vivo with a VivaCT (SCANCO Medical, Basserdorf, Switzerland) x-ray micro-computed tomography (micro-CT) system. A sagittal scout image, comparable with a conventional planar x-ray, was obtained to define the start and end point for the axial acquisition of a series of micro-CT image slices. The location and number of axial images were chosen to provide complete coverage of the lung. The lungs were immersed in soybean oil as the background media. The micro-CT images were generated by operating the x-ray tube at an energy level of 45 kV, a current of 160 µA and an integration time of 450 milliseconds. Axial images were obtained at an isotropic resolution of 21 µm. The lung tumor estimates (number and volume) were obtained by a semi-automated image analysis algorithm that includes an inspection step by a trained reader. Lung tumors appear as a hyper-intense solid mass relative to porous, mesh-like structures of the normal lung. This is due to the absorption of the iodine contrast agent by solid structures (bronchial and aveloi walls, tumors, trachea, medial steinum) contained within the lung. Excess contrast agent was cleared from the filled air spaces by the oil perfusion step. Potential tumor masses were extracted by a series of image processing steps. The image analysis software was developed in-house. It was written in C++ and employed the Analyze (AnalyzeDirect Inc., Lenexa, Kans., USA) image analysis software function libraries. The algorithm employs intensity thresholding, morphological filtering and region-growing to extract all potential tumors masses. An intensity threshold (1480 Hounsfield Units) was determined by histogram analysis of 5 arbitrary lungs employed for algorithm development and the optimal threshold was chosen to include tumor voxels and exclude any background signal. Morphological (erosion, dilation) and region-growing operations were applied to connect hyper-intense regions of voxels and to remove any voxels of similar density found in the thin walls of the bronchioles and aveoli. The region growing step requires a minimum volume of 2300 connected voxels (greater than $0.0231 \text{ mm}^3$) to be accepted as an object (mass). The identified objects were then evaluated by a trained reader with the Analyze 3D visualization software. Individual objects were accepted or rejected as possible tumors based on the appearance of the object and its location within the lung. Objects were rejected if they reside outside the lung (ex. mediasteinum, extraneous tissue debris) or resemble a blood-filled vessel. The tumor count, individual tumor volume and total tumor volume were determined for each lung. See also FIGS. 20, 21 and 46.

Immunohistochemistry

18 µm tissue cryosections were cut and mounted onto glass slides. The sections were incubated 0/N with primary antibody (anti-LYVE-1 (anti-R&D, 1:200), anti-PECAM-1 (Benton Dickinson, 1:500), MECA32 (Abcam, 1:1000), or Ki67 (Neovision 1:100) at 4° C. Samples were then stained with Alexa 488 or Alexa 568 secondary antibodies (1:200; Molecular Probes) for 4 hrs at RT. Staining with secondary only was used as a control. TUNNEL staining was performed with a commercial kit (Roche). Images were captured with a Zeiss Axiophot fluorescence microscope. Blood and lymphatic vessel area was determined from 6 representative images from each of 6-10 tumors per group, evaluated for mean pixel number by ImageJ Software (http://rsb.info.nih.gov/ij, last visited Jul. 12, 2007) as previously described (Mancuso et al., *J Clin Invest* (2006); 116(10):2585-7. See also FIG. 21.

What is claimed:

1. A method of inhibiting tumor angiogenesis comprising administering to a subject with cancer an effective amount of an isolated anti-vascular endothelial growth factor-C (VEGF-C) antibody, wherein the antibody comprises six HVRs:
   (1) an HVR-H1 comprising the amino acid sequence of SEQ ID NO:3;
   (2) an HVR-H2 comprising the amino acid sequence of SEQ ID NO:8;
   (3) an HVR-H3 comprising the amino acid sequence of SEQ ID NO:26;
   (4) an HVR-L1 comprising the amino acid sequence of SEQ ID NO:27;
   (5) an HVR-L2 comprising the amino acid sequence of SEQ ID NO:28; and
   (6) an HVR-L3 comprising the amino acid sequence of SEQ ID NO:29.

2. The method of claim 1, wherein the antibody comprises a heavy chain variable domain comprising the amino acid sequence of SEQ ID NO:84 and a light chain variable domain comprising the amino acid sequence of SEQ ID NO:85.

3. The method of claim 1, wherein the antibody further comprises an amino acid substitution at position 297 to alanine.

4. The method of claim 3, wherein the antibody further comprises an amino acid substitution at position 265 to alanine.

5. The method of claim 1, wherein the antibody is a monoclonal antibody.

6. The method of claim 5, wherein the antibody is a humanized antibody.

7. The method of claim 1, wherein the antibody is a bispecific antibody.

8. The method of claim 1, wherein said cancer is a lung cancer, a small-cell lung cancer, a non-small cell lung cancer, an adenocarcinoma of the lung, or a squamous carcinoma of the lung.

9. A method of inhibiting lymphatic endothelial cell migration or cell proliferation comprising administering to a subject with cancer an effective amount of an isolated anti-vascular endothelial growth factor-C (VEGF-C) antibody, wherein the antibody comprises six HVRs:
 (1) an HVR-H1 comprising the amino acid sequence of SEQ ID NO:3;
 (2) an HVR-H2 comprising the amino acid sequence of SEQ ID NO:8;
 (3) an HVR-H3 comprising the amino acid sequence of SEQ ID NO:26;
 (4) an HVR-L1 comprising the amino acid sequence of SEQ ID NO:27;
 (5) an HVR-L2 comprising the amino acid sequence of SEQ ID NO:28; and
 (6) an HVR-L3 comprising the amino acid sequence of SEQ ID NO:29.

10. The method of claim 9, wherein the antibody comprises a heavy chain variable domain comprising the amino acid sequence of SEQ ID NO:84 and a light chain variable domain comprising the amino acid sequence of SEQ ID NO:85.

11. The method of claim 9, wherein the antibody further comprises an amino acid substitution at position 297 to alanine.

12. The method of claim 9, wherein the antibody further comprises an amino acid substitution at position 265 to alanine.

13. The method of claim 9, wherein the antibody is a monoclonal antibody.

14. The method of claim 13, wherein the antibody is a humanized antibody.

15. The method of claim 9, wherein the antibody is a bispecific antibody.

16. The method of claim 9, wherein said cancer is a lung cancer, a small-cell lung cancer, a non-small cell lung cancer, an adenocarcinoma of the lung, or a squamous carcinoma of the lung.

17. A method of inhibiting vascular permeability comprising administering to a subject with cancer an effective amount of an isolated anti-vascular endothelial growth factor-C (VEGF-C) antibody, wherein the antibody comprises six HVRs:
 (1) an HVR-H1 comprising the amino acid sequence of SEQ ID NO:3;
 (2) an HVR-H2 comprising the amino acid sequence of SEQ ID NO:8;
 (3) an HVR-H3 comprising the amino acid sequence of SEQ ID NO:26;
 (4) an HVR-L1 comprising the amino acid sequence of SEQ ID NO:27;
 (5) an HVR-L2 comprising the amino acid sequence of SEQ ID NO:28; and
 (6) an HVR-L3 comprising the amino acid sequence of SEQ ID NO:29.

18. The method of claim 17, wherein the antibody comprises a heavy chain variable domain comprising the amino acid sequence of SEQ ID NO:84 and a light chain variable domain comprising the amino acid sequence of SEQ ID NO:85.

19. The method of claim 17, wherein the antibody further comprises an amino acid substitution at position 297 to alanine.

20. The method of claim 19, wherein the antibody further comprises an amino acid substitution at position 265 to alanine.

21. The method of claim 17, wherein the antibody is a monoclonal antibody.

22. The method of claim 21, wherein the antibody is a humanized antibody.

23. The method of claim 17, wherein the antibody is a bispecific antibody.

24. The method of claim 17, wherein said cancer is a lung cancer, a small-cell lung cancer, a non-small cell lung cancer, an adenocarcinoma of the lung, or a squamous carcinoma of the lung.

25. A method of inhibiting tumoral lymphangiogenesis comprising administering to a subject with cancer an effective amount of an isolated anti-vascular endothelial growth factor-C (VEGF-C) antibody, wherein the antibody comprises six HVRs:
 (1) an HVR-H1 comprising the amino acid sequence of SEQ ID NO:3;
 (2) an HVR-H2 comprising the amino acid sequence of SEQ ID NO:8;
 (3) an HVR-H3 comprising the amino acid sequence of SEQ ID NO:26;
 (4) an HVR-L1 comprising the amino acid sequence of SEQ ID NO:27;
 (5) an HVR-L2 comprising the amino acid sequence of SEQ ID NO:28; and
 (6) an HVR-L3 comprising the amino acid sequence of SEQ ID NO:29.

26. The method of claim 25, wherein the antibody comprises a heavy chain variable domain comprising the amino acid sequence of SEQ ID NO:84 and a light chain variable domain comprising the amino acid sequence of SEQ ID NO:85.

27. The method of claim 25, wherein the antibody further comprises an amino acid substitution at position 297 to alanine.

28. The method of claim 27, wherein the antibody further comprises an amino acid substitution at position 265 to alanine.

29. The method of claim 25, wherein the antibody is a monoclonal antibody.

30. The method of claim 29, wherein the antibody is a humanized antibody.

31. The method of claim 25, wherein the antibody is a bispecific antibody.

32. The method of claim 25, wherein said cancer is a lung cancer, a small-cell lung cancer, a non-small cell lung cancer, an adenocarcinoma of the lung, or a squamous carcinoma of the lung.

33. A method of inhibiting tumor metastasis comprising administering to a subject with cancer an effective amount of an isolated anti-vascular endothelial growth factor-C (VEGF-C) antibody, wherein the antibody comprises six HVRs:
 (1) an HVR-H1 comprising the amino acid sequence of SEQ ID NO:3;
 (2) an HVR-H2 comprising the amino acid sequence of SEQ ID NO:8;
 (3) an HVR-H3 comprising the amino acid sequence of SEQ ID NO:26;
 (4) an HVR-L1 comprising the amino acid sequence of SEQ ID NO:27;
 (5) an HVR-L2 comprising the amino acid sequence of SEQ ID NO:28; and
 (6) an HVR-L3 comprising the amino acid sequence of SEQ ID NO:29.

34. The method of claim 33, wherein the antibody comprises a heavy chain variable domain comprising the amino acid sequence of SEQ ID NO:84 and a light chain variable domain comprising the amino acid sequence of SEQ ID NO:85.

35. The method of claim 33, wherein the antibody further comprises an amino acid substitution at position 297 to alanine.

36. The method of claim 35, wherein the antibody further comprises an amino acid substitution at position 265 to alanine.

37. The method of claim 33, wherein the antibody is a monoclonal antibody.

38. The method of claim 37, wherein the antibody is a humanized antibody.

39. The method of claim 33, wherein the antibody is a bispecific antibody.

40. The method of claim 33, wherein said cancer is a lung cancer, a small-cell lung cancer, a non-small cell lung cancer, an adenocarcinoma of the lung, or a squamous carcinoma of the lung.

* * * * *

SEQUENCE LISTING

<160> NUMBER OF SEQ ID NOS: 91

<210> SEQ ID NO 1
<211> LENGTH: 10
<212> TYPE: PRT
<213> ORGANISM: Artificial sequence
<220> FEATURE:
<223> OTHER INFORMATION: sequence is synthesized

<400> SEQUENCE: 1

Gly Phe Thr Phe Ser Asp Ser Asp Ile His
1               5                   10

<210> SEQ ID NO 2
<211> LENGTH: 10
<212> TYPE: PRT
<213> ORGANISM: Artificial sequence
<220> FEATURE:
<223> OTHER INFORMATION: sequence is synthesized

<400> SEQUENCE: 2

Gly Phe Thr Phe Thr Asn Thr Asp Ile His
1               5                   10

<210> SEQ ID NO 3
<211> LENGTH: 10
<212> TYPE: PRT
<213> ORGANISM: Artificial sequence
<220> FEATURE:
<223> OTHER INFORMATION: sequence is synthesized

<400> SEQUENCE: 3

Gly Phe Thr Phe Thr Asp Asn Trp Ile His
1               5                   10

<210> SEQ ID NO 4
<211> LENGTH: 10
<212> TYPE: PRT
<213> ORGANISM: Artificial sequence
<220> FEATURE:
<223> OTHER INFORMATION: sequence is synthesized

<400> SEQUENCE: 4

Gly Phe Thr Phe Thr Tyr Ser Trp Ile His
1               5                   10

<210> SEQ ID NO 5
<211> LENGTH: 18
<212> TYPE: PRT
<213> ORGANISM: Artificial sequence
<220> FEATURE:
<223> OTHER INFORMATION: sequence is synthesized

<400> SEQUENCE: 5

Ala Trp Ile Ser Pro Tyr Ser Gly Tyr Thr Asp Tyr Ala Asp Ser
1               5                   10                  15

Val Lys Gly

<210> SEQ ID NO 6
<211> LENGTH: 18
<212> TYPE: PRT
<213> ORGANISM: Artificial sequence
<220> FEATURE:
<223> OTHER INFORMATION: sequence is synthesized -continued

```
<400> SEQUENCE: 6

Ala Trp Ile Ser Pro Tyr Val Gly Phe Thr Asp Tyr Ala Asp Ser
1               5                   10                  15

Val Lys Gly

<210> SEQ ID NO 7
<211> LENGTH: 18
<212> TYPE: PRT
<213> ORGANISM: Artificial sequence
<220> FEATURE:
<223> OTHER INFORMATION: sequence is synthesized

<400> SEQUENCE: 7

Ala Trp Ile Ser Pro Ser Ser Gly Tyr Thr Asp Tyr Ala Asp Ser
1               5                   10                  15

Val Lys Gly

<210> SEQ ID NO 8
<211> LENGTH: 18
<212> TYPE: PRT
<213> ORGANISM: Artificial sequence
<220> FEATURE:
<223> OTHER INFORMATION: sequence is synthesized

<400> SEQUENCE: 8

Gly Val Ile Ser Pro Tyr Ser Gly Ala Thr Tyr Tyr Ala Asp Ser
1               5                   10                  15

Val Lys Gly

<210> SEQ ID NO 9
<211> LENGTH: 10
<212> TYPE: PRT
<213> ORGANISM: Artificial sequence
<220> FEATURE:
<223> OTHER INFORMATION: sequence is synthesized

<400> SEQUENCE: 9

Ala Arg Leu Phe Glu Val Ile Phe Asp Tyr
1               5                   10

<210> SEQ ID NO 10
<211> LENGTH: 10
<212> TYPE: PRT
<213> ORGANISM: Artificial sequence
<220> FEATURE:
<223> OTHER INFORMATION: sequence is synthesized

<400> SEQUENCE: 10

Ala Arg Leu Phe Lys Val Ile Phe Asp Tyr
1               5                   10

<210> SEQ ID NO 11
<211> LENGTH: 10
<212> TYPE: PRT
<213> ORGANISM: Artificial sequence
<220> FEATURE:
<223> OTHER INFORMATION: sequence is synthesized

<400> SEQUENCE: 11

Ala Arg Leu Phe Glu Ile Ile Phe Asp Tyr
1               5                   10

<210> SEQ ID NO 12
<211> LENGTH: 10
```

```
<212> TYPE: PRT
<213> ORGANISM: Artificial sequence
<220> FEATURE:
<223> OTHER INFORMATION: sequence is synthesized

<400> SEQUENCE: 12

Val Arg Leu Phe Glu Val Ile Phe Asp Tyr
1               5                   10

<210> SEQ ID NO 13
<211> LENGTH: 10
<212> TYPE: PRT
<213> ORGANISM: Artificial sequence
<220> FEATURE:
<223> OTHER INFORMATION: sequence is synthesized

<400> SEQUENCE: 13

Val Arg Leu Phe Gly Val Ile Phe Asp Tyr
1               5                   10

<210> SEQ ID NO 14
<211> LENGTH: 10
<212> TYPE: PRT
<213> ORGANISM: Artificial sequence
<220> FEATURE:
<223> OTHER INFORMATION: sequence is synthesized

<400> SEQUENCE: 14

Ala Arg Leu Trp Glu Val Ile Phe Asp Tyr
1               5                   10

<210> SEQ ID NO 15
<211> LENGTH: 10
<212> TYPE: PRT
<213> ORGANISM: Artificial sequence
<220> FEATURE:
<223> OTHER INFORMATION: sequence is synthesized

<400> SEQUENCE: 15

Val Arg Leu Phe Asp Val Ile Phe Asp Tyr
1               5                   10

<210> SEQ ID NO 16
<211> LENGTH: 10
<212> TYPE: PRT
<213> ORGANISM: Artificial sequence
<220> FEATURE:
<223> OTHER INFORMATION: sequence is synthesized

<400> SEQUENCE: 16

Ala Arg Leu Phe Asp Ile Ile Phe Asp Tyr
1               5                   10

<210> SEQ ID NO 17
<211> LENGTH: 10
<212> TYPE: PRT
<213> ORGANISM: Artificial sequence
<220> FEATURE:
<223> OTHER INFORMATION: sequence is synthesized

<400> SEQUENCE: 17

Thr Arg Leu Phe Thr Ile Ile Phe Asp Tyr
1               5                   10

<210> SEQ ID NO 18
<211> LENGTH: 10
<212> TYPE: PRT
```

```
<213> ORGANISM: Artificial sequence
<220> FEATURE:
<223> OTHER INFORMATION: sequence is synthesized

<400> SEQUENCE: 18

Ser Arg Leu Phe Asp Val Ile Phe Asp Tyr
1               5                   10

<210> SEQ ID NO 19
<211> LENGTH: 10
<212> TYPE: PRT
<213> ORGANISM: Artificial sequence
<220> FEATURE:
<223> OTHER INFORMATION: sequence is synthesized

<400> SEQUENCE: 19

Val Arg Leu Phe Gly Ile Ile Phe Asp Tyr
1               5                   10

<210> SEQ ID NO 20
<211> LENGTH: 10
<212> TYPE: PRT
<213> ORGANISM: Artificial sequence
<220> FEATURE:
<223> OTHER INFORMATION: sequence is synthesized

<400> SEQUENCE: 20

Val Arg Leu Tyr Asp Val Ile Phe Asp Tyr
1               5                   10

<210> SEQ ID NO 21
<211> LENGTH: 10
<212> TYPE: PRT
<213> ORGANISM: Artificial sequence
<220> FEATURE:
<223> OTHER INFORMATION: sequence is synthesized

<400> SEQUENCE: 21

Ala Arg Leu Phe Asp Val Ile Phe Asp Tyr
1               5                   10

<210> SEQ ID NO 22
<211> LENGTH: 14
<212> TYPE: PRT
<213> ORGANISM: Artificial sequence
<220> FEATURE:
<223> OTHER INFORMATION: sequence is synthesized

<400> SEQUENCE: 22

Ala Arg Trp Arg Asp Tyr Arg Phe Gly Gly Val Met Asp Tyr
1               5                   10

<210> SEQ ID NO 23
<211> LENGTH: 15
<212> TYPE: PRT
<213> ORGANISM: Artificial sequence
<220> FEATURE:
<223> OTHER INFORMATION: sequence is synthesized

<400> SEQUENCE: 23

Ala Arg Asp Ala Asp Tyr Asp Tyr Ala Gly Trp Ala Phe Asp Tyr
1               5                   10                  15

<210> SEQ ID NO 24
<211> LENGTH: 15
<212> TYPE: PRT
<213> ORGANISM: Artificial sequence
```

```
<220> FEATURE:
<223> OTHER INFORMATION: sequence is synthesized

<400> SEQUENCE: 24

Ala Arg Asp Ala Asp Tyr Ala Tyr Ala Trp Trp Ala Phe Asp Tyr
 1               5                  10                  15

<210> SEQ ID NO 25
<211> LENGTH: 15
<212> TYPE: PRT
<213> ORGANISM: Artificial sequence
<220> FEATURE:
<223> OTHER INFORMATION: sequence is synthesized

<400> SEQUENCE: 25

Ala Arg Asp Val Asp Tyr Tyr Tyr Ala Trp Trp Ala Leu Asp Tyr
 1               5                  10                  15

<210> SEQ ID NO 26
<211> LENGTH: 15
<212> TYPE: PRT
<213> ORGANISM: Artificial sequence
<220> FEATURE:
<223> OTHER INFORMATION: sequence is synthesized

<400> SEQUENCE: 26

Ala Arg Asp Ala Asp Tyr Lys Tyr Ala Phe Trp Ala Phe Asp Tyr
 1               5                  10                  15

<210> SEQ ID NO 27
<211> LENGTH: 11
<212> TYPE: PRT
<213> ORGANISM: Artificial sequence
<220> FEATURE:
<223> OTHER INFORMATION: sequence is synthesized

<400> SEQUENCE: 27

Arg Ala Ser Gln Asp Val Ser Thr Ala Val Ala
 1               5                  10

<210> SEQ ID NO 28
<211> LENGTH: 7
<212> TYPE: PRT
<213> ORGANISM: Artificial sequence
<220> FEATURE:
<223> OTHER INFORMATION: sequence is synthesized

<400> SEQUENCE: 28

Ser Ala Ser Phe Leu Tyr Ser
 1               5

<210> SEQ ID NO 29
<211> LENGTH: 9
<212> TYPE: PRT
<213> ORGANISM: Artificial sequence
<220> FEATURE:
<223> OTHER INFORMATION: sequence is synthesized

<400> SEQUENCE: 29

Gln Gln Ser Tyr Thr Thr Pro Pro Thr
 1               5

<210> SEQ ID NO 30
<211> LENGTH: 9
<212> TYPE: PRT
<213> ORGANISM: Artificial sequence
<220> FEATURE:
```

```
<223> OTHER INFORMATION: sequence is synthesized

<400> SEQUENCE: 30

Gln Gln Ser Tyr Asn Ile Pro Pro Thr
 1               5

<210> SEQ ID NO 31
<211> LENGTH: 9
<212> TYPE: PRT
<213> ORGANISM: Artificial sequence
<220> FEATURE:
<223> OTHER INFORMATION: sequence is synthesized

<400> SEQUENCE: 31

Gln Gln Ser Tyr Trp Thr Pro Leu Thr
 1               5

<210> SEQ ID NO 32
<211> LENGTH: 9
<212> TYPE: PRT
<213> ORGANISM: Artificial sequence
<220> FEATURE:
<223> OTHER INFORMATION: sequence is synthesized

<400> SEQUENCE: 32

Gln Gln Thr Tyr Ala Ile Pro Pro Thr
 1               5

<210> SEQ ID NO 33
<211> LENGTH: 9
<212> TYPE: PRT
<213> ORGANISM: Artificial sequence
<220> FEATURE:
<223> OTHER INFORMATION: sequence is synthesized

<400> SEQUENCE: 33

Gln Gln Ser Tyr Thr Ser Pro Thr Thr
 1               5

<210> SEQ ID NO 34
<211> LENGTH: 9
<212> TYPE: PRT
<213> ORGANISM: Artificial sequence
<220> FEATURE:
<223> OTHER INFORMATION: sequence is synthesized

<400> SEQUENCE: 34

Gln Gln Ser Tyr Thr Thr Pro Thr Thr
 1               5

<210> SEQ ID NO 35
<211> LENGTH: 9
<212> TYPE: PRT
<213> ORGANISM: Artificial sequence
<220> FEATURE:
<223> OTHER INFORMATION: sequence is synthesized

<400> SEQUENCE: 35

Gln Gln Ser Tyr Asn Thr Pro Pro Thr
 1               5

<210> SEQ ID NO 36
<211> LENGTH: 9
<212> TYPE: PRT
<213> ORGANISM: Artificial sequence
<220> FEATURE:
<223> OTHER INFORMATION: sequence is synthesized
```

<400> SEQUENCE: 36

Gln Gln Ser Tyr Ile Thr Pro Pro Thr
1               5

<210> SEQ ID NO 37
<211> LENGTH: 9
<212> TYPE: PRT
<213> ORGANISM: Artificial sequence
<220> FEATURE:
<223> OTHER INFORMATION: sequence is synthesized

<400> SEQUENCE: 37

Gln Gln Ser Tyr Thr Ile Pro Pro Thr
1               5

<210> SEQ ID NO 38
<211> LENGTH: 9
<212> TYPE: PRT
<213> ORGANISM: Artificial sequence
<220> FEATURE:
<223> OTHER INFORMATION: sequence is synthesized

<400> SEQUENCE: 38

Gln Gln Ser Tyr Tyr Ser Pro Leu Thr
1               5

<210> SEQ ID NO 39
<211> LENGTH: 9
<212> TYPE: PRT
<213> ORGANISM: Artificial sequence
<220> FEATURE:
<223> OTHER INFORMATION: sequence is synthesized

<400> SEQUENCE: 39

Gln Gln Thr Tyr Arg Ile Pro Tyr Thr
1               5

<210> SEQ ID NO 40
<211> LENGTH: 87
<212> TYPE: PRT
<213> ORGANISM: Artificial sequence
<220> FEATURE:
<223> OTHER INFORMATION: sequence is synthesized

<400> SEQUENCE: 40

Gln Val Gln Leu Val Gln Ser Gly Ala Glu Val Lys Lys Pro Gly
1               5                   10                  15

Ala Ser Val Lys Val Ser Cys Lys Ala Ser Gly Tyr Thr Phe Thr
                20                  25                  30

Trp Val Arg Gln Ala Pro Gly Gln Gly Leu Glu Trp Met Gly Arg
                35                  40                  45

Val Thr Ile Thr Ala Asp Thr Ser Thr Ser Thr Ala Tyr Met Glu
                50                  55                  60

Leu Ser Ser Leu Arg Ser Glu Asp Thr Ala Val Tyr Tyr Cys Ala
                65                  70                  75

Arg Trp Gly Gln Gly Thr Leu Val Thr Val Ser Ser
                80                  85

<210> SEQ ID NO 41
<211> LENGTH: 81
<212> TYPE: PRT
<213> ORGANISM: Artificial sequence
<220> FEATURE:

<223> OTHER INFORMATION: sequence is synthesized

<400> SEQUENCE: 41

Gln Val Gln Leu Val Gln Ser Gly Ala Glu Val Lys Lys Pro Gly
 1               5                  10                  15
Ala Ser Val Lys Val Ser Cys Lys Ala Ser Trp Val Arg Gln Ala
                20                  25                  30
Pro Gly Gln Gly Leu Glu Trp Met Arg Val Thr Ile Thr Ala Asp
                35                  40                  45
Thr Ser Thr Ser Thr Ala Tyr Met Glu Leu Ser Ser Leu Arg Ser
                50                  55                  60
Glu Asp Thr Ala Val Tyr Tyr Cys Ala Arg Trp Gly Gln Gly Thr
                65                  70                  75
Leu Val Thr Val Ser Ser
                80

<210> SEQ ID NO 42
<211> LENGTH: 80
<212> TYPE: PRT
<213> ORGANISM: Artificial sequence
<220> FEATURE:
<223> OTHER INFORMATION: sequence is synthesized

<400> SEQUENCE: 42

Gln Val Gln Leu Val Gln Ser Gly Ala Glu Val Lys Lys Pro Gly
 1               5                  10                  15
Ala Ser Val Lys Val Ser Cys Lys Ala Ser Trp Val Arg Gln Ala
                20                  25                  30
Pro Gly Gln Gly Leu Glu Trp Met Arg Val Thr Ile Thr Ala Asp
                35                  40                  45
Thr Ser Thr Ser Thr Ala Tyr Met Glu Leu Ser Ser Leu Arg Ser
                50                  55                  60
Glu Asp Thr Ala Val Tyr Tyr Cys Ala Trp Gly Gln Gly Thr Leu
                65                  70                  75
Val Thr Val Ser Ser
                80

<210> SEQ ID NO 43
<211> LENGTH: 79
<212> TYPE: PRT
<213> ORGANISM: Artificial sequence
<220> FEATURE:
<223> OTHER INFORMATION: sequence is synthesized

<400> SEQUENCE: 43

Gln Val Gln Leu Val Gln Ser Gly Ala Glu Val Lys Lys Pro Gly
 1               5                  10                  15
Ala Ser Val Lys Val Ser Cys Lys Ala Ser Trp Val Arg Gln Ala
                20                  25                  30
Pro Gly Gln Gly Leu Glu Trp Met Arg Val Thr Ile Thr Ala Asp
                35                  40                  45
Thr Ser Thr Ser Thr Ala Tyr Met Glu Leu Ser Ser Leu Arg Ser
                50                  55                  60
Glu Asp Thr Ala Val Tyr Tyr Cys Trp Gly Gln Gly Thr Leu Val
                65                  70                  75
Thr Val Ser Ser

<210> SEQ ID NO 44

```
<211> LENGTH: 87
<212> TYPE: PRT
<213> ORGANISM: Artificial sequence
<220> FEATURE:
<223> OTHER INFORMATION: sequence is synthesized

<400> SEQUENCE: 44

Gln Val Gln Leu Gln Glu Ser Gly Pro Gly Leu Val Lys Pro Ser
 1               5                  10                  15

Gln Thr Leu Ser Leu Thr Cys Thr Val Ser Gly Gly Ser Val Ser
            20                  25                  30

Trp Ile Arg Gln Pro Pro Gly Lys Gly Leu Glu Trp Ile Gly Arg
        35                  40                  45

Val Thr Ile Ser Val Asp Thr Ser Lys Asn Gln Phe Ser Leu Lys
    50                  55                  60

Leu Ser Ser Val Thr Ala Ala Asp Thr Ala Val Tyr Tyr Cys Ala
65                  70                  75

Arg Trp Gly Gln Gly Thr Leu Val Thr Val Ser Ser
                80                  85

<210> SEQ ID NO 45
<211> LENGTH: 81
<212> TYPE: PRT
<213> ORGANISM: Artificial sequence
<220> FEATURE:
<223> OTHER INFORMATION: sequence is synthesized

<400> SEQUENCE: 45

Gln Val Gln Leu Gln Glu Ser Gly Pro Gly Leu Val Lys Pro Ser
 1               5                  10                  15

Gln Thr Leu Ser Leu Thr Cys Thr Val Ser Trp Ile Arg Gln Pro
            20                  25                  30

Pro Gly Lys Gly Leu Glu Trp Ile Arg Val Thr Ile Ser Val Asp
        35                  40                  45

Thr Ser Lys Asn Gln Phe Ser Leu Lys Leu Ser Ser Val Thr Ala
    50                  55                  60

Ala Asp Thr Ala Val Tyr Tyr Cys Ala Arg Trp Gly Gln Gly Thr
65                  70                  75

Leu Val Thr Val Ser Ser
                80

<210> SEQ ID NO 46
<211> LENGTH: 80
<212> TYPE: PRT
<213> ORGANISM: Artificial sequence
<220> FEATURE:
<223> OTHER INFORMATION: sequence is synthesized

<400> SEQUENCE: 46

Gln Val Gln Leu Gln Glu Ser Gly Pro Gly Leu Val Lys Pro Ser
 1               5                  10                  15

Gln Thr Leu Ser Leu Thr Cys Thr Val Ser Trp Ile Arg Gln Pro
            20                  25                  30

Pro Gly Lys Gly Leu Glu Trp Ile Arg Val Thr Ile Ser Val Asp
        35                  40                  45

Thr Ser Lys Asn Gln Phe Ser Leu Lys Leu Ser Ser Val Thr Ala
    50                  55                  60

Ala Asp Thr Ala Val Tyr Tyr Cys Ala Trp Gly Gln Gly Thr Leu
65                  70                  75
```

```
Val Thr Val Ser Ser
            80
```

```
<210> SEQ ID NO 47
<211> LENGTH: 79
<212> TYPE: PRT
<213> ORGANISM: Artificial sequence
<220> FEATURE:
<223> OTHER INFORMATION: sequence is synthesized

<400> SEQUENCE: 47

Gln Val Gln Leu Gln Glu Ser Gly Pro Gly Leu Val Lys Pro Ser
 1               5                  10                  15

Gln Thr Leu Ser Leu Thr Cys Thr Val Ser Trp Ile Arg Gln Pro
             20                  25                  30

Pro Gly Lys Gly Leu Glu Trp Ile Arg Val Thr Ile Ser Val Asp
             35                  40                  45

Thr Ser Lys Asn Gln Phe Ser Leu Lys Leu Ser Ser Val Thr Ala
             50                  55                  60

Ala Asp Thr Ala Val Tyr Tyr Cys Trp Gly Gln Gly Thr Leu Val
             65                  70                  75

Thr Val Ser Ser
```

```
<210> SEQ ID NO 48
<211> LENGTH: 87
<212> TYPE: PRT
<213> ORGANISM: Artificial sequence
<220> FEATURE:
<223> OTHER INFORMATION: sequence is synthesized

<400> SEQUENCE: 48

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
             20                  25                  30

Trp Val Arg Gln Ala Pro Gly Lys Gly Leu Glu Trp Val Ser Arg
             35                  40                  45

Phe Thr Ile Ser Arg Asp Asn Ser Lys Asn Thr Leu Tyr Leu Gln
             50                  55                  60

Met Asn Ser Leu Arg Ala Glu Asp Thr Ala Val Tyr Tyr Cys Ala
             65                  70                  75

Arg Trp Gly Gln Gly Thr Leu Val Thr Val Ser Ser
             80                  85
```

```
<210> SEQ ID NO 49
<211> LENGTH: 81
<212> TYPE: PRT
<213> ORGANISM: Artificial sequence
<220> FEATURE:
<223> OTHER INFORMATION: sequence is synthesized

<400> SEQUENCE: 49

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
             20                  25                  30

Pro Gly Lys Gly Leu Glu Trp Val Arg Phe Thr Ile Ser Arg Asp
             35                  40                  45

Asn Ser Lys Asn Thr Leu Tyr Leu Gln Met Asn Ser Leu Arg Ala
             50                  55                  60
```

Glu Asp Thr Ala Val Tyr Tyr Cys Ala Arg Trp Gly Gln Gly Thr
                65                  70                  75

Leu Val Thr Val Ser Ser
                80

<210> SEQ ID NO 50
<211> LENGTH: 80
<212> TYPE: PRT
<213> ORGANISM: Artificial sequence
<220> FEATURE:
<223> OTHER INFORMATION: sequence is synthesized

<400> SEQUENCE: 50

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Arg Asp
                35                  40                  45

Asn Ser Lys Asn Thr Leu Tyr Leu Gln Met Asn Ser Leu Arg Ala
                50                  55                  60

Glu Asp Thr Ala Val Tyr Tyr Cys Ala Trp Gly Gln Gly Thr Leu
                65                  70                  75

Val Thr Val Ser Ser
                80

<210> SEQ ID NO 51
<211> LENGTH: 79
<212> TYPE: PRT
<213> ORGANISM: Artificial sequence
<220> FEATURE:
<223> OTHER INFORMATION: sequence is synthesized

<400> SEQUENCE: 51

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
                20                  25                  30

Pro Gly Lys Gly Leu Glu Trp Val Arg Val Thr Ile Ser Arg Asp
                35                  40                  45

Asn Ser Lys Asn Thr Leu Tyr Leu Gln Met Asn Ser Leu Arg Ala
                50                  55                  60

Glu Asp Thr Ala Val Tyr Tyr Cys Trp Gly Gln Gly Thr Leu Val
                65                  70                  75

Thr Val Ser Ser

<210> SEQ ID NO 52
<211> LENGTH: 87
<212> TYPE: PRT
<213> ORGANISM: Artificial sequence
<220> FEATURE:
<223> OTHER INFORMATION: sequence is synthesized

<400> SEQUENCE: 52

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Trp Val Arg Gln Ala Pro Gly Lys Gly Leu Glu Trp Val Ser Arg

```
                35                  40                  45
Phe Thr Ile Ser Ala Asp Thr Ser Lys Asn Thr Ala Tyr Leu Gln
             50                  55                  60

Met Asn Ser Leu Arg Ala Glu Asp Thr Ala Val Tyr Tyr Cys Ser
         65                  70                  75

Arg Trp Gly Gln Gly Thr Leu Val Thr Val Ser Ser
     80                  85

<210> SEQ ID NO 53
<211> LENGTH: 81
<212> TYPE: PRT
<213> ORGANISM: Artificial sequence
<220> FEATURE:
<223> OTHER INFORMATION: sequence is synthesized

<400> SEQUENCE: 53

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
             20                  25                  30

Pro Gly Lys Gly Leu Glu Trp Val Arg Phe Thr Ile Ser Ala Asp
         35                  40                  45

Thr Ser Lys Asn Thr Ala Tyr Leu Gln Met Asn Ser Leu Arg Ala
     50                  55                  60

Glu Asp Thr Ala Val Tyr Tyr Cys Ser Arg Trp Gly Gln Gly Thr
 65                  70                  75

Leu Val Thr Val Ser Ser
             80

<210> SEQ ID NO 54
<211> LENGTH: 80
<212> TYPE: PRT
<213> ORGANISM: Artificial sequence
<220> FEATURE:
<223> OTHER INFORMATION: sequence is synthesized

<400> SEQUENCE: 54

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
             20                  25                  30

Pro Gly Lys Gly Leu Glu Trp Val Arg Phe Thr Ile Ser Ala Asp
         35                  40                  45

Thr Ser Lys Asn Thr Ala Tyr Leu Gln Met Asn Ser Leu Arg Ala
     50                  55                  60

Glu Asp Thr Ala Val Tyr Tyr Cys Ser Trp Gly Gln Gly Thr Leu
 65                  70                  75

Val Thr Val Ser Ser
             80

<210> SEQ ID NO 55
<211> LENGTH: 87
<212> TYPE: PRT
<213> ORGANISM: Artificial sequence
<220> FEATURE:
<223> OTHER INFORMATION: sequence is synthesized

<400> SEQUENCE: 55

Glu Val Gln Leu Val Glu Ser Gly Gly Gly Leu Val Gln Pro Gly
 1               5                  10                  15
```

Gly Ser Leu Arg Leu Ser Cys Ala Ala Ser Gly Phe Asn Ile Lys
            20                  25                  30

Trp Val Arg Gln Ala Pro Gly Lys Gly Leu Glu Trp Val Ser Arg
        35                  40                  45

Phe Thr Ile Ser Ala Asp Thr Ser Lys Asn Thr Ala Tyr Leu Gln
    50                  55                  60

Met Asn Ser Leu Arg Ala Glu Asp Thr Ala Val Tyr Tyr Cys Ala
65                  70                  75

Arg Trp Gly Gln Gly Thr Leu Val Thr Val Ser Ser
            80                  85

<210> SEQ ID NO 56
<211> LENGTH: 81
<212> TYPE: PRT
<213> ORGANISM: Artificial sequence
<220> FEATURE:
<223> OTHER INFORMATION: sequence is synthesized

<400> SEQUENCE: 56

Glu Val Gln Leu Val Glu Ser Gly Gly Gly Leu Val Gln Pro Gly
1               5                   10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
        35                  40                  45

Thr Ser Lys Asn Thr Ala Tyr Leu Gln Met Asn Ser Leu Arg Ala
    50                  55                  60

Glu Asp Thr Ala Val Tyr Tyr Cys Ala Arg Trp Gly Gln Gly Thr
65                  70                  75

Leu Val Thr Val Ser Ser
            80

<210> SEQ ID NO 57
<211> LENGTH: 80
<212> TYPE: PRT
<213> ORGANISM: Artificial sequence
<220> FEATURE:
<223> OTHER INFORMATION: sequence is synthesized

<400> SEQUENCE: 57

Glu Val Gln Leu Val Glu Ser Gly Gly Gly Leu Val Gln Pro Gly
1               5                   10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
        35                  40                  45

Thr Ser Lys Asn Thr Ala Tyr Leu Gln Met Asn Ser Leu Arg Ala
    50                  55                  60

Glu Asp Thr Ala Val Tyr Tyr Cys Ala Trp Gly Gln Gly Thr Leu
65                  70                  75

Val Thr Val Ser Ser
            80

<210> SEQ ID NO 58
<211> LENGTH: 79
<212> TYPE: PRT
<213> ORGANISM: Artificial sequence
<220> FEATURE:
<223> OTHER INFORMATION: sequence is synthesized

<400> SEQUENCE: 58

Glu Val Gln Leu Val Glu Ser Gly Gly Gly Leu Val Gln Pro Gly
1               5                   10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
        35                  40                  45

Thr Ser Lys Asn Thr Ala Tyr Leu Gln Met Asn Ser Leu Arg Ala
    50                  55                  60

Glu Asp Thr Ala Val Tyr Tyr Cys Trp Gly Gln Gly Thr Leu Val
65                  70                  75

Thr Val Ser Ser

<210> SEQ ID NO 59
<211> LENGTH: 80
<212> TYPE: PRT
<213> ORGANISM: Artificial sequence
<220> FEATURE:
<223> OTHER INFORMATION: sequence is synthesized

<400> SEQUENCE: 59

Asp Ile Gln Met Thr Gln Ser Pro Ser Ser Leu Ser Ala Ser Val
1               5                   10                  15

Gly Asp Arg Val Thr Ile Thr Cys Trp Tyr Gln Gln Lys Pro Gly
            20                  25                  30

Lys Ala Pro Lys Leu Leu Ile Tyr Gly Val Pro Ser Arg Phe Ser
        35                  40                  45

Gly Ser Gly Ser Gly Thr Asp Phe Thr Leu Thr Ile Ser Ser Leu
    50                  55                  60

Gln Pro Glu Asp Phe Ala Thr Tyr Tyr Cys Phe Gly Gln Gly Thr
65                  70                  75

Lys Val Glu Ile Lys
            80

<210> SEQ ID NO 60
<211> LENGTH: 80
<212> TYPE: PRT
<213> ORGANISM: Artificial sequence
<220> FEATURE:
<223> OTHER INFORMATION: sequence is synthesized

<400> SEQUENCE: 60

Asp Ile Val Met Thr Gln Ser Pro Leu Ser Leu Pro Val Thr Pro
1               5                   10                  15

Gly Glu Pro Ala Ser Ile Ser Cys Trp Tyr Leu Gln Lys Pro Gly
            20                  25                  30

Gln Ser Pro Gln Leu Leu Ile Tyr Gly Val Pro Asp Arg Phe Ser
        35                  40                  45

Gly Ser Gly Ser Gly Thr Asp Phe Thr Leu Lys Ile Ser Arg Val
    50                  55                  60

Glu Ala Glu Asp Val Gly Val Tyr Tyr Cys Phe Gly Gln Gly Thr
65                  70                  75

Lys Val Glu Ile Lys
            80

<210> SEQ ID NO 61
<211> LENGTH: 80

```
<212> TYPE: PRT
<213> ORGANISM: Artificial sequence
<220> FEATURE:
<223> OTHER INFORMATION: sequence is synthesized

<400> SEQUENCE: 61

Glu Ile Val Leu Thr Gln Ser Pro Gly Thr Leu Ser Leu Ser Pro
 1               5                  10                  15

Gly Glu Arg Ala Thr Leu Ser Cys Trp Tyr Gln Gln Lys Pro Gly
                20                  25                  30

Gln Ala Pro Arg Leu Leu Ile Tyr Gly Ile Pro Asp Arg Phe Ser
                35                  40                  45

Gly Ser Gly Ser Gly Thr Asp Phe Thr Leu Thr Ile Ser Arg Leu
            50                  55                  60

Glu Pro Glu Asp Phe Ala Val Tyr Tyr Cys Phe Gly Gln Gly Thr
65                  70                  75

Lys Val Glu Ile Lys
            80

<210> SEQ ID NO 62
<211> LENGTH: 80
<212> TYPE: PRT
<213> ORGANISM: Artificial sequence
<220> FEATURE:
<223> OTHER INFORMATION: sequence is synthesized

<400> SEQUENCE: 62

Asp Ile Val Met Thr Gln Ser Pro Asp Ser Leu Ala Val Ser Leu
 1               5                  10                  15

Gly Glu Arg Ala Thr Ile Asn Cys Trp Tyr Gln Gln Lys Pro Gly
                20                  25                  30

Gln Pro Pro Lys Leu Leu Ile Tyr Gly Val Pro Asp Arg Phe Ser
                35                  40                  45

Gly Ser Gly Ser Gly Thr Asp Phe Thr Leu Thr Ile Ser Ser Leu
            50                  55                  60

Gln Ala Glu Asp Val Ala Val Tyr Tyr Cys Phe Gly Gln Gly Thr
65                  70                  75

Lys Val Glu Ile Lys
            80

<210> SEQ ID NO 63
<211> LENGTH: 25
<212> TYPE: PRT
<213> ORGANISM: Artificial sequence
<220> FEATURE:
<223> OTHER INFORMATION: sequence is synthesized

<400> SEQUENCE: 63

Glu Val Gln Leu Val Glu Ser Gly Gly Gly Leu Val Gln Pro Gly
 1               5                  10                  15

Gly Ser Leu Arg Leu Ser Cys Ala Ala Ser
                20                  25

<210> SEQ ID NO 64
<211> LENGTH: 13
<212> TYPE: PRT
<213> ORGANISM: Artificial sequence
<220> FEATURE:
<223> OTHER INFORMATION: sequence is synthesized

<400> SEQUENCE: 64
```

-continued

Trp Val Arg Gln Ala Pro Gly Lys Gly Leu Glu Trp Val
1               5                   10

<210> SEQ ID NO 65
<211> LENGTH: 30
<212> TYPE: PRT
<213> ORGANISM: Artificial sequence
<220> FEATURE:
<223> OTHER INFORMATION: sequence is synthesized

<400> SEQUENCE: 65

Arg Phe Thr Ile Ser Ala Asp Thr Ser Lys Asn Thr Ala Tyr Leu
1               5                   10                  15
Gln Met Asn Ser Leu Arg Ala Glu Asp Thr Ala Val Tyr Tyr Cys
                20                  25                  30

<210> SEQ ID NO 66
<211> LENGTH: 11
<212> TYPE: PRT
<213> ORGANISM: Artificial sequence
<220> FEATURE:
<223> OTHER INFORMATION: sequence is synthesized

<400> SEQUENCE: 66

Trp Gly Gln Gly Thr Leu Val Thr Val Ser Ser
1               5                   10

<210> SEQ ID NO 67
<211> LENGTH: 23
<212> TYPE: PRT
<213> ORGANISM: Artificial sequence
<220> FEATURE:
<223> OTHER INFORMATION: sequence is synthesized

<400> SEQUENCE: 67

Asp Ile Gln Met Thr Gln Ser Pro Ser Ser Leu Ser Ala Ser Val
1               5                   10                  15
Gly Asp Arg Val Thr Ile Thr Cys
                20

<210> SEQ ID NO 68
<211> LENGTH: 15
<212> TYPE: PRT
<213> ORGANISM: Artificial sequence
<220> FEATURE:
<223> OTHER INFORMATION: sequence is synthesized

<400> SEQUENCE: 68

Trp Tyr Gln Gln Lys Pro Gly Lys Ala Pro Lys Leu Leu Ile Tyr
1               5                   10                  15

<210> SEQ ID NO 69
<211> LENGTH: 32
<212> TYPE: PRT
<213> ORGANISM: Artificial sequence
<220> FEATURE:
<223> OTHER INFORMATION: sequence is synthesized

<400> SEQUENCE: 69

Gly Val Pro Ser Arg Phe Ser Gly Ser Arg Ser Gly Thr Asp Phe
1               5                   10                  15
Thr Leu Thr Ile Ser Ser Leu Gln Pro Glu Asp Phe Ala Thr Tyr
                20                  25                  30
Tyr Cys

<210> SEQ ID NO 70
<211> LENGTH: 10
<212> TYPE: PRT
<213> ORGANISM: Artificial sequence
<220> FEATURE:
<223> OTHER INFORMATION: sequence is synthesized

<400> SEQUENCE: 70

Phe Gly Gln Gly Thr Lys Val Glu Ile Lys
1               5                   10

<210> SEQ ID NO 71
<211> LENGTH: 107
<212> TYPE: PRT
<213> ORGANISM: Artificial sequence
<220> FEATURE:
<223> OTHER INFORMATION: sequence is synthesized

<400> SEQUENCE: 71

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Arg Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
            95                  100                 105

Ile Lys

<210> SEQ ID NO 72
<211> LENGTH: 107
<212> TYPE: PRT
<213> ORGANISM: Artificial sequence
<220> FEATURE:
<223> OTHER INFORMATION: sequence is synthesized

<400> SEQUENCE: 72

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
            95                  100                 105

Ile Lys

-continued

```
<210> SEQ ID NO 73
<211> LENGTH: 117
<212> TYPE: PRT
<213> ORGANISM: Artificial sequence
<220> FEATURE:
<223> OTHER INFORMATION: sequence is synthesized

<400> SEQUENCE: 73

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Asp Ser Asp Ile His Trp Val Arg Gln Ala Pro Gly Lys Gly Leu
                35                  40                  45

Glu Trp Val Ala Trp Ile Ser Pro Tyr Val Gly Phe Thr Asp Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ala Arg Leu Phe Asp Val Ile Phe Asp
                95                 100                 105

Tyr Trp Gly Gln Gly Thr Leu Val Thr Val Ser Ser
                110                 115

<210> SEQ ID NO 74
<211> LENGTH: 108
<212> TYPE: PRT
<213> ORGANISM: Artificial sequence
<220> FEATURE:
<223> OTHER INFORMATION: sequence is synthesized

<400> SEQUENCE: 74

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                 100                 105

Ile Lys Arg

<210> SEQ ID NO 75
<211> LENGTH: 108
<212> TYPE: PRT
<213> ORGANISM: Artificial sequence
<220> FEATURE:
<223> OTHER INFORMATION: sequence is synthesized

<400> SEQUENCE: 75

Asp Ile Gln Met Thr Gln Ser Pro Ser Ser Leu Ser Ala Ser Val
 1               5                  10                  15
```

```
Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Ser Tyr Asn Ile Pro Pro Thr Phe Gly Gln Gly Thr Lys Val Glu
            95                 100                 105

Ile Lys Arg

<210> SEQ ID NO 76
<211> LENGTH: 108
<212> TYPE: PRT
<213> ORGANISM: Artificial sequence
<220> FEATURE:
<223> OTHER INFORMATION: sequence is synthesized

<400> SEQUENCE: 76

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Ser Tyr Trp Thr Pro Leu Thr Phe Gly Gln Gly Thr Lys Val Glu
            95                 100                 105

Ile Lys Arg

<210> SEQ ID NO 77
<211> LENGTH: 108
<212> TYPE: PRT
<213> ORGANISM: Artificial sequence
<220> FEATURE:
<223> OTHER INFORMATION: sequence is synthesized

<400> SEQUENCE: 77

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
            50                  55                  60

Arg Phe Ser Gly Ser Gly Ser Gly Thr Asp Phe Thr Leu Thr Ile
            65                  70                  75
```

```
Ser Ser Leu Gln Pro Glu Asp Phe Ala Thr Tyr Tyr Cys Gln Gln
            80                  85                  90

Thr Tyr Ala Ile Pro Pro Thr Phe Gly Gln Gly Thr Lys Val Glu
         95                 100                 105

Ile Lys Arg

<210> SEQ ID NO 78
<211> LENGTH: 108
<212> TYPE: PRT
<213> ORGANISM: Artificial sequence
<220> FEATURE:
<223> OTHER INFORMATION: sequence is synthesized

<400> SEQUENCE: 78

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Ser Tyr Thr Ser Pro Thr Thr Phe Gly Gln Gly Thr Lys Val Glu
         95                 100                 105

Ile Lys Arg

<210> SEQ ID NO 79
<211> LENGTH: 108
<212> TYPE: PRT
<213> ORGANISM: Artificial sequence
<220> FEATURE:
<223> OTHER INFORMATION: sequence is synthesized

<400> SEQUENCE: 79

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Ser Tyr Thr Thr Pro Thr Thr Phe Gly Gln Gly Thr Lys Val Glu
         95                 100                 105

Ile Lys Arg

<210> SEQ ID NO 80
<211> LENGTH: 108
<212> TYPE: PRT
<213> ORGANISM: Artificial sequence
```

<220> FEATURE:
<223> OTHER INFORMATION: sequence is synthesized

<400> SEQUENCE: 80

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Tyr Asn Thr Pro Pro Thr Phe Gly Gln Gly Thr Lys Val Glu
                95                  100                 105

Ile Lys Arg

<210> SEQ ID NO 81
<211> LENGTH: 108
<212> TYPE: PRT
<213> ORGANISM: Artificial sequence
<220> FEATURE:
<223> OTHER INFORMATION: sequence is synthesized

<400> SEQUENCE: 81

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Ser Tyr Ile Thr Pro Pro Thr Phe Gly Gln Gly Thr Lys Val Glu
                95                  100                 105

Ile Lys Arg

<210> SEQ ID NO 82
<211> LENGTH: 108
<212> TYPE: PRT
<213> ORGANISM: Artificial sequence
<220> FEATURE:
<223> OTHER INFORMATION: sequence is synthesized

<400> SEQUENCE: 82

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

```
Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Thr Ile Pro Pro Thr Phe Gly Gln Gly Thr Lys Val Glu
                95                 100                 105

Ile Lys Arg

<210> SEQ ID NO 83
<211> LENGTH: 108
<212> TYPE: PRT
<213> ORGANISM: Artificial sequence
<220> FEATURE:
<223> OTHER INFORMATION: sequence is synthesized

<400> SEQUENCE: 83

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Tyr Ser Pro Leu Thr Phe Gly Gln Gly Thr Lys Val Glu
                95                 100                 105

Ile Lys Arg

<210> SEQ ID NO 84
<211> LENGTH: 122
<212> TYPE: PRT
<213> ORGANISM: Artificial sequence
<220> FEATURE:
<223> OTHER INFORMATION: sequence is synthesized

<400> SEQUENCE: 84

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Asn Trp Ile His Trp Val Arg Gln Ala Pro Gly Lys Gly Leu
                35                  40                  45

Glu Trp Val Ala Val Ile Ser Pro Tyr Ser Gly Ala Thr Tyr Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ala Arg Asp Ala Asp Tyr Lys Tyr Ala
                95                 100                 105
```

```
Phe Trp Ala Phe Asp Tyr Trp Gly Gln Gly Thr Leu Val Thr Val
                110                 115                 120

Ser Ser

<210> SEQ ID NO 85
<211> LENGTH: 108
<212> TYPE: PRT
<213> ORGANISM: Artificial sequence
<220> FEATURE:
<223> OTHER INFORMATION: sequence is synthesized

<400> SEQUENCE: 85

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Ser
                 20                  25                  30

Thr Ala Val Ala Trp Tyr Gln Gln Lys Pro Gly Lys Ala Pro Lys
                 35                  40                  45

Leu Leu Ile Tyr Ser Ala Ser Phe Leu Tyr Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

Ser Tyr Thr Thr Pro Pro Thr Phe Gly Gln Gly Thr Lys Val Glu
                 95                 100                 105

Ile Lys Arg

<210> SEQ ID NO 86
<211> LENGTH: 2031
<212> TYPE: DNA
<213> ORGANISM: Artificial sequence
<220> FEATURE:
<223> OTHER INFORMATION: sequence is synthesized

<400> SEQUENCE: 86
cgcggggtgt tctggtgtcc cccgccccgc ctctccaaaa agctacaccg         50
acgcggaccg cggcggcgtc ctccctcgcc ctcgcttcac ctcgcgggct        100
ccgaatgcgg ggagctcgga tgtccggttt cctgtgaggc ttttacctga        150
cacccgccgc ctttccccgg cactggctgg gagggcgccc tgcaaagttg        200
ggaacgcgga gccccggacc cgctcccgcc gcctccggct cgcccagggg        250
gggtcgccgg gaggagcccg ggggagaggg accaggaggg gcccgcggcc        300
tcgcaggggc gcccgcgccc ccaccccctgc ccccgccagc ggaccggtcc        350
cccacccccg gtccttccac catgcacttg ctgggcttct tctctgtggc        400
gtgttctctg ctcgccgctg cgctgctccc gggtcctcgc gaggcgcccg        450
ccgccgccgc cgccttcgag tccggactcg acctctcgga cgcggagccc        500
gacgcgggcg aggccacggc ttatgcaagc aaagatctgg aggagcagtt        550
acggtctgtg tccagtgtag atgaactcat gactgtactc tacccagaat        600
attggaaaat gtacaagtgt cagctaagga aaggaggctg gcaacataac        650
agagaacagg ccaacctcaa ctcaaggaca gaagagacta taaaatttgc        700
tgcagcacat tataatacag agatcttgaa aagtattgat aatagagtgga       750 gaaagactca atgcatgcca cgggaggtgt gtatagatgt ggggaaggag        800
```

-continued

| | |
|---|---|
| tttggagtcg cgacaaacac cttctttaaa cctccatgtg tgtccgtcta | 850 |
| cagatgtggg ggttgctgca atagtgaggg gctgcagtgc atgaacacca | 900 |
| gcacgagcta cctcagcaag acgttatttg aaattacagt gcctctctct | 950 |
| caaggcccca aaccagtaac aatcagtttt gccaatcaca cttcctgccg | 1000 |
| atgcatgtct aaactggatg tttacagaca agttcattcc attattagac | 1050 |
| gttccctgcc agcaacacta ccacagtgtc aggcagcgaa caagacctgc | 1100 |
| cccaccaatt acatgtggaa taatcacatc tgcagatgcc tggctcagga | 1150 |
| agattttatg ttttcctcgg atgctggaga tgactcaaca gatggattcc | 1200 |
| atgacatctg tggaccaaac aaggagctgg atgaagagac ctgtcagtgt | 1250 |
| gtctgcagag cggggcttcg gcctgccagc tgtggacccc acaaagaact | 1300 |
| agacagaaac tcatgccagt gtgtctgtaa aaacaaactc ttccccagcc | 1350 |
| aatgtggggc caaccgagaa tttgatgaaa cacatgccag tgtgtatgt | 1400 |
| aaaagaacct gccccagaaa tcaaccccta atcctggaa aatgtgcctg | 1450 |
| tgaatgtaca gaaagtccac agaaatgctt gttaaaagga agaagttcc | 1500 |
| accaccaaac atgcagctgt tacagacggc catgtacgaa ccgccagaag | 1550 |
| gcttgtgagc caggattttc atatagtgaa gaagtgtgtc gttgtgtccc | 1600 |
| ttcatattgg aaaagaccac aaatgagcta agattgtact gttttccagt | 1650 |
| tcatcgattt tctattatgg aaaactgtgt tgccacagta gaactgtctg | 1700 |
| tgaacagaga gacccttgtg ggtccatgct aacaaagaca aaagtctgtc | 1750 |
| tttcctgaac catgtggata actttacaga aatggactgg agctcatctg | 1800 |
| caaaaggcct cttgtaaaga ctggttttct gccaatgacc aaacagccaa | 1850 |
| gattttcctc ttgtgatttc tttaaaagaa tgactatata atttatttcc | 1900 |
| actaaaaata ttgtttctgc attcattttt atagcaacaa caattggtaa | 1950 |
| aactcactgt gatcaatatt tttatatcat gcaaaatatg tttaaaataa | 2000 |
| aatgaaaatt gtattaaaaa aaaaaaaaa a | 2031 |

<210> SEQ ID NO 87
<211> LENGTH: 419
<212> TYPE: PRT
<213> ORGANISM: Artificial sequence
<220> FEATURE:
<223> OTHER INFORMATION: sequence is synthesized

<400> SEQUENCE: 87

Met His Leu Leu Gly Phe Phe Ser Val Ala Cys Ser Leu Leu Ala
1               5                   10                  15

Ala Ala Leu Leu Pro Gly Pro Arg Glu Ala Pro Ala Ala Ala Ala
                20                  25                  30

Ala Phe Glu Ser Gly Leu Asp Leu Ser Asp Ala Glu Pro Asp Ala
                35                  40                  45

Gly Glu Ala Thr Ala Tyr Ala Ser Lys Asp Leu Glu Glu Gln Leu
                50                  55                  60

Arg Ser Val Ser Ser Val Asp Glu Leu Met Thr Val Leu Tyr Pro
                65                  70                  75

Glu Tyr Trp Lys Met Tyr Lys Cys Gln Leu Arg Lys Gly Gly Trp
                80                  85                  90

```
Gln His Asn Arg Glu Gln Ala Asn Leu Asn Ser Arg Thr Glu Glu
                 95                 100                 105

Thr Ile Lys Phe Ala Ala Ala His Tyr Asn Thr Glu Ile Leu Lys
            110                 115                 120

Ser Ile Asp Asn Glu Trp Arg Lys Thr Gln Cys Met Pro Arg Glu
            125                 130                 135

Val Cys Ile Asp Val Gly Lys Glu Phe Gly Val Ala Thr Asn Thr
            140                 145                 150

Phe Phe Lys Pro Pro Cys Val Ser Val Tyr Arg Cys Gly Gly Cys
            155                 160                 165

Cys Asn Ser Glu Gly Leu Gln Cys Met Asn Thr Ser Thr Ser Tyr
            170                 175                 180

Leu Ser Lys Thr Leu Phe Glu Ile Thr Val Pro Leu Ser Gln Gly
            185                 190                 195

Pro Lys Pro Val Thr Ile Ser Phe Ala Asn His Thr Ser Cys Arg
            200                 205                 210

Cys Met Ser Lys Leu Asp Val Tyr Arg Gln Val His Ser Ile Ile
            215                 220                 225

Arg Arg Ser Leu Pro Ala Thr Leu Pro Gln Cys Gln Ala Ala Asn
            230                 235                 240

Lys Thr Cys Pro Thr Asn Tyr Met Trp Asn Asn His Ile Cys Arg
            245                 250                 255

Cys Leu Ala Gln Glu Asp Phe Met Phe Ser Ser Asp Ala Gly Asp
            260                 265                 270

Asp Ser Thr Asp Gly Phe His Asp Ile Cys Gly Pro Asn Lys Glu
            275                 280                 285

Leu Asp Glu Glu Thr Cys Gln Cys Val Cys Arg Ala Gly Leu Arg
            290                 295                 300

Pro Ala Ser Cys Gly Pro His Lys Glu Leu Asp Arg Asn Ser Cys
            305                 310                 315

Gln Cys Val Cys Lys Asn Lys Leu Phe Pro Ser Gln Cys Gly Ala
            320                 325                 330

Asn Arg Glu Phe Asp Glu Asn Thr Cys Gln Cys Val Cys Lys Arg
            335                 340                 345

Thr Cys Pro Arg Asn Gln Pro Leu Asn Pro Gly Lys Cys Ala Cys
            350                 355                 360

Glu Cys Thr Glu Ser Pro Gln Lys Cys Leu Leu Lys Gly Lys Lys
            365                 370                 375

Phe His His Gln Thr Cys Ser Cys Tyr Arg Arg Pro Cys Thr Asn
            380                 385                 390

Arg Gln Lys Ala Cys Glu Pro Gly Phe Ser Tyr Ser Glu Glu Val
            395                 400                 405

Cys Arg Cys Val Pro Ser Tyr Trp Lys Arg Pro Gln Met Ser
            410                 415

<210> SEQ ID NO 88
<211> LENGTH: 419
<212> TYPE: PRT
<213> ORGANISM: Artificial sequence
<220> FEATURE:
<223> OTHER INFORMATION: sequence is synthesized
```

```
<400> SEQUENCE: 88

Met His Leu Leu Gly Phe Phe Ser Val Ala Cys Ser Leu Leu Ala
 1               5                  10                  15

Ala Ala Leu Leu Pro Gly Pro Arg Glu Ala Pro Ala Ala Ala Ala
                20                  25                  30

Ala Phe Glu Ser Gly Leu Asp Leu Ser Asp Ala Glu Pro Asp Ala
                35                  40                  45

Gly Glu Ala Thr Ala Tyr Ala Ser Lys Asp Leu Glu Glu Gln Leu
                50                  55                  60

Arg Ser Val Ser Val Asp Glu Leu Met Thr Val Leu Tyr Pro
                65                  70                  75

Glu Tyr Trp Lys Met Tyr Lys Cys Gln Leu Arg Lys Gly Gly Trp
                80                  85                  90

Gln His Asn Arg Glu Gln Ala Asn Leu Asn Ser Arg Thr Glu Glu
                95                  100                 105

Thr Ile Lys Phe Ala Ala Ala His Tyr Asn Thr Glu Ile Leu Lys
                110                 115                 120

Ser Ile Asp Asn Glu Trp Arg Lys Thr Gln Cys Met Pro Arg Glu
                125                 130                 135

Val Ser Ile Asp Val Gly Lys Glu Phe Gly Val Ala Thr Asn Thr
                140                 145                 150

Phe Phe Lys Pro Pro Cys Val Ser Val Tyr Arg Cys Gly Gly Cys
                155                 160                 165

Cys Asn Ser Glu Gly Leu Gln Cys Met Asn Thr Ser Thr Ser Tyr
                170                 175                 180

Leu Ser Lys Thr Leu Phe Glu Ile Thr Val Pro Leu Ser Gln Gly
                185                 190                 195

Pro Lys Pro Val Thr Ile Ser Phe Ala Asn His Thr Ser Cys Arg
                200                 205                 210

Cys Met Ser Lys Leu Asp Val Tyr Arg Gln Val His Ser Ile Ile
                215                 220                 225

Arg Arg Ser Leu Pro Ala Thr Leu Pro Gln Cys Gln Ala Ala Asn
                230                 235                 240

Lys Thr Cys Pro Thr Asn Tyr Met Trp Asn Asn His Ile Cys Arg
                245                 250                 255

Cys Leu Ala Gln Glu Asp Phe Met Phe Ser Ser Asp Ala Gly Asp
                260                 265                 270

Asp Ser Thr Asp Gly Phe His Asp Ile Cys Gly Pro Asn Lys Glu
                275                 280                 285

Leu Asp Glu Glu Thr Cys Gln Cys Val Cys Arg Ala Gly Leu Arg
                290                 295                 300

Pro Ala Ser Cys Gly Pro His Lys Glu Leu Asp Arg Asn Ser Cys
                305                 310                 315

Gln Cys Val Cys Lys Asn Lys Leu Phe Pro Ser Gln Cys Gly Ala
                320                 325                 330

Asn Arg Glu Phe Asp Glu Asn Thr Cys Gln Cys Val Cys Lys Arg
                335                 340                 345

Thr Cys Pro Arg Asn Gln Pro Leu Asn Pro Gly Lys Cys Ala Cys
                350                 355                 360

Glu Cys Thr Glu Ser Pro Gln Lys Cys Leu Leu Lys Gly Lys Lys
                365                 370                 375

Phe His His Gln Thr Cys Ser Cys Tyr Arg Arg Pro Cys Thr Asn
                380                 385                 390
```

```
Arg Gln Lys Ala Cys Glu Pro Gly Phe Ser Tyr Ser Glu Glu Val
            395                 400                 405

Cys Arg Cys Val Pro Ser Tyr Trp Lys Arg Pro Gln Met Ser
            410                 415

<210> SEQ ID NO 89
<211> LENGTH: 32
<212> TYPE: PRT
<213> ORGANISM: Artificial sequence
<220> FEATURE:
<223> OTHER INFORMATION: sequence is synthesized

<400> SEQUENCE: 89

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys

<210> SEQ ID NO 90
<211> LENGTH: 30
<212> TYPE: PRT
<213> ORGANISM: Artificial sequence
<220> FEATURE:
<223> OTHER INFORMATION: sequence is synthesized

<400> SEQUENCE: 90

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
                20                  25                  30

<210> SEQ ID NO 91
<211> LENGTH: 18
<212> TYPE: PRT
<213> ORGANISM: Artificial sequence
<220> FEATURE:
<223> OTHER INFORMATION: sequence is synthesized

<400> SEQUENCE: 91

Gly Phe Ile Ser Pro Gly Val Gly Tyr Ser Tyr Tyr Ala Asp Ser
 1               5                  10                  15

Val Lys Gly
```